United States Patent
Shipps, Jr. et al.

(10) Patent No.: US 7,115,749 B2
(45) Date of Patent: Oct. 3, 2006

(54) SUBSTITUTED 5-OXO PYRAZOLES AND [1,2,4]TRIAZOLES AS ANTIVIRAL AGENTS

(75) Inventors: Gerald W. Shipps, Jr., Stoneham, MA (US); Tong Wang, Cambridge, MA (US); Kristin E. Rosner, Watertown, MA (US); Patrick J. Curran, Winthrop, MA (US); Alan B. Cooper, West Caldwell, NJ (US); Viyyoor M. Girijavallabhan, Parsippany, NJ (US)

(73) Assignee: Schering Corporation, Kenilworth, NJ (US)

( * ) Notice: Subject to any disclaimer, the term of this patent is extended or adjusted under 35 U.S.C. 154(b) by 0 days.

(21) Appl. No.: 11/259,397

(22) Filed: Oct. 26, 2005

(65) Prior Publication Data

US 2006/0111412 A1    May 25, 2006

Related U.S. Application Data

(60) Provisional application No. 60/623,182, filed on Oct. 29, 2004.

(51) Int. Cl.
| | |
|---|---|
| C07D 231/20 | (2006.01) |
| C07D 401/14 | (2006.01) |
| C07D 257/04 | (2006.01) |
| A61K 31/4152 | (2006.01) |

(52) U.S. Cl. .............. 548/369.7; 546/276.1; 548/253; 514/407

(58) Field of Classification Search ............. 548/367.1, 548/369.7
See application file for complete search history.

(56) References Cited

U.S. PATENT DOCUMENTS 6,342,516 B1 *    1/2002    Umeda et al. ........... 548/311.1

FOREIGN PATENT DOCUMENTS

| | | |
|---|---|---|
| DE | 198 55 808 A1 | 6/2000 |
| WO | WO 03/037894 A | 5/2003 |
| WO | WO 03/082848 A | 10/2003 |
| WO | WO 03/095441 A | 11/2003 |
| WO | WO 03/101993 A | 12/2003 |
| WO | WO 2004-009543 A | 1/2004 |
| WO | WO 2004/037818 A | 5/2004 |
| WO | WO 2005/092863 A | 10/2005 |

OTHER PUBLICATIONS

Copy of International Search Report for PCT/US2005/038801 mailed Apr. 24, 2006—5pgs.

* cited by examiner

*Primary Examiner*—Kamal A. Saeed
*Assistant Examiner*—Shawquia Young
(74) *Attorney, Agent, or Firm*—Palsiyur S. Kalyanaraman

(57) ABSTRACT

The present invention provides compounds of formula I wherein X and $R^1$–$R^7$ are as defined herein. Compositions containing these compounds, and methods for inhibiting HCV RNA-dependent RNA polymerase and treating hepatitis C and related disorders using these compounds and compositions are also provided

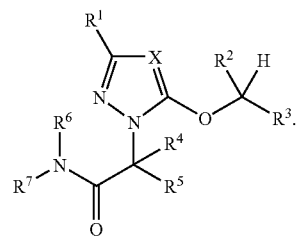

I

30 Claims, No Drawings

SUBSTITUTED 5-OXO PYRAZOLES AND [1,2,4]TRIAZOLES AS ANTIVIRAL AGENTS

This application claims priority from U.S. provisional patent application Ser. No. 60/623,182 filed Oct. 29, 2004.

FIELD OF THE INVENTION

This invention relates to the inhibition of hepatitis C virus (HCV) replication. In particular, the invention relates to substituted pyrazole and [1,2,4]triazole compounds, compositions containing these compounds, and methods for inhibiting HCV RNA-dependent RNA polymerase and treating hepatitis C and related disorders using these compounds and compositions.

BACKGROUND OF THE INVENTION

Hepatitis C virus (HCV) is a (+)-sense single-stranded RNA virus in the Flaviviridae family. Its 9.6 kb genome encodes for approximately 10 proteins, including the structural capsid and envelope proteins, as well as the nonstructural proteins NS3 (protease and helicase) and NS5B (polymerase). The viral RNA-dependent RNA polymerase (RdRp) is responsible both for generating the intermediate minus-strand RNA template and for the synthesis of progeny positive-strand genomic RNA (Ishii et al., Hepatology, 1227 (1999)). RdRp is used only in the replication of RNA viruses and has very strict template specificities. Thus, RNA-dependent RNA polymerase enzymes, including HCV RdRp, are ideal targets for antiviral drugs.

HCV has been implicated as the major causative agent in non-A, non-B hepatitis (NANBH), particularly in blood-associated NANBH (BB-NANBH) (see, International Patent Application Publication No. WO 89/04669 and European Patent Application Publication No. EP 381 216). NANBH is to be distinguished from other types of viral-induced liver disease, such as hepatitis A virus (HAV), hepatitis B virus (HBV), delta hepatitis virus (HDV), cytomegalovirus (CMV) and Epstein-Barr virus (EBV), as well as from other forms of liver disease such as alcoholism and primary biliary cirrhosis.

HCV has been shown to be capable of establishing a persistent infection and has been implicated in cirrhosis of the liver and in induction of hepatocellular carcinoma. HCV is believed to have infected approximately 3% of the worldwide population. The prognosis for patients suffering from HCV infection is currently poor. HCV infection is more difficult to treat than other forms of hepatitis due to the lack of immunity or remission associated with HCV infection. Current data indicates a less than 50% survival rate at four years post cirrhosis diagnosis. Patients diagnosed with localized resectable hepatocellular carcinoma have a five-year survival rate of 10–30%, whereas those with localized unresectable hepatocellular carcinoma have a five-year survival rate of less than 1%.

Existing therapies for HCV are limited, and only a few inhibitors of HCV RNA-dependent RNA polymerase are known. There is thus a need to identify additional HCV RdRp inhibitors and to identify the structural features required for potent HCV RdRp inhibitory activity.

SUMMARY OF THE INVENTION

1. The present invention provides a novel class of inhibitors of HCV RNA-dependent RNA polymerase (RdRp), pharmaceutical compositions comprising one or more of these inhibitors, and methods of treatment or prevention of HCV or amelioration of one or more of the symptoms of hepatitis C using one or more such compounds or compositions. The present invention discloses compounds having the general structure shown in formula I:

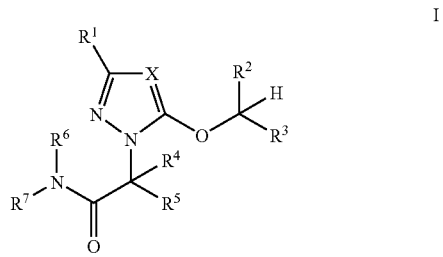

or a pharmaceutically acceptable salt or ester thereof, wherein:

X is $C(R^8)$ or N;

$R^8$ is H, halo, $CF_3$, $C_1$–$C_6$ alkyl, halo($C_1$–$C_6$)alkyl, —OH, —SH, $C_1$–$C_6$ alkoxy, $C_1$–$C_6$ alkylthio, —$NH_2$, —NH($C_1$–$C_6$ alkyl), or —N($C_1$–$C_6$ alkyl)$_2$;

$R^1$ is —$CO_2R^9$, —C(O)$NR^9R^{10}$, —$NR^9SO_2R^{10}$, —CN, —C(O)$NR^9CN$, or unsubstituted or substituted tetrazolyl;

$R^2$ is cycloalkyl, aryl, aralkyl, heteroaryl, heteroaralkyl, alkyl, or cycloalkylalkyl, wherein each member of $R^2$ is optionally substituted with 1–4 $R^{12}$ moieties;

$R^3$ is H or $C_1$–$C_6$ alkyl;

$R^4$ is H, $C_1$–$C_6$ alkyl or $C_1$–$C_6$ alkoxy;

$R^5$ is H, $C_1$–$C_6$ alkyl or $C_1$–$C_6$ alkoxy;

$R^6$ is cycloalkyl, aryl, aralkyl, heteroaryl, heteroaralkyl, alkyl, or cycloalkylalkyl, wherein each member of $R^2$ is optionally substituted with 1–4 $R^{12}$ moieties;

$R^7$ is H or $C_1$–$C_6$ alkyl; or $R^6$ and $R^7$, when attached to the same nitrogen, are optionally taken together with the attached nitrogen to form a five to seven membered ring having 0–1 additional heteroatom selected from N, O or S (in addition to said attached nitrogen), wherein said five to seven membered ring is optionally substituted with 1–3 $R^{18}$ moieties;

each $R^9$ is independently H, alkyl, cycloalkyl, cycloalkylalkyl, heterocyclyl, heterocyclylalkyl, aryl, aralkyl, heteroaryl, or heteroaralkyl, wherein each member except H is optionally substituted with 1–4 $R^{12}$ moieties;

each $R^{10}$ is independently H, alkyl, cycloalkyl, cycloalkylalkyl, heterocyclyl, heterocyclylalkyl, aryl, aralkyl, heteroaryl, or heteroaralkyl, wherein each member except H is optionally substituted with 1–4 $R^{12}$ moieties; or $R^9$ and $R^{10}$ when attached to the same nitrogen are optionally taken together with the attached nitrogen to form a five to sixteen membered monocyclic, bicyclic or tricyclic ring having 0–2 additional heteroatoms (in addition to said attached nitrogen) selected from N, O or S, wherein said monocyclic, bicyclic or tricyclic ring is optionally substituted with 1–3 $R^{18}$ moieties;

each $R^{12}$ is independently halo, alkyl, cycloalkyl, cycloalkylalkyl, heterocyclyl, heterocyclylalkyl, aryl, aralkyl, heteroaryl, heteroaralkyl, —CN, —$CF_3$, —$OR^{13}$, —$SR^{13}$, —C(O)$R^{13}$, —C(S)$R^{13}$, —C(O)$OR^{13}$, —C(S)$OR^{13}$, —OC(O)$R^{13}$, —OC(S)$R^{13}$, —C(O)$NR^{13}R^{14}$, —C(O)$NR^{13}OR^{14}$, —C(S)$NR^{13}OR^{14}$, —C(O)$NR^{13}NR^{13}R^{14}$, —C(S)$NR^{13}NR^{13}R^{14}$, —C(S)$NR^{13}OR^{14}$, —C(O)$SR^{13}$, —$NR^{13}R^{14}$, —$NR^{13}C(O)R^{14}$, —$NR^{13}C(S)$ R$^{14}$, —NR$^{13}$C(O)OR$^{14}$, —NR$^{13}$C(S)OR$^{14}$, —OC(O)NR$^{13}$R$^{14}$, —OC(S)NR$^{13}$R$^{14}$, —NR$^{13}$C(O)NR$^{13}$R$^{14}$, —NR$^{13}$C(S)NR$^{13}$R$^{14}$, —NR$^{13}$C(O)NR$^{13}$OR$^{14}$, —NR$^{13}$C(S)NR$^{13}$OR$^{14}$, —SO$_2$R$^{13}$, —S(O)$_{1-2}$NR$^{13}$R$^{14}$, —N(R$^{13}$)SO$_2$R$^{14}$, —N(R$^{13}$)SO$_2$NR$^{13}$R$^{14}$, —S(O)$_{1-2}$NR$^{13}$OR$^{14}$, —OCF$_3$, —SCF$_3$, haloalkyl, =O, =S, NO$_2$, —C(O)C(O)R$^{13}$, —C(O)CH$_2$C(O)R$^{13}$, methylenedioxy, or ethylenedioxy, wherein each of said alkyl, cycloalkyl, cycloalkylalkyl, heterocyclyl, heterocyclylalkyl, aryl, aralkyl, heteroaryl or heteroaralkyl is optionally substituted with 1–4 R$^{15}$ moieties;

each R$^{13}$ is independently H, alkyl, cycloalkyl, cycloalkylalkyl, heterocyclyl, heterocyclylalkyl, aryl, aralkyl, heteroaryl, or heteroaralkyl, wherein each member of R$^{13}$ except H is optionally substituted with 1–4 R$^{15}$ moieties;

each R$^{14}$ is independently H, alkyl, cycloalkyl, cycloalkylalkyl, heterocyclyl, heterocyclylalkyl, aryl, aralkyl, heteroaryl, or heteroaralkyl, wherein each member of R$^{14}$ except H is optionally substituted with 1–4 R$^{15}$ moieties; or R$^{13}$ and R$^{14}$, when attached to the same nitrogen, are optionally taken together with the attached nitrogen to form a five to seven membered ring having 0–1 additional heteroatom selected from N, O or S (in addition to said attached nitrogen), wherein said five to seven membered ring is optionally substituted with 1–3 R$^{18}$ moieties;

each R$^{15}$ is independently halo, alkyl, cycloalkyl, cycloalkylalkyl, heterocyclyl, heterocyclylalkyl, aryl, aralkyl, heteroaryl, heteroaralkyl, —CN, —CF$_3$, —OR$^{16}$, —SR$^{16}$, —C(O)R$^{16}$, —C(S)R$^{16}$, —C(O)OR$^{16}$, —C(S)OR$^{16}$, —OC(O)R$^{16}$, —OC(S)R$^{16}$, —C(O)NR$^{16}$R$^{17}$, —C(S)NR$^{16}$R$^{17}$, —C(O)NR$^{16}$OR$^{17}$, —C(S)NR$^{16}$OR$^{17}$, —C(O)NR$^{16}$NR$^{16}$R$^{17}$, —C(S)NR$^{16}$NR$^{16}$R$^{17}$, —C(S)NR$^{16}$OR$^{17}$, —C(O)SR$^{16}$, —NR$^{16}$R$^{17}$, —NR$^{16}$C(O)R$^{17}$, —NR$^{16}$C(S)R$^{17}$, —NR$^{16}$C(O)OR$^{17}$, —NR$^{16}$C(S)OR$^{17}$, —OC(O)NR$^{16}$R$^{17}$, —OC(S)NR$^{16}$R$^{17}$, —NR$^{16}$C(O)NR$^{16}$R$^{17}$, —NR$^{16}$C(S)NR$^{16}$R$^{17}$, —NR$^{16}$C(O)NR$^{16}$OR$^{17}$, —NR$^{16}$C(S)NR$^{16}$OR$^{17}$, —SO$_2$R$^{16}$, —S(O)$_{1-2}$NR$^{16}$R$^{17}$, —N(R$^{16}$)SO$_2$R$^{17}$, —S(O)$_{1-2}$NR$^{16}$OR$^{17}$, —OCF$_3$, —SCF$_3$, haloalkyl, =O, =S, NO$_2$, —C(O)C(O)R$^{16}$, —C(O)CH$_2$C(O)R$^{16}$, methylenedioxy, or ethylenedioxy, wherein each of said alkyl, cycloalkyl, cycloalkylalkyl, heterocyclyl, heterocyclylalkyl, aryl, aralkyl, heteroaryl or heteroaralkyl is optionally substituted with 1–3 R$^{18}$ moieties;

each R$^{16}$ is independently H, alkyl, cycloalkyl, cycloalkylalkyl, heterocyclyl, heterocyclylalkyl, aryl, aralkyl, heteroaryl or heteroaralkyl, wherein each member of R$^{16}$ is optionally substituted with 1–3 R$^{18}$;

each R$^{17}$ is independently H, alkyl, cycloalkyl, cycloalkylalkyl, heterocyclyl, heterocyclylalkyl, aryl, aralkyl, heteroaryl or heteroaralkyl, wherein each member of R$^{16}$ is optionally substituted with 1–3 R$^{18}$; or R$^{16}$ and R$^{17}$, when attached to the same nitrogen, are optionally taken together with the attached nitrogen to form a five to seven membered ring having 0–1 additional heteroatom selected from N, O or S (in addition to said attached nitrogen), wherein said five to seven membered ring is optionally substituted with 1–3 R$^{18}$ moieties;

each R$^{18}$ is halo, =O, =S, NO$_2$, alkyl, —OR$^{20}$, —CN, —NR$^{19}$R$^{20}$, —C(O)R$^{20}$, —C(O)OR$^{20}$, —C(O)NR$^{19}$R$^{20}$, —CF$_3$, or —N(R$^{19}$)C(O)R$^{20}$;

each R$^{19}$ is independently H or alkyl; and each R$^{20}$ is independently H or alkyl.

The compounds represented by formula I, alone or in combination with one or more other suitable agents disclosed herein, as well as pharmaceutical compositions composition comprising the same, are useful for treating or preventing HCV infection, HIV infection, AIDS (Acquired Immune Deficiency Syndrome), and related disorders.

DETAILED DESCRIPTION

In one embodiment, the present invention discloses substituted pyrazole and [1,2,4]triazole compounds which are represented by structural formula I or a pharmaceutically acceptable salt or solvate thereof, wherein the various moieties are as described above.

In one embodiment, X is C(R$^8$).

In one embodiment, X is C(R$^8$) and R$^8$ is H.

In another embodiment, X is N.

In another embodiment, R$^3$ is H or CH$_3$ and R$^7$ is H or CH$_3$.

In another embodiment, R$^2$ is alkyl, cycloalkyl, aryl, or heteroaryl, wherein said alkyl, cycloalkyl, aryl, or heteroaryl is optionally substituted with 1–2 R$^{12}$ moieties. In another embodiment, R$^2$ is i-propyl, t-butyl, phenyl, naphthyl, cyclohexyl, pyridyl, or thienyl, wherein said wherein said phenyl, naphthyl, cyclohexyl, pyridyl, or thienyl is optionally substituted with 1–2 R$^{12}$ moieties. In another embodiment, each R$^{12}$ is independently —OR$^{13}$, CF$_3$, halo, alkyl, 5-membered heteroaryl, —C(O)OR$^{20}$, or aryl, wherein said alkyl is optionally substituted with —SO$_2$R$^{16}$ and said aryl is optionally substituted with 1–2 R$^{15}$ moieties; R$^{13}$ is alkyl, aralkyl, or aryl optionally substituted with halo; R$^{15}$ is CF$_3$, SO$_2$R$^{16}$, —OR$^{16}$, —C(O)OR$^{20}$, or halo; and R$^{16}$ is alkyl or aryl. In another embodiment, each R$^{12}$ is independently —O-(phenyl optionally substituted with halo); CF$_3$; halo; C$_1$–C$_4$ alkyl; C$_1$–C$_4$ alkoxy; thienyl; —(CH$_2$)SO$_2$—phenyl; or phenyl optionally substituted with one or two moieties selected from the group consisting of CF$_3$, halo, C$_1$–C$_4$ alkoxy, —SO$_2$CH$_3$, and —CO$_2$H.

In another embodiment, R$^6$ is cycloalkyl, aryl, aralkyl or heteroaryl, wherein said cycloalkyl, aryl, aralkyl or heteroaryl is optionally substituted with 1–2 R$^{12}$ moieties. In another embodiment, R$^6$ is cyclohexyl, phenyl, —(CH$_2$)$_{1-3}$-phenyl, or benzothiazolyl, wherein each member of R$^6$ is optionally substituted with 1–2 R$^{12}$ moieties. In another embodiment, each R$^{12}$ is independently —OR$^{13}$ or —NR$^{19}$R$^{20}$ and R$^{13}$ is aralkyl. In another embodiment, R$^{13}$ is benzyl.

In another embodiment, R$^1$ is —C(O)OR$^{20}$ or unsubstituted tetrazolyl. In another embodiment, R$^1$ is —C(O)OH or unsubstituted tetrazolyl.

In another embodiment, the present invention provides compounds of formula II:

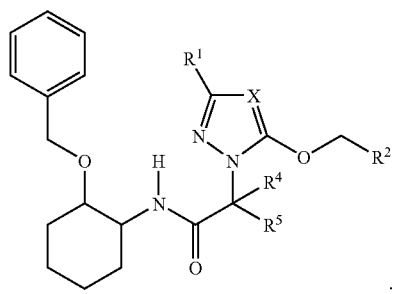

II

In another embodiment, the present invention provides compounds of formula II, wherein R$^2$ is aryl or heteroaryl, wherein said aryl or heteroaryl is optionally substituted with 1–2 R[12] moieties. In another embodiment, the present invention provides compounds of formula II, wherein said aryl or heteroaryl of R[2] is substituted with 1–2 R[12] moieties and one of the R[12] moieties is at the ortho-position.

In another embodiment, the present invention provides compounds of formula II-a:

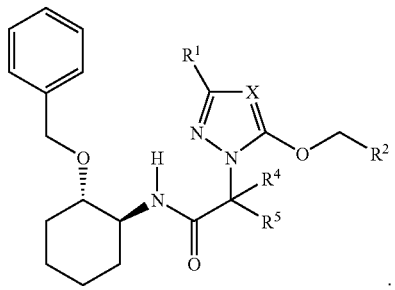

II-a

In another embodiment, the present invention provides compounds of formula III:

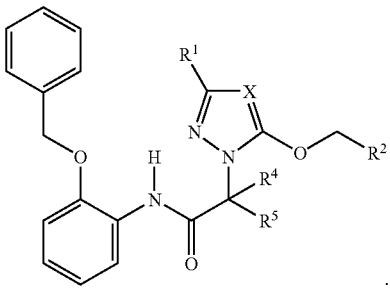

III

In another embodiment, the present invention provides compounds of formula III, wherein R[2] is aryl or heteroaryl, wherein said aryl or heteroaryl is optionally substituted with 1–2 R[12] moieties. In another embodiment, the present invention provides compounds of formula III, wherein said aryl or heteroaryl of R[2] is substituted with 1–2 R[12] moieties and one of the R[12] moieties is at the ortho-position.

Representative compounds of the present invention are shown in Table 1 below.

TABLE 1

| Cpd | Structure | Cpd | Structure |
|---|---|---|---|
| 1 | 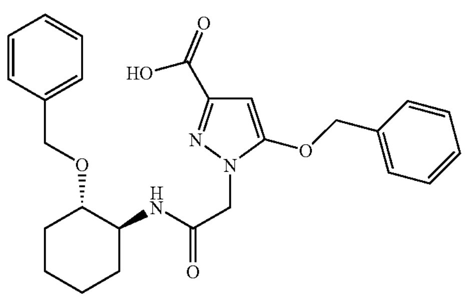 | 2 | 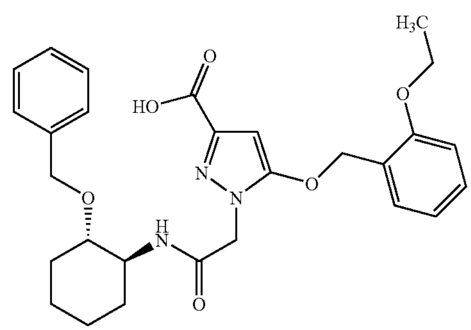 |
| 3 | 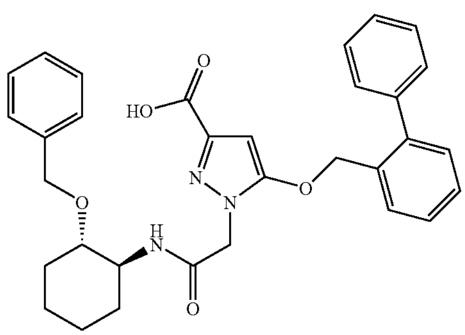 | 4 | 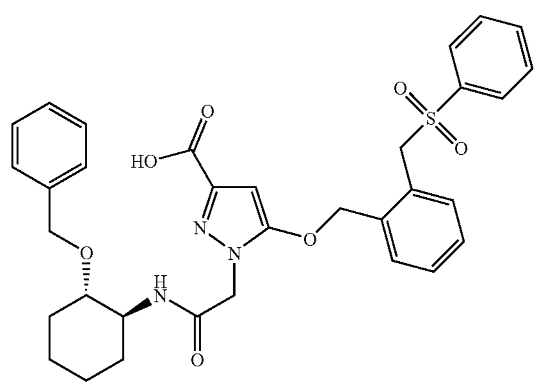 |

TABLE 1-continued

| Cpd | Structure | Cpd | Structure |
|---|---|---|---|
| 5 | 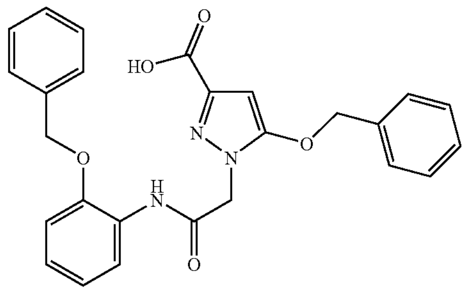 | 6 | 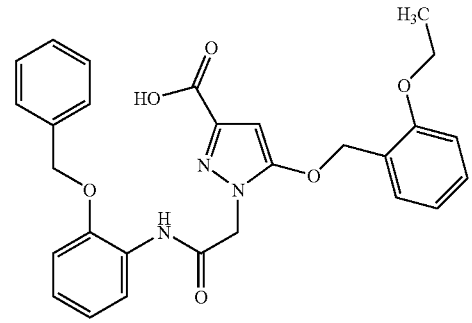 |
| 7 | 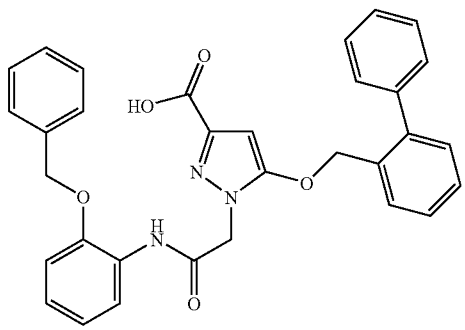 | 8 | 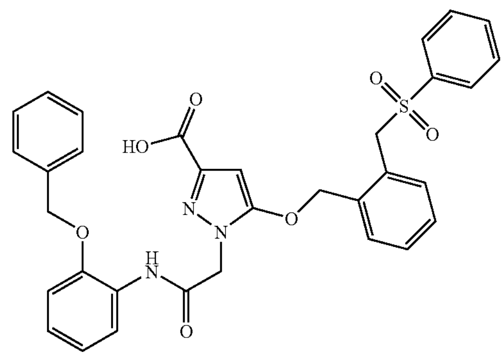 |
| 9 | 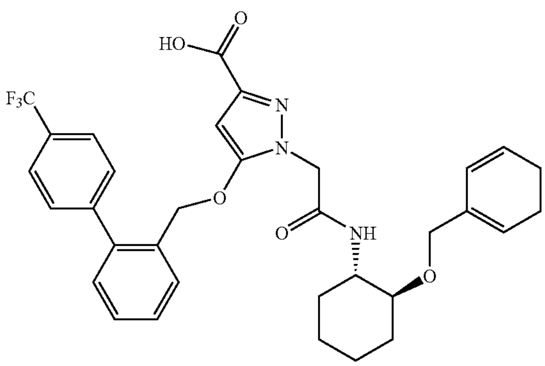 | 10 | 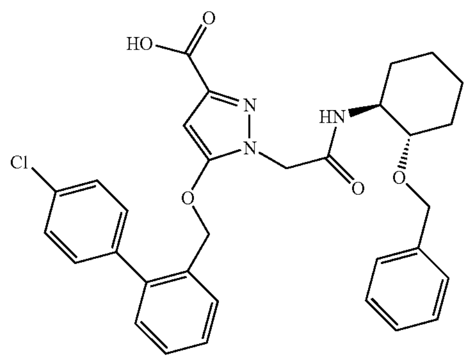 |
| 11 | 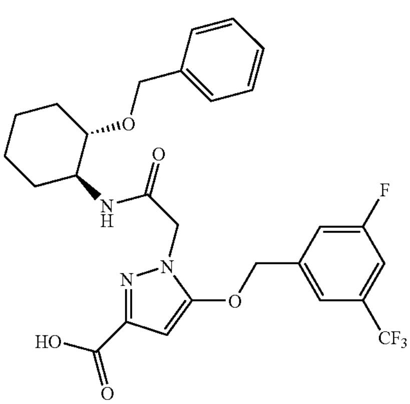 | 12 | 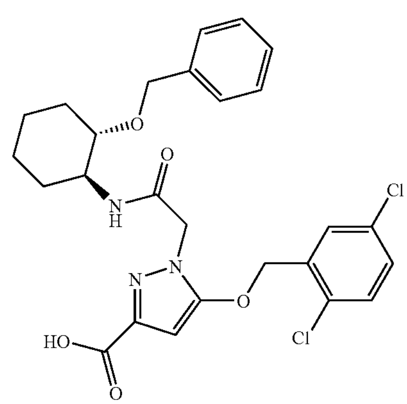 |

TABLE 1-continued

| Cpd | Structure | Cpd | Structure |
|-----|-----------|-----|-----------|
| 13 | 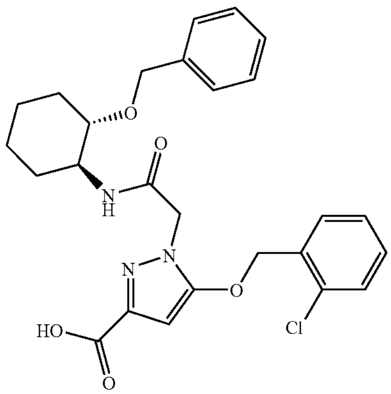 | 14 | 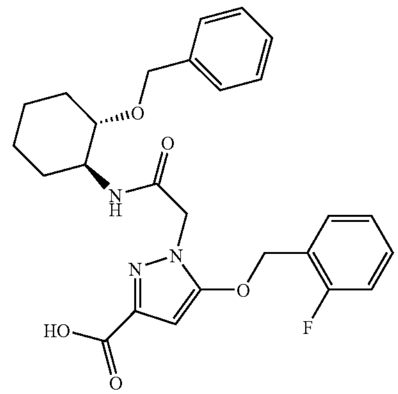 |
| 15 | 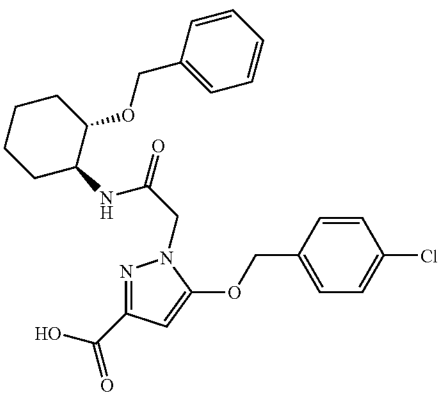 | 16 | 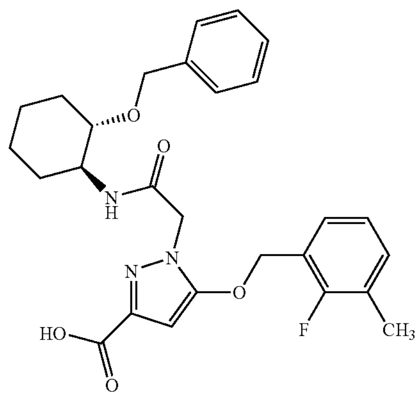 |
| 17 | 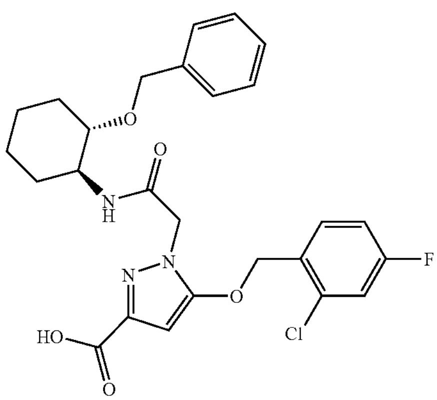 | 18 | 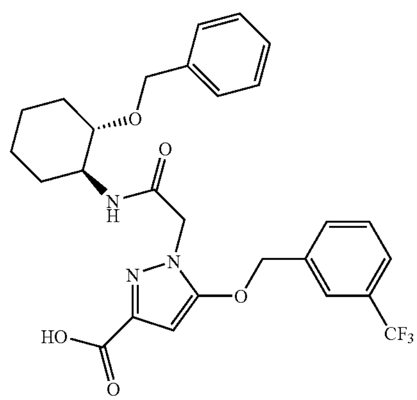 |
| 19 | 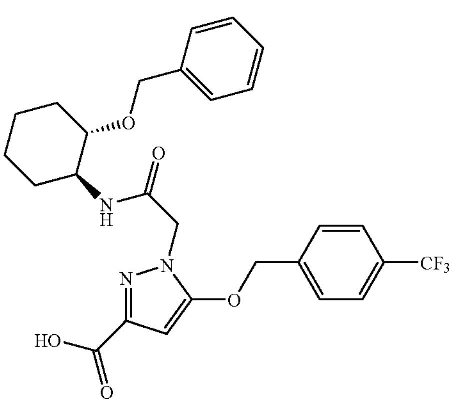 | 20 | 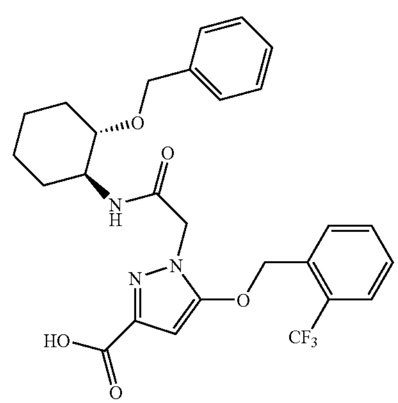 |

TABLE 1-continued

| Cpd | Structure | Cpd | Structure |
|-----|-----------|-----|-----------|
| 21 | 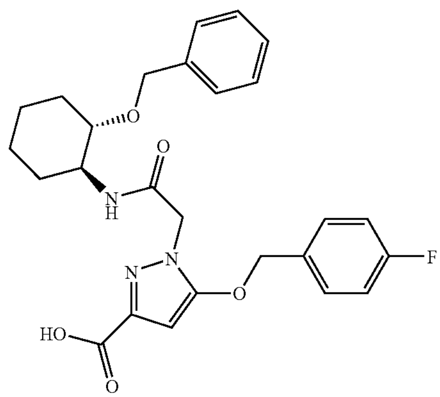 | 22 | 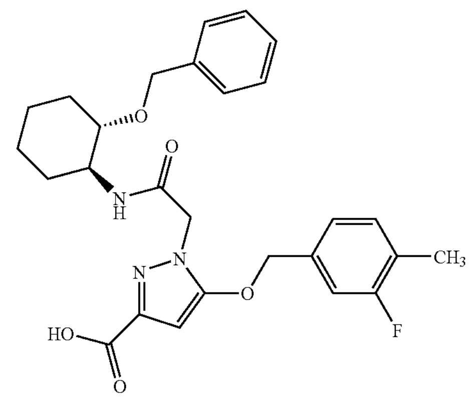 |
| 23 | 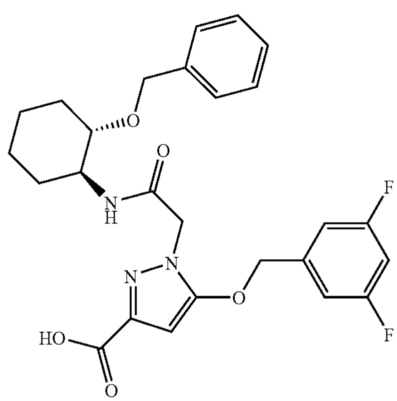 | 24 | 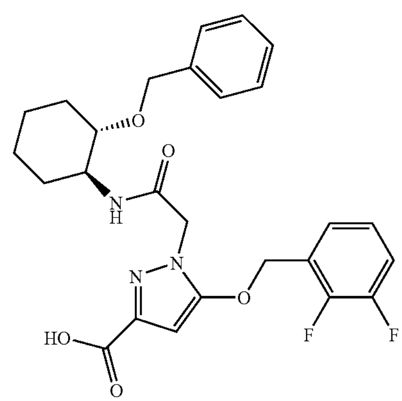 |
| 25 | 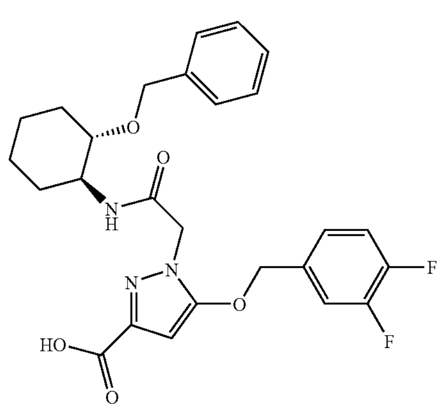 | 26 | 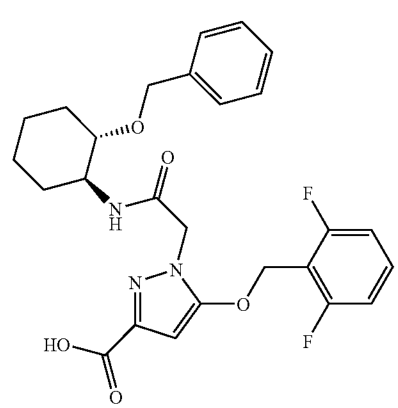 |

TABLE 1-continued

| Cpd | Structure | Cpd | Structure |
|-----|-----------|-----|-----------|
| 27  | 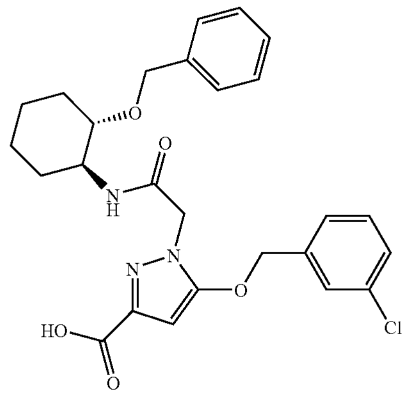          | 28  | 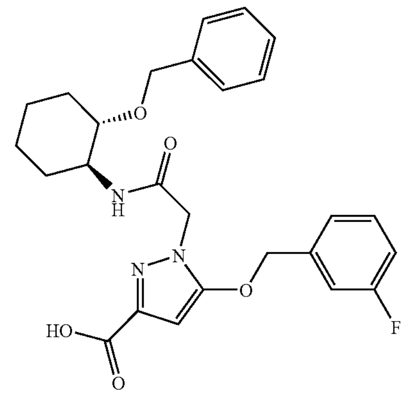          |
| 29  | 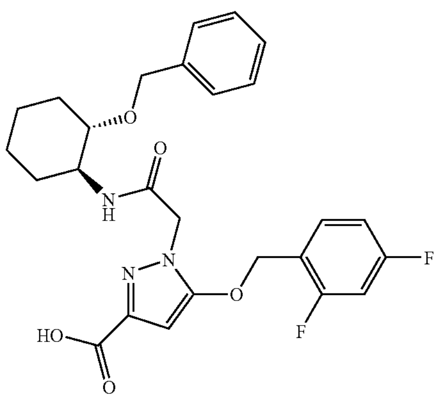          | 30  | 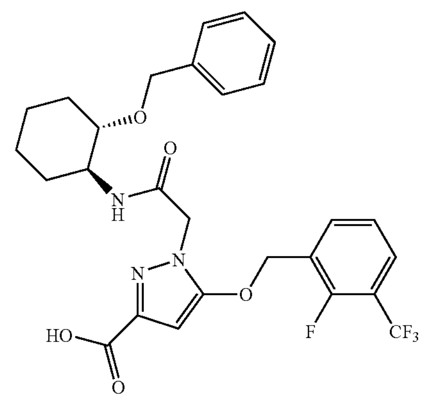          |
| 31  | 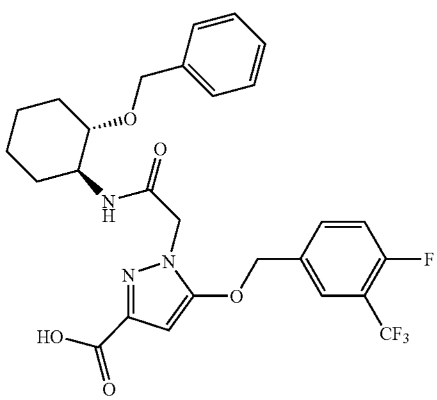          | 32  | 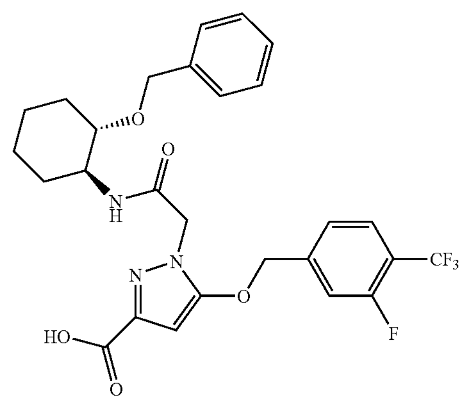          |
| 33  | 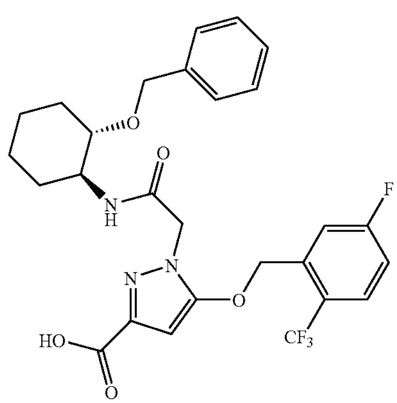          | 34  | 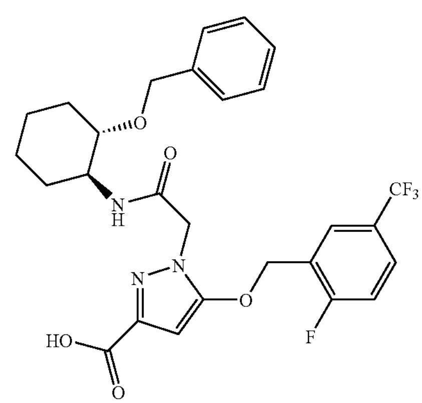          |

TABLE 1-continued

| Cpd | Structure | Cpd | Structure |
| --- | --- | --- | --- |
| 35 | 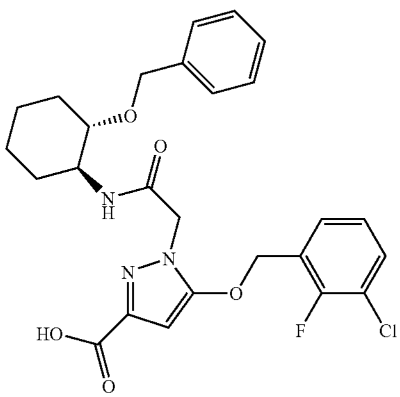 | 36 | 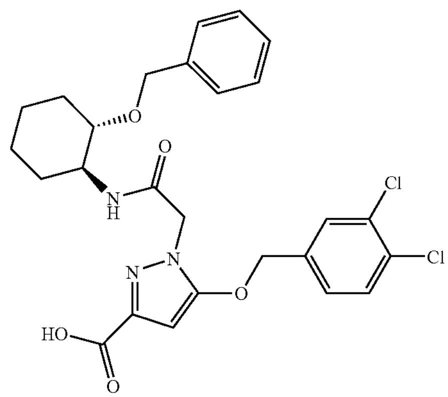 |
| 37 | 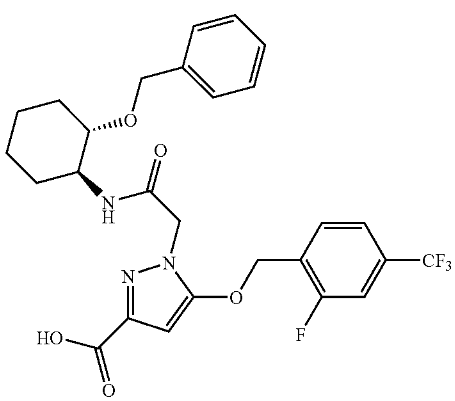 | 38 | 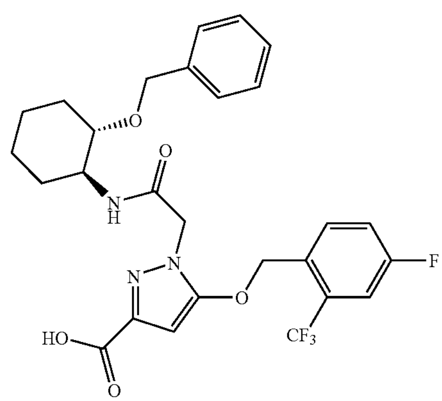 |
| 39 | 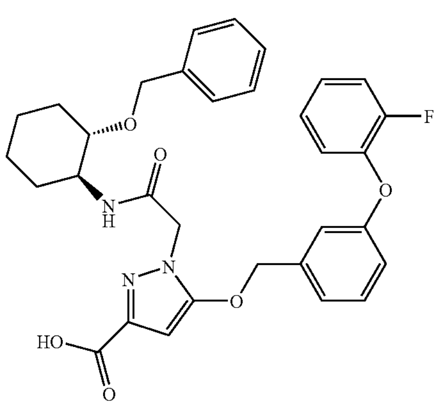 | 40 | 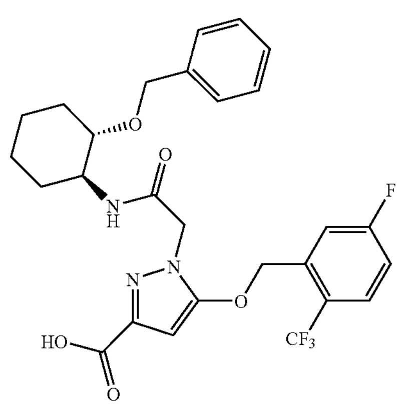 |

TABLE 1-continued

| Cpd | Structure | Cpd | Structure |
|---|---|---|---|
| 41 | 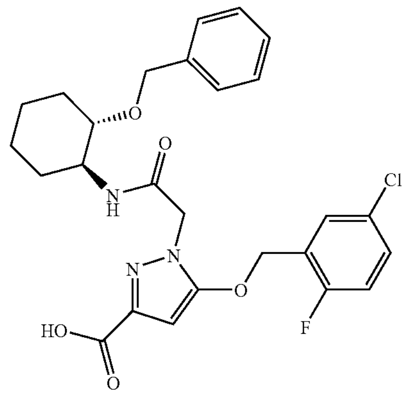 | 42 | 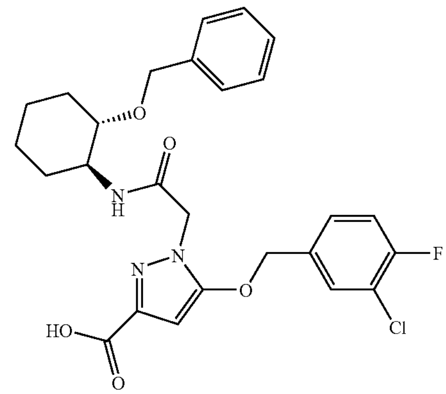 |
| 43 | 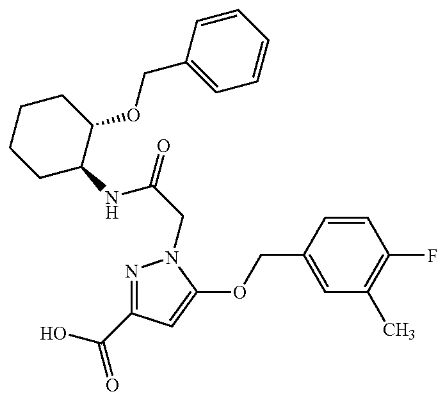 | 44 | 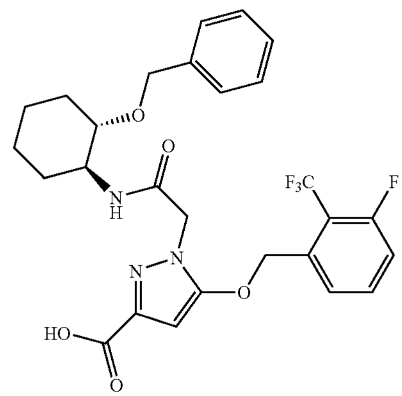 |
| 45 | 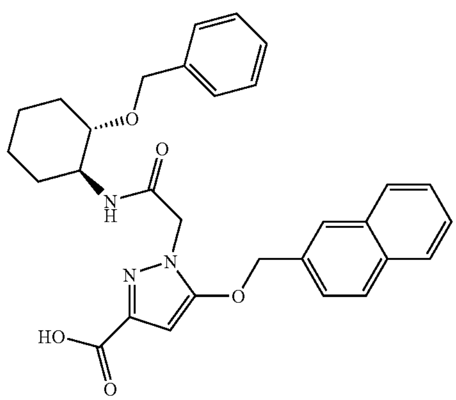 | 46 | 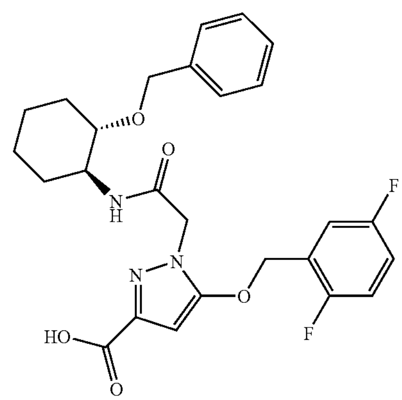 |
| 47 | 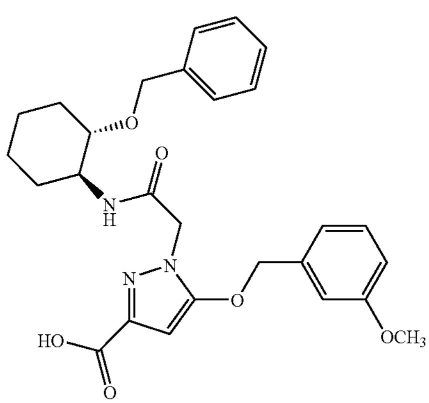 | 48 | 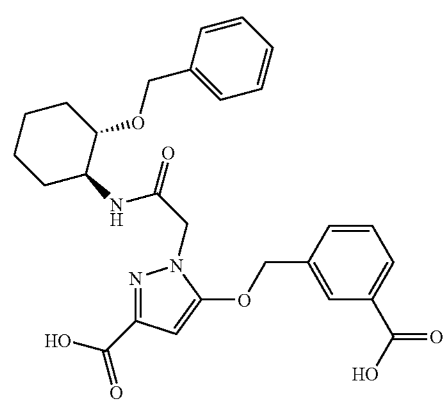 |

TABLE 1-continued

| Cpd | Structure | Cpd | Structure |
|-----|-----------|-----|-----------|
| 49  | 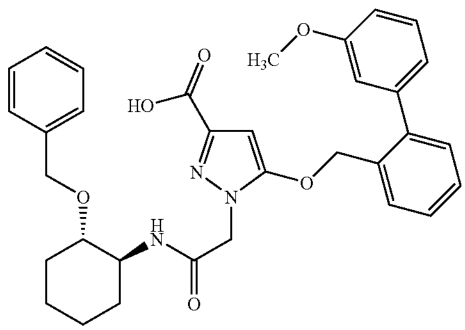          | 50  | 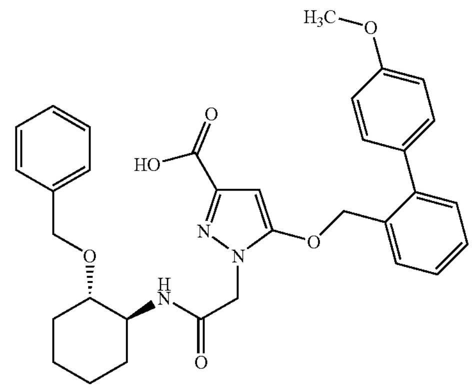          |
| 51  | 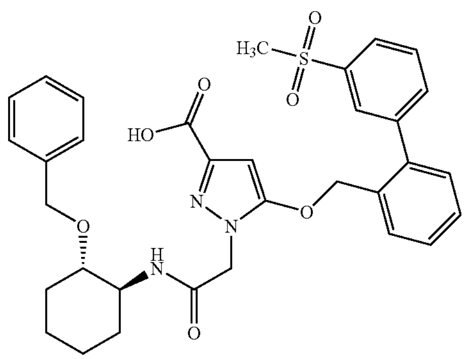          | 52  | 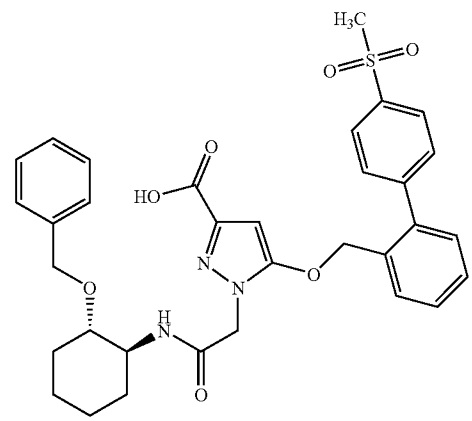          |
| 53  | 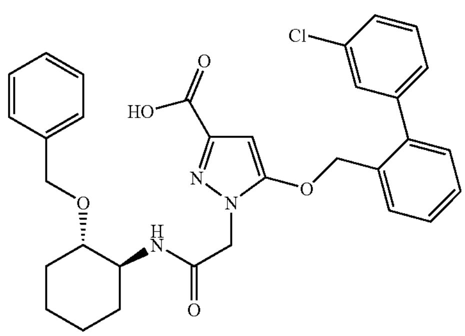          | 54  | 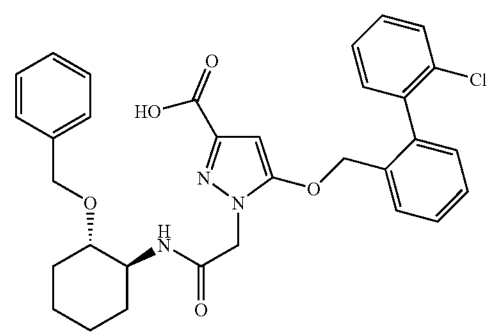          |
| 55  | 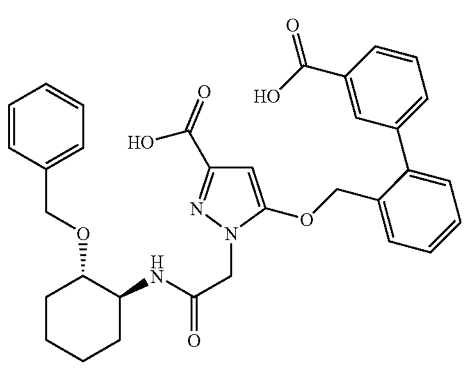          | 56  | 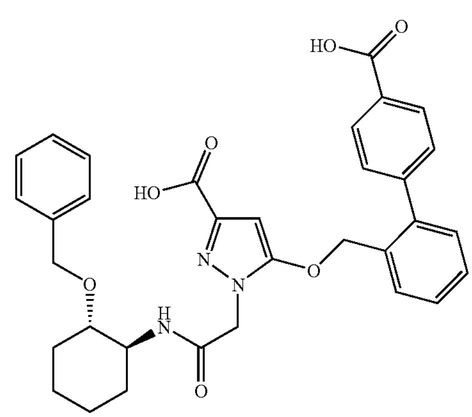          |

TABLE 1-continued

| Cpd | Structure | Cpd | Structure |
|---|---|---|---|
| 57 | 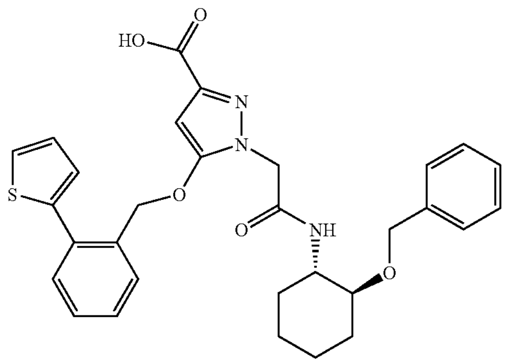 | 58 | 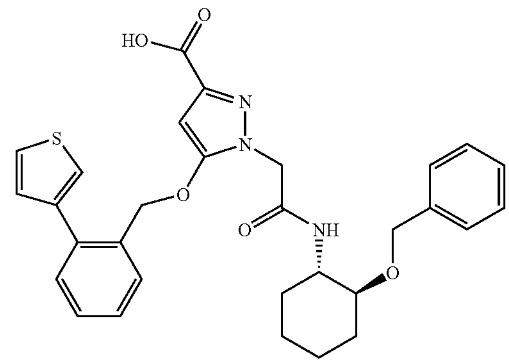 |
| 59 | 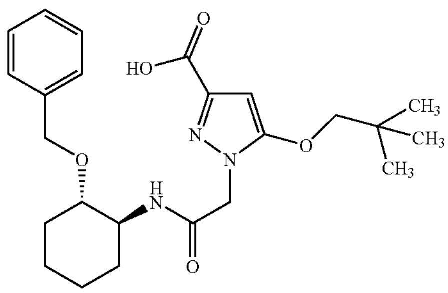 | 60 | 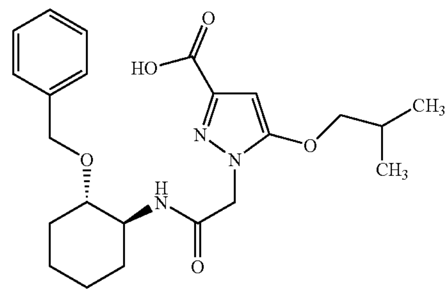 |
| 61 | 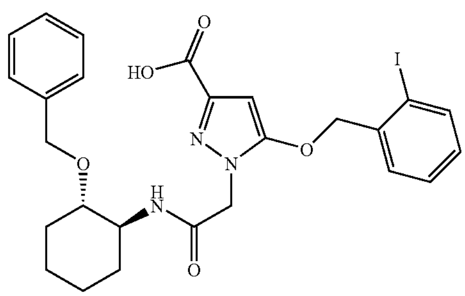 | 62 | 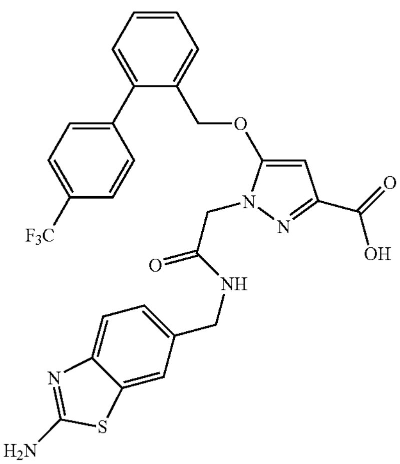 |
| 63 | 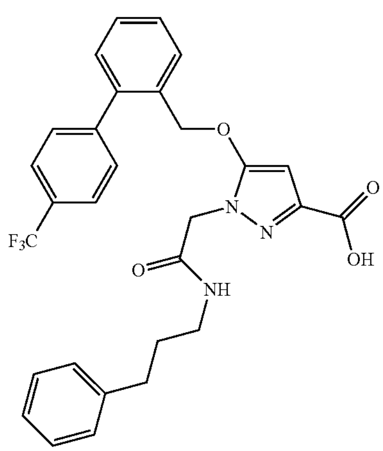 | 64 | 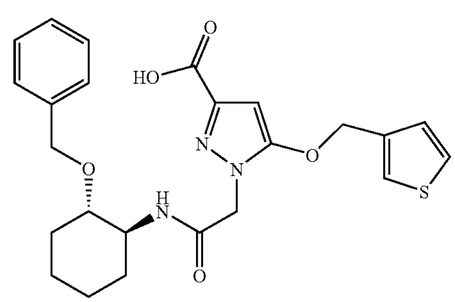 |

TABLE 1-continued

| Cpd | Structure | Cpd | Structure |
|---|---|---|---|
| 65 | 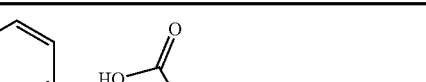 | 66 | 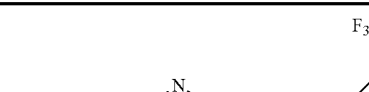 |

Preferred compounds include compounds 9, 10, 19, 32, 36, 50, 53, 58 and 66.

As used above, and throughout this disclosure, the following terms, unless otherwise indicated, shall be understood to have the following meanings:

"Patient" includes both human and animals.

"Mammal" means humans and other mammalian animals.

"Alkyl" means an aliphatic hydrocarbon group which may be straight or branched and comprising about 1 to about 20 carbon atoms in the chain. Preferred alkyl groups contain about 1 to about 12 carbon atoms in the chain. More preferred alkyl groups contain about 1 to about 6 carbon atoms in the chain. Branched means that one or more lower alkyl groups such as methyl, ethyl or propyl, are attached to a linear alkyl chain. "Lower alkyl" means a group having about 1 to about 6 carbon atoms in the chain which may be straight or branched. "Alkyl" may be unsubstituted or optionally substituted by one or more substituents which may be the same or different, each substituent being independently selected from the group consisting of halo, alkyl, aryl, cycloalkyl, cyano, hydroxy, alkoxy, alkylthio, amino, —NH(alkyl), —NH(cycloalkyl), —N(alkyl)$_2$, carboxy and —C(O)O-alkyl. Non-limiting examples of suitable alkyl groups include methyl, ethyl, n-propyl, isopropyl and t-butyl.

"Alkenyl" means an aliphatic hydrocarbon group containing at least one carbon-carbon double bond and which may be straight or branched and comprising about 2 to about 15 carbon atoms in the chain. Preferred alkenyl groups have about 2 to about 12 carbon atoms in the chain; and more preferably about 2 to about 6 carbon atoms in the chain. Branched means that one or more lower alkyl groups such as methyl, ethyl or propyl, are attached to a linear alkenyl chain. "Lower alkenyl" means about 2 to about 6 carbon atoms in the chain which may be straight or branched. "Alkenyl" may be unsubstituted or optionally substituted by one or more substituents which may be the same or different, each substituent being independently selected from the group consisting of halo, alkyl, aryl, cycloalkyl, cyano, alkoxy and —S(alkyl). Non-limiting examples of suitable alkenyl groups include ethenyl, propenyl, n-butenyl, 3-methylbut-2-enyl, n-pentenyl, octenyl and decenyl.

"Alkylene" means a difunctional group obtained by removal of a hydrogen atom from an alkyl group that is defined above. Non-limiting examples of alkylene include methylene, ethylene and propylene.

"Alkynyl" means an aliphatic hydrocarbon group containing at least one carbon-carbon triple bond and which may be straight or branched and comprising about 2 to about 15 carbon atoms in the chain. Preferred alkynyl groups have about 2 to about 12 carbon atoms in the chain; and more preferably about 2 to about 4 carbon atoms in the chain. Branched means that one or more lower alkyl groups such as methyl, ethyl or propyl, are attached to a linear alkynyl chain. "Lower alkynyl" means about 2 to about 6 carbon atoms in the chain which may be straight or branched. Non-limiting examples of suitable alkynyl groups include ethynyl, propynyl, 2-butynyl and 3-methylbutynyl. "Alkynyl" may be unsubstituted or optionally substituted by one or more substituents which may be the same or different, each substituent being independently selected from the group consisting of alkyl, aryl and cycloalkyl.

"Aryl" means an aromatic monocyclic or multicyclic ring system comprising about 6 to about 14 carbon atoms, preferably about 6 to about 10 carbon atoms. The aryl group can be optionally substituted with one or more "ring system substituents" which may be the same or different, and are as defined herein. Non-limiting examples of suitable aryl groups include phenyl and naphthyl.

"Heteroaryl" means an aromatic monocyclic or multicyclic ring system comprising about 5 to about 14 ring atoms, preferably about 5 to about 10 ring atoms, in which one or more of the ring atoms is an element other than carbon, for example nitrogen, oxygen or sulfur, alone or in combination. Preferred heteroaryls contain about 5 to about 6 ring atoms. The "heteroaryl" can be optionally substituted by one or more "ring system substituents" which may be the same or different, and are as defined herein. The prefix aza, oxa or thia before the heteroaryl root name means that at least a nitrogen, oxygen or sulfur atom respectively, is present as a ring atom. A nitrogen atom of a heteroaryl can be optionally oxidized to the corresponding N-oxide. Non-limiting examples of suitable heteroaryls include pyridyl, pyrazinyl, furanyl, thienyl, pyrimidinyl, pyridone (including N-substituted pyridones), isoxazolyl, isothiazolyl, oxazolyl, thiazolyl, pyrazolyl, furazanyl, pyrrolyl, pyrazolyl, triazolyl, 1,2,4-thiadiazolyl, pyrazinyl, pyridazinyl, quinoxalinyl, phthalazinyl, oxindolyl, imidazo[1,2-a]pyridinyl, imidazo[2,1-b]thiazolyl, benzofurazanyl, indolyl, azaindolyl, benzimidazolyl, benzothienyl, quinolinyl, imidazolyl, thienopyridyl, quinazolinyl, thienopyrimidyl, pyrrolopyridyl, imidazopyridyl, isoquinolinyl, benzoazaindolyl, 1,2,4-triazinyl, benzothiazolyl and the like. The term "heteroaryl" also refers to partially saturated heteroaryl moieties such as, for example, tetrahydroisoquinolyl, tetrahydroquinolyl and the like.

"Aralkyl" or "arylalkyl" means an aryl-alkyl-group in which the aryl and alkyl are as previously described. Preferred aralkyls comprise a lower alkyl group. Non-limiting examples of suitable aralkyl groups include benzyl, 2-phenethyl and naphthalenylmethyl. The bond to the parent moiety is through the alkyl.

"Alkylaryl" means an alkyl-aryl-group in which the alkyl and aryl are as previously described. Preferred alkylaryls comprise a lower alkyl group. Non-limiting example of a suitable alkylaryl group is tolyl. The bond to the parent moiety is through the aryl.

"Cycloalkyl" means a non-aromatic mono- or multicyclic ring system comprising about 3 to about 10 carbon atoms, preferably about 5 to about 10 carbon atoms. Preferred cycloalkyl rings contain about 5 to about 7 ring atoms. The cycloalkyl can be optionally substituted with one or more "ring system substituents" which may be the same or different, and are as defined above. Non-limiting examples of suitable monocyclic cycloalkyls include cyclopropyl, cyclopentyl, cyclohexyl, cycloheptyl and the like. Non-limiting examples of suitable multicyclic cycloalkyls include 1-decalinyl, norbornyl, adamantyl and the like.

"Cycloalkylalkyl" means a cycloalkyl moiety as defined above linked via an alkyl moiety (defined above) to a parent core. Non-limiting examples of suitable cycloalkylalkyls include cyclohexylmethyl, adamantylmethyl and the like.

"Cycloalkenyl" means a non-aromatic mono or multicyclic ring system comprising about 3 to about 10 carbon atoms, preferably about 5 to about 10 carbon atoms which contains at least one carbon-carbon double bond. Preferred cycloalkenyl rings contain about 5 to about 7 ring atoms. The cycloalkenyl can be optionally substituted with one or more "ring system substituents" which may be the same or different, and are as defined above. Non-limiting examples of suitable monocyclic cycloalkenyls include cyclopentenyl, cyclohexenyl, cyclohepta-1,3-dienyl, and the like. Non-limiting example of a suitable multicyclic cycloalkenyl is norbornylenyl.

"Cycloalkenylalkyl" means a cycloalkenyl moiety as defined above linked via an alkyl moiety (defined above) to a parent core. Non-limiting examples of suitable cycloalkenylalkyls include cyclopentenylmethyl, cyclohexenylmethyl and the like.

"Halogen" means fluorine, chlorine, bromine, or iodine. Preferred are fluorine, chlorine and bromine.

"Ring system substituent" means a substituent attached to an aromatic or non-aromatic ring system which, for example, replaces an available hydrogen on the ring system. Ring system substituents may be the same or different, each being independently selected from the group consisting of alkyl, alkenyl, alkynyl, aryl, heteroaryl, aralkyl, alkylaryl, heteroaralkyl, heteroarylalkenyl, heteroarylalkynyl, alkylheteroaryl, hydroxy, hydroxyalkyl, alkoxy, aryloxy, aralkoxy, acyl, aroyl, halo, nitro, cyano, carboxy, alkoxycarbonyl, aryloxycarbonyl, aralkoxycarbonyl, alkylsulfonyl, arylsulfonyl, heteroarylsulfonyl, alkylthio, arylthio, heteroarylthio, aralkylthio, heteroaralkylthio, cycloalkyl, heterocyclyl, —C(=N—CN)—NH$_2$, —C(=NH)—NH$_2$, —C(=NH)—NH(alkyl), Y$_1$Y$_2$N—, Y$_1$Y$_2$N-alkyl-, Y$_1$Y$_2$NC(O)—, Y$_1$Y$_2$NSO$_2$— and —SO$_2$NY$_1$Y$_2$, wherein Y$_1$ and Y$_2$ can be the same or different and are independently selected from the group consisting of hydrogen, alkyl, aryl, cycloalkyl, and aralkyl. "Ring system substituent" may also mean a single moiety which simultaneously replaces two available hydrogens on two adjacent carbon atoms (one H on each carbon) on a ring system. Examples of such moiety are methylene dioxy, ethylenedioxy, —C(CH$_3$)$_2$— and the like which form moieties such as, for example:

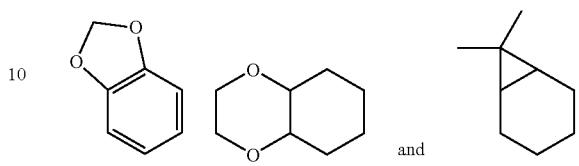

"Heteroarylalkyl" means a heteroaryl moiety as defined above linked via an alkyl moiety (defined above) to a parent core. Non-limiting examples of suitable heteroaryls include 2-pyridinylmethyl, quinolinylmethyl and the like.

"Heterocyclyl" means a non-aromatic saturated monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur, alone or in combination. There are no adjacent oxygen and/or sulfur atoms present in the ring system. Preferred heterocyclyls contain about 5 to about 6 ring atoms. The prefix aza, oxa or thia before the heterocyclyl root name means that at least a nitrogen, oxygen or sulfur atom respectively is present as a ring atom. Any —NH in a heterocyclyl ring may exist protected such as, for example, as an —N(Boc), —N(CBz), —N(Tos) group and the like; such protections are also considered part of this invention. The heterocyclyl can be optionally substituted by one or more "ring system substituents" which may be the same or different, and are as defined herein. The nitrogen or sulfur atom of the heterocyclyl can be optionally oxidized to the corresponding N-oxide, S-oxide or S,S-dioxide. Non-limiting examples of suitable monocyclic heterocyclyl rings include piperidyl, pyrrolidinyl, piperazinyl, morpholinyl, thiomorpholinyl, thiazolidinyl, 1,4-dioxanyl, tetrahydrofuranyl, tetrahydrothiophenyl, lactam, lactone, and the like. "Heterocyclyl" may also mean a single moiety (e.g., carbonyl) which simultaneously replaces two available hydrogens on the same carbon atom on a ring system. Example of such moiety is pyrrolidone:

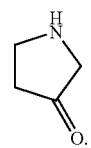

"Heterocyclylalkyl" means a heterocyclyl moiety as defined above linked via an alkyl moiety (defined above) to a parent core. Non-limiting examples of suitable heterocyclylalkyls include piperidinylmethyl, piperazinylmethyl and the like.

"Heterocyclenyl" means a non-aromatic monocyclic or multicyclic ring system comprising about 3 to about 10 ring atoms, preferably about 5 to about 10 ring atoms, in which one or more of the atoms in the ring system is an element other than carbon, for example nitrogen, oxygen or sulfur atom, alone or in combination, and which contains at least one carbon-carbon double bond or carbon-nitrogen double bond. There are no adjacent oxygen and/or sulfur atoms present in the ring system. Preferred heterocyclenyl rings contain about 5 to about 6 ring atoms. The prefix aza, oxa or thia before the heterocyclenyl root name means that at least a nitrogen, oxygen or sulfur atom respectively is present as a ring atom. The heterocyclenyl can be optionally substituted by one or more ring system substituents, wherein "ring system substituent" is as defined above. The nitrogen or sulfur atom of the heterocyclenyl can be optionally oxidized to the corresponding N-oxide, S-oxide or S,S-dioxide. Non-limiting examples of suitable heterocyclenyl groups include 1,2,3,4-tetrahydropyridine, 1,2-dihydropyridyl, 1,4-dihydropyridyl, 1,2,3,6-tetrahydropyridine, 1,4,5,6-tetrahydropyrimidine, 2-pyrrolinyl, 3-pyrrolinyl, 2-imidazolinyl, 2-pyrazolinyl, dihydroimidazole, dihydrooxazole, dihydrooxadiazole, dihydrothiazole, 3,4-dihydro-2H-pyran, dihydrofuranyl, fluorodihydrofuranyl, 7-oxabicyclo[2.2.1]heptenyl, dihydrothiophenyl, dihydrothiopyranyl, and the like. "Heterocyclenyl" may also mean a single moiety (e.g., carbonyl) which simultaneously replaces two available hydrogens on the same carbon atom on a ring system. Example of such moiety is pyrrolidinone:

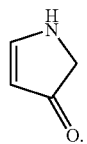

"Heterocyclenylalkyl" means a heterocyclenyl moiety as defined above linked via an alkyl moiety (defined above) to a parent core.

It should be noted that in hetero-atom containing ring systems of this invention, there are no hydroxyl groups on carbon atoms adjacent to a N, O or S, as well as there are no N or S groups on carbon adjacent to another heteroatom. Thus, for example, in the ring:

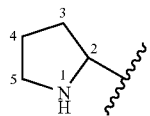

there is no —OH attached directly to carbons marked 2 and 5.

It should also be noted that tautomeric forms such as, for example, the moieties:

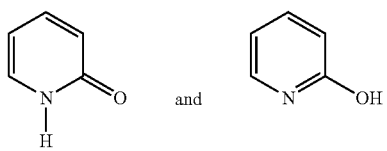

are considered equivalent in certain embodiments of this invention.

"Alkynylalkyl" means an alkynyl-alkyl-group in which the alkynyl and alkyl are as previously described. Preferred alkynylalkyls contain a lower alkynyl and a lower alkyl group. The bond to the parent moiety is through the alkyl. Non-limiting examples of suitable alkynylalkyl groups include propargylmethyl.

"Heteroaralkyl" means a heteroaryl-alkyl-group in which the heteroaryl and alkyl are as previously described. Preferred heteroaralkyls contain a lower alkyl group. Non-limiting examples of suitable aralkyl groups include pyridylmethyl, and quinolin-3-ylmethyl. The bond to the parent moiety is through the alkyl.

"Hydroxyalkyl" means a HO-alkyl-group in which alkyl is as previously defined. Preferred hydroxyalkyls contain lower alkyl. Non-limiting examples of suitable hydroxyalkyl groups include hydroxymethyl and 2-hydroxyethyl.

"Acyl" means an H—C(O)—, alkyl-C(O)— or cycloalkyl-C(O)—, group in which the various groups are as previously described. The bond to the parent moiety is through the carbonyl. Preferred acyls contain a lower alkyl. Non-limiting examples of suitable acyl groups include formyl, acetyl and propanoyl.

"Aroyl" means an aryl-C(O)— group in which the aryl group is as previously described. The bond to the parent moiety is through the carbonyl. Non-limiting examples of suitable groups include benzoyl and 1-naphthoyl.

"Alkoxy" means an alkyl-O— group in which the alkyl group is as previously described. Non-limiting examples of suitable alkoxy groups include methoxy, ethoxy, n-propoxy, isopropoxy and n-butoxy. The bond to the parent moiety is through the ether oxygen.

"Aryloxy" means an aryl-O— group in which the aryl group is as previously described. Non-limiting examples of suitable aryloxy groups include phenoxy and naphthoxy. The bond to the parent moiety is through the ether oxygen.

"Aralkyloxy" means an aralkyl-O— group in which the aralkyl group is as previously described. Non-limiting examples of suitable aralkyloxy groups include benzyloxy and 1- or 2-naphthalenemethoxy. The bond to the parent moiety is through the ether oxygen.

"Alkylthio" means an alkyl-S— group in which the alkyl group is as previously described. Non-limiting examples of suitable alkylthio groups include methylthio and ethylthio. The bond to the parent moiety is through the sulfur.

"Arylthio" means an aryl-S— group in which the aryl group is as previously described. Non-limiting examples of suitable arylthio groups include phenylthio and naphthylthio. The bond to the parent moiety is through the sulfur.

"Aralkylthio" means an aralkyl-S— group in which the aralkyl group is as previously described. Non-limiting example of a suitable aralkylthio group is benzylthio. The bond to the parent moiety is through the sulfur.

"Alkoxycarbonyl" means an alkyl-O—CO— group. Non-limiting examples of suitable alkoxycarbonyl groups include methoxycarbonyl and ethoxycarbonyl. The bond to the parent moiety is through the carbonyl.

"Aryloxycarbonyl" means an aryl-O—C(O)— group. Non-limiting examples of suitable aryloxycarbonyl groups include phenoxycarbonyl and naphthoxycarbonyl. The bond to the parent moiety is through the carbonyl.

"Aralkoxycarbonyl" means an aralkyl-O—C(O)— group. Non-limiting example of a suitable aralkoxycarbonyl group is benzyloxycarbonyl. The bond to the parent moiety is through the carbonyl.

"Alkylsulfonyl" means an alkyl-S($O_2$)— group. Preferred groups are those in which the alkyl group is lower alkyl. The bond to the parent moiety is through the sulfonyl.

"Arylsulfonyl" means an aryl-S($O_2$)— group. The bond to the parent moiety is through the sulfonyl.

The term "substituted" means that one or more hydrogens on the designated atom is replaced with a selection from the indicated group, provided that the designated atom's normal valency under the existing circumstances is not exceeded, and that the substitution results in a stable compound. Combinations of substituents and/or variables are permissible only if such combinations result in stable compounds. By "stable compound" or "stable structure" is meant a compound that is sufficiently robust to survive isolation to a useful degree of purity from a reaction mixture, and formulation into an efficacious therapeutic agent.

The term "optionally substituted" means optional substitution with the specified groups, radicals or moieties.

The term "purified", "in purified form" or "in isolated and purified form" for a compound refers to the physical state of said compound after being isolated from a synthetic process or natural source or combination thereof. Thus, the term "purified", "in purified form" or "in isolated and purified form" for a compound refers to the physical state of said compound after being obtained from a purification process or processes described herein or well known to the skilled artisan, in sufficient purity to be characterizable by standard analytical techniques described herein or well known to the skilled artisan.

It should also be noted that any carbon as well as heteroatom with unsatisfied valences in the text, schemes, examples and Tables herein is assumed to have the sufficient number of hydrogen atom(s) to satisfy the valences.

When a functional group in a compound is termed "protected", this means that the group is in modified form to preclude undesired side reactions at the protected site when the compound is subjected to a reaction. Suitable protecting groups will be recognized by those with ordinary skill in the art as well as by reference to standard textbooks such as, for example, T. W. Greene et al, *Protective Groups in organic Synthesis* (1991), Wiley, New York.

When any variable (e.g., aryl, heterocycle, $R^2$, etc.) occurs more than one time in any constituent or in Formula I, its definition on each occurrence is independent of its definition at every other occurrence.

As used herein, the term "composition" is intended to encompass a product comprising the specified ingredients in the specified amounts, as well as any product which results, directly or indirectly, from combination of the specified ingredients in the specified amounts.

Prodrugs and solvates of the compounds of the invention are also contemplated herein. A discussion of prodrugs is provided in T. Higuchi and V. Stella, *Pro-drugs as Novel Delivery Systems* (1987) 14 of the A.C.S. Symposium Series, and in *Bioreversible Carriers in Drug Design*, (1987) Edward B. Roche, ed., American Pharmaceutical Association and Pergamon Press. The term "prodrug" means a compound (e.g, a drug precursor) that is transformed in vivo to yield a compound of Formula (I) or a pharmaceutically acceptable salt, hydrate or solvate of the compound. The transformation may occur by various mechanisms (e.g., by metabolic or chemical processes), such as, for example, through hydrolysis in blood. A discussion of the use of prodrugs is provided by T. Higuchi and W. Stella, "Prodrugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of Formula (I) or a pharmaceutically acceptable salt, hydrate or solvate of the compound contains a carboxylic acid functional group, a prodrug can comprise an ester formed by the replacement of the hydrogen atom of the acid group with a group such as, for example, $(C_1-C_8)$alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino) ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl, and the like.

Similarly, if a compound of Formula (I) contains an alcohol functional group, a prodrug can be formed by the replacement of the hydrogen atom of the alcohol group with a group such as, for example, $(C_1-C_6)$alkanoyloxymethyl, 1-($(C_1-C_6)$alkanoyloxy)ethyl, 1-methyl-1-($(C_1-C_6)$alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino$(C_1-C_4)$alkanyl, arylacyl and α-aminoacyl, or α-aminoacyl-α-aminoacyl, where each α-aminoacyl group is independently selected from the naturally occurring L-amino acids, $P(O)(OH)_2$, —$P(O)(O(C_1-C_6)$alkyl$)_2$ or glycosyl (the radical resulting from the removal of a hydroxyl group of the hemiacetal form of a carbohydrate), and the like.

If a compound of Formula (I) incorporates an amine functional group, a prodrug can be formed by the replacement of a hydrogen atom in the amine group with a group such as, for example, R-carbonyl, RO-carbonyl, NRR'-carbonyl where R and R' are each independently $(C_1-C_{10})$ alkyl, $(C_3-C_7)$cycloalkyl, benzyl, or R-carbonyl is a natural α-aminoacyl or natural α-aminoacyl, —$C(OH)C(O)OY^1$ wherein $Y^1$ is H, $(C_1-C_6)$alkyl or benzyl, —$C(OY^2)Y^3$ wherein $Y^2$ is $(C_1-C_4)$ alkyl and $Y^3$ is $(C_1-C_6)$alkyl, carboxy $(C_1-C_6)$alkyl, amino$(C_1-C_4)$alkyl or mono-N— or di-N,N-$(C_1-C_6)$alkylaminoalkyl, —$C(Y^4)Y^5$ wherein $Y^4$ is H or methyl and $Y^5$ is mono-N— or di-N,N-$(C_1-C_6)$alkylamino morpholino, piperidin-1-yl or pyrrolidin-1-yl, and the like.

One or more compounds of the invention may exist in unsolvated as well as solvated forms with pharmaceutically acceptable solvents such as water, ethanol, and the like, and it is intended that the invention embrace both solvated and unsolvated forms. "Solvate" means a physical association of a compound of this invention with one or more solvent molecules. This physical association involves varying degrees of ionic and covalent bonding, including hydrogen bonding. In certain instances the solvate will be capable of isolation, for example when one or more solvent molecules are incorporated in the crystal lattice of the crystalline solid. "Solvate" encompasses both solution-phase and isolatable solvates. Non-limiting examples of suitable solvates include ethanolates, methanolates, and the like. "Hydrate" is a solvate wherein the solvent molecule is $H_2O$.

One or more compounds of the invention may optionally be converted to a solvate. Preparation of solvates is generally known. Thus, for example, M. Caira et al, *J. Pharmaceutical Sci.*, 93(3), 601–611 (2004) describe the preparation of the solvates of the antifungal fluconazole in ethyl acetate as well as from water. Similar preparations of solvates, hemisolvate, hydrates and the like are described by E. C. van Tonder et al, *AAPS Pharm Sci Tech.*, 5(1), article 12 (2004); and A. L. Bingham et al, *Chem. Commun.*, 603–604 (2001). A typical, non-limiting, process involves dissolving the inventive compound in desired amounts of the desired solvent (organic or water or mixtures thereof) at a higher than ambient temperature, and cooling the solution at a rate sufficient to form crystals which are then isolated by standard methods. Analytical techniques such as, for example I. R. spectroscopy, show the presence of the solvent (or water) in the crystals as a solvate (or hydrate).

"Effective amount" or "therapeutically effective amount" is meant to describe an amount of compound or a composition of the present invention effective in inhibiting the above-noted diseases and thus producing the desired therapeutic, ameliorative, inhibitory or preventative effect.

The compounds of Formula I can form salts which are also within the scope of this invention. Reference to a compound of Formula I herein is understood to include reference to salts thereof, unless otherwise indicated. The term "salt(s)", as employed herein, denotes acidic salts formed with inorganic and/or organic acids, as well as basic salts formed with inorganic and/or organic bases. In addition, when a compound of Formula I contains both a basic moiety, such as, but not limited to a pyridine or imidazole, and an acidic moiety, such as, but not limited to a carboxylic acid, zwitterions ("inner salts") may be formed and are included within the term "salt(s)" as used herein. Pharmaceutically acceptable (i.e., non-toxic, physiologically acceptable) salts are preferred, although other salts are also useful. Salts of the compounds of the Formula I may be formed, for example, by reacting a compound of Formula I with an amount of acid or base, such as an equivalent amount, in a medium such as one in which the salt precipitates or in an aqueous medium followed by lyophilization.

Exemplary acid addition salts include acetates, ascorbates, benzoates, benzenesulfonates, bisulfates, borates, butyrates, citrates, camphorates, camphorsulfonates, fumarates, hydrochlorides, hydrobromides, hydroiodides, lactates, maleates, methanesulfonates, naphthalenesulfonates, nitrates, oxalates, phosphates, propionates, salicylates, succinates, sulfates, tartarates, thiocyanates, toluenesulfonates (also known as tosylates,) and the like. Additionally, acids which are generally considered suitable for the formation of pharmaceutically useful salts from basic pharmaceutical compounds are discussed, for example, by P. Stahl et al, Camille G. (eds.) *Handbook of Pharmaceutical Salts. Properties, Selection and Use.* (2002) Zurich: Wiley-VCH; S. Berge et al, *Journal of Pharmaceutical Sciences* (1977) 66(1) 1–19; P. Gould, *International J. of Pharmaceutics* (1986) 33 201–217; Anderson et al, *The Practice of Medicinal Chemistry* (1996), Academic Press, New York; and in *The Orange Book* (Food & Drug Administration, Washington, D.C. on their website). These disclosures are incorporated herein by reference thereto.

Exemplary basic salts include ammonium salts, alkali metal salts such as sodium, lithium, and potassium salts, alkaline earth metal salts such as calcium and magnesium salts, salts with organic bases (for example, organic amines) such as dicyclohexylamines, t-butyl amines, and salts with amino acids such as arginine, lysine and the like. Basic nitrogen-containing groups may be quarternized with agents such as lower alkyl halides (e.g. methyl, ethyl, and butyl chlorides, bromides and iodides), dialkyl sulfates (e.g. dimethyl, diethyl, and dibutyl sulfates), long chain halides (e.g. decyl, lauryl, and stearyl chlorides, bromides and iodides), aralkyl halides (e.g. benzyl and phenethyl bromides), and others.

All such acid salts and base salts are intended to be pharmaceutically acceptable salts within the scope of the invention and all acid and base salts are considered equivalent to the free forms of the corresponding compounds for purposes of the invention.

Pharmaceutically acceptable esters of the present compounds include the following groups: (1) carboxylic acid esters obtained by esterification of the hydroxy groups, in which the non-carbonyl moiety of the carboxylic acid portion of the ester grouping is selected from straight or branched chain alkyl (for example, acetyl, n-propyl, t-butyl, or n-butyl), alkoxyalkyl (for example, methoxymethyl), aralkyl (for example, benzyl), aryloxyalkyl (for example, phenoxymethyl), aryl (for example, phenyl optionally substituted with, for example, halogen, $C_{1-4}$alkyl, or $C_{1-4}$alkoxy or amino); (2) sulfonate esters, such as alkyl- or aralkylsulfonyl (for example, methanesulfonyl); (3) amino acid esters (for example, L-valyl or L-isoleucyl); (4) phosphonate esters and (5) mono-, di- or triphosphate esters. The phosphate esters may be further esterified by, for example, a $C_{1-20}$ alcohol or reactive derivative thereof, or by a 2,3-di($C_{6-24}$) acyl glycerol.

Compounds of Formula I, and salts, solvates, esters and prodrugs thereof, may exist in their tautomeric form (for example, as an amide or imino ether). All such tautomeric forms are contemplated herein as part of the present invention.

The compounds of Formula (I) may contain asymmetric or chiral centers, and, therefore, exist in different stereoisomeric forms. It is intended that all stereoisomeric forms of the compounds of Formula (I) as well as mixtures thereof, including racemic mixtures, form part of the present invention. In addition, the present invention embraces all geometric and positional isomers. For example, if a compound of Formula (I) incorporates a double bond or a fused ring, both the cis- and trans-forms, as well as mixtures, are embraced within the scope of the invention.

Diastereomeric mixtures can be separated into their individual diastereomers on the basis of their physical chemical differences by methods well known to those skilled in the art, such as, for example, by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereomers and converting (e.g., hydrolyzing) the individual diastereomers to the corresponding pure enantiomers. Also, some of the compounds of Formula (I) may be atropisomers (e.g., substituted biaryls) and are considered as part of this invention. Enantiomers can also be separated by use of chiral HPLC column.

It is also possible that the compounds of Formula (I) may exist in different tautomeric forms, and all such forms are embraced within the scope of the invention. Also, for example, all keto-enol and imine-enamine forms of the compounds are included in the invention.

All stereoisomers (for example, geometric isomers, optical isomers and the like) of the present compounds (including those of the salts, solvates, esters and prodrugs of the compounds as well as the salts, solvates and esters of the prodrugs), such as those which may exist due to asymmetric carbons on various substituents, including enantiomeric forms (which may exist even in the absence of asymmetric carbons), rotameric forms, atropisomers, and diastereomeric forms, are contemplated within the scope of this invention, as are positional isomers (such as, for example, 4-pyridyl and 3-pyridyl). (For example, if a compound of Formula (I) incorporates a double bond or a fused ring, both the cis- and trans-forms, as well as mixtures, are embraced within the scope of the invention. Also, for example, all keto-enol and imine-enamine forms of the compounds are included in the invention.) Individual stereoisomers of the compounds of the invention may, for example, be substantially free of other isomers, or may be admixed, for example, as racemates or with all other, or other selected, stereoisomers. The chiral centers of the present invention can have the S or R configuration as defined by the IUPAC 1974 Recommendations. The use of the terms "salt", "solvate", "ester", "prodrug" and the like, is intended to equally apply to the salt, solvate, ester and prodrug of enantiomers, stereoisomers, rotamers, tautomers, positional isomers, racemates or prodrugs of the inventive compounds.

The present invention also embraces isotopically-labelled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, fluorine and chlorine, such as $^{2}H$, $^{3}H$, $^{13}C$, $^{14}C$, $^{15}N$, $^{18}O$, $^{17}O$, $^{31}P$, $^{32}P$, $^{35}S$, $^{18}F$, and $^{36}Cl$, respectively.

Certain isotopically-labelled compounds of Formula (I) (e.g., those labeled with $^{3}H$ and $^{14}C$) are useful in compound and/or substrate tissue distribution assays. Tritiated (i.e., $^{3}H$) and carbon-14 (i.e., $^{14}C$) isotopes are particularly preferred for their ease of preparation and detectability. Further, substitution with heavier isotopes such as deuterium (i.e., $^{2}H$) may afford certain therapeutic advantages resulting from greater metabolic stability (e.g., increased in vivo half-life or reduced dosage requirements) and hence may be preferred in some circumstances. Isotopically labelled compounds of Formula (I) can generally be prepared by following procedures analogous to those disclosed in the Schemes and/or in the Examples hereinbelow, by substituting an appropriate isotopically labelled reagent for a non-isotopically labelled reagent.

Polymorphic forms of the compounds of Formula I, and of the salts, solvates, esters and prodrugs of the compounds of Formula I, are intended to be included in the present invention.

Generally, the compounds of formula I can be prepared by a variety of methods well known to those skilled in the art, for example, by the methods as outlined in the examples disclosed herein.

The compounds according to the invention have pharmacological properties; in particular, the compounds of formula I are useful as HCV RNA-dependent RNA polymerase inhibitors. Accordingly, the present compounds are useful in the treatment or prevention of diseases/conditions that are treatable or preventable by inhibiting HCV RNA-dependent RNA polymerase. The present compounds are thus useful for treating diseases/conditions such as HCV infection, HIV infection, AIDS (Acquired Immune Deficiency Syndrome), and related disorders. The compounds of formula I may also be used for the manufacture of a medicament to treat disorders associated with the HCV RNA-dependent RNA polymerase.

As used herein, the phrases "HCV RNA-dependent RNA polymerase inhibitor", "HCV RdRp inhibitor", "inhibitor of HCV RNA-dependent RNA polymerase", and "inhibitor of HCV RdRp" refer to compounds that are capable of interacting with HCV RNA-dependent RNA polymerase and inhibiting its enzymatic activity. Inhibiting HCV RNA-dependent RNA polymerase enzymatic activity means reducing the ability of HCV RdRp to incorporate ribonucleotides into a growing HCV RNA strand. In some preferred embodiments, such reduction of HCV RdRp activity is at least 50%, more preferably at least 75%, and still more preferably at least 90%. In other preferred embodiments, HCV RdRp activity is reduced by at least 95% and more preferably by at least 99%. Preferred compounds are those which have a $IC_{50}$ value less than 100 nM (more preferably less than 50 nM; most preferably less than 20 nM).

Preferably, such inhibition is specific, i.e., the HCV RdRp inhibitor reduces the ability of HCV RdRp to incorporate ribonucleotides into a growing HCV RNA strand at a concentration that is lower than the concentration of the inhibitor that is required to produce another, unrelated biological effect. Preferably, the concentration of the inhibitor required for HCV RdRp inhibitory activity is at least 2-fold lower, more preferably at least 5-fold lower, even more preferably at least 10-fold lower, and most preferably at least 20-fold lower than the concentration required to produce an unrelated biological effect.

In another aspect, this invention relates to methods of inhibiting HCV replication in a cell. The methods comprise contacting a cell that is infected by HCV with at least one compound of formula I or a pharmaceutically acceptable salt or ester thereof or a composition according to the invention. In some embodiments, the cell is a hepatocyte. However, HCV is capable of replication in cell types other than hepatocytes, and the methods of the invention are also effective in such other cell types.

In some embodiments, the cell is a cultured cell that is capable of supporting replication of HCV. Cell culture systems that support HCV replication can be prepared by infection of primary cell cultures or cell lines, or by cultivation of primary cells from a chronically infected patient. Examples of such HCV replication systems can be found described, e.g., in Lohmann et al., *Science* 285: 110–113 (1999), Blight et al., *Science* 290: 1972 (2000), and Barenschlager and Lohmann, *J. Gen. Virology* 81: 8631–1648 (2000). In other embodiments, the cell is located in a human or animal.

In a further aspect, the present invention provides a use of at least one compound of formula I or a pharmaceutically acceptable salt or ester thereof for preparation of a medicament for use in prophylaxis or treatment of HCV infection.

In a further aspect, the invention provides methods for treating or preventing a disease or condition associated with HCV infection, comprising administering to a mammal infected with HCV a therapeutically or prophylactically effective amount of at least one compound or composition according to the invention. The phrase "disease or condition associated with HCV infection" refers to any illness or condition caused directly or indirectly by infection with HCV. Preferably, the mammal is a human.

HCV is characterized by pronounced genomic variability, and HCV replication leads to the rapid generation of virus variants. Holland et al., *Current Topics in Microbiology and Immunology* 176: 1–20 (1992) teaches that HCV exists, even within an individual patient, as a swarm of microvariants, a phenomenon the authors refer to as quasispecies. Therefore, the terms "hepatitis C virus" and "HCV", as used herein, are intended to refer to any of such virus variants, or mixtures thereof.

The phrase "effective amount" or "therapeutically effective amount", as used herein, refers to an amount sufficient to cause a benefit to a mammal or sufficient to cause any beneficial change in any symptom or marker associated with HCV infection. The phrase "marker associated with HCV infection" refers to any biological measure that correlates with HCV infection and/or is predictive of clinical prognosis. Such markers include, without limitation, active virus and viral antigens.

The term "prophylactically effective amount", as used herein, refers to an amount sufficient to prevent or reduce the severity of HCV symptoms in a mammal exposed to or infected by HCV. In some embodiments, prophylactic treatment includes administering a compound or composition according to the invention to a patient found to carry HCV, but which does not exhibit symptoms of hepatitis C disease. Prophylactic treatment also includes administering a compound or composition according to the invention to a patient who shows an improved disease state, but which still carries HCV and is at risk of recurrence of symptomatic disease.

The effective (e.g., therapeutically or prophylactically) amount of the HCV RdRp inhibitor administered will be determined empirically, and will be based on such considerations as the particular inhibitor used, the age, body weight, and condition of the individual, the treatment effect desired, administration route, and the like. A typical dose ranges from about 0.1 mg/kg to about 1,000 mg/kg per dose, which can be given one to several times per day. A preferred dosage is about 1 to 250 mg/kg per dose.

Generally, the human oral dosage form containing the active ingredients can be administered 1 or 2 times per day. The amount and frequency of the administration will be regulated according to the judgment of the attending clinician. A generally recommended daily dosage regimen for oral administration may range from about 1.0 milligram to about 1,000 milligrams per day, in single or divided doses.

For administration of pharmaceutically acceptable salts of the above compounds, the weights indicated above refer to the weight of the acid equivalent or the base equivalent of the therapeutic compound derived from the salt.

In yet another embodiment, the compounds of the invention may be used in combination (administered at the same time or sequentially) with one or more additional agents for treating viral infections, e.g., antiviral agents or immunomodulatory agents. In some embodiments, the additional agent is an inhibitor of HCV RdRp, HCV helicase, HCV protease, or another HCV target protein.

Examples of such antiviral and/or immunomodulatory agents include Ribavirin (from Schering-Plough Corporation, Madison, N.J.) and Levovirin™ (from ICN Pharmaceuticals, Costa Mesa, Calif.), VP 50406™ (from Viropharma, Incorporated, Exton, Pa.), ISIS 14803™ (from ISIS Pharmaceuticals, Carlsbad, Calif.), Heptazyme™ (from Ribozyme Pharmaceuticals, Boulder, Colo.), VX 497™ (from Vertex Pharmaceuticals, Cambridge, Mass.), Thymosin™ (from SciClone Pharmaceuticals, San Mateo, Calif.), Maxamine™ (Maxim Pharmaceuticals, San Diego, Calif.), mycophenolate mofetil (from Hoffman-LaRoche, Nutley, N.J.), interferon (such as, for example, interferon-alpha, PEG-interferon alpha conjugates) and the like. "PEG-interferon alpha conjugates" are interferon alpha molecules covalently attached to a PEG molecule. Illustrative PEG-interferon alpha conjugates include interferon alpha-2a (Roferon™, from Hoffman La-Roche, Nutley, N.J.) in the form of pegylated interferon alpha-2a (e.g., as sold under the trade name Pegasys™), interferon alpha-2b (Intron™, from Schering-Plough Corporation) in the form of pegylated interferon alpha-2b (e.g., as sold under the trade name PEG-Intron™), interferon alpha-2c (Berofor Alpha™, from Boehringer Ingelheim, Ingelheim, Germany) or consensus interferon as defined by determination of a consensus sequence of naturally occurring interferon alphas (Infergen™, from Amgen, Thousand Oaks, Calif.).

As described above, this invention thus includes combinations comprising an amount of at least one compound of formula I or a pharmaceutically acceptable salt or ester thereof, and an amount of one or more additional therapeutic agents listed above (administered together or sequentially) wherein the amounts of the compounds/treatments result in desired therapeutic effect.

When administering a combination therapy to a patient in need of such administration, the therapeutic agents in the combination, or a pharmaceutical composition or compositions comprising the therapeutic agents, may be administered in any order such as, for example, sequentially, concurrently, together, simultaneously and the like. The amounts of the various actives in such combination therapy may be different amounts (different dosage amounts) or same amounts (same dosage amounts). Thus, for illustration purposes, a compound of Formula I and an additional therapeutic agent may be present in fixed amounts (dosage amounts) in a single dosage unit (e.g., a capsule, a tablet and the like). A commercial example of such single dosage unit containing fixed amounts of two different active compounds is VYTORIN® (available from Merck Schering-Plough Pharmaceuticals, Kenilworth, N.J.).

If formulated as a fixed dose, such combination products employ the compounds of this invention within the dosage range described herein and the other pharmaceutically active agent or treatment within its dosage range. Compounds of formula I may also be administered sequentially with known therapeutic agents when a combination formulation is inappropriate. The invention is not limited in the sequence of administration; compounds of formula I may be administered either prior to or after administration of the known therapeutic agent. Such techniques are within the skills of persons skilled in the art as well as attending physicians.

The pharmacological properties of the compounds of this invention may be confirmed by a number of pharmacological assays. The inhibitory activity of the present compounds against HCV RNA-dependent RNA polymerase may be assayed by methods known in the art, for example, by using the methods as described in the examples.

While it is possible for the active ingredient to be administered alone, it is preferable to present it as a pharmaceutical composition. The compositions of the present invention comprise at least one active ingredient, as defined above, together with one or more acceptable carriers, adjuvants or vehicles thereof and optionally other therapeutic agents (e.g., antiviral or immunomodulatory agents). Each carrier, adjuvant or vehicle must be acceptable in the sense of being compatible with the other ingredients of the composition and not injurious to the mammal in need of treatment.

Accordingly, this invention also relates to pharmaceutical compositions comprising at least one compound of formula I, or a pharmaceutically acceptable salt or ester thereof and at least one pharmaceutically acceptable carrier, adjuvant or vehicle. The compositions according to the invention may contain, in addition to the HCV RdRp inhibitor, diluents, fillers, salts buffers, stabilizers, solubilizers, and other materials well known in the art, provided that such materials do not interfere with the effectiveness of the biological activity of the active ingredient(s).

The present invention also discloses methods for preparing pharmaceutical compositions comprising at least one compound of the present invention as an active ingredient. In the pharmaceutical compositions and methods of the present invention, the active ingredients will typically be administered in admixture with carrier, adjuvant or vehicle materials suitably selected with respect to the intended form of administration, i.e. oral tablets, capsules (either solid-filled, semi-solid filled or liquid filled), powders for constitution, oral gels, elixirs, dispersible granules, syrups, suspensions, and the like. For example, for oral administration in the form of tablets or capsules, the active drug component may be combined with any oral non-toxic pharmaceutically acceptable inert carrier, such as lactose, starch, sucrose, cellulose, magnesium stearate, dicalcium phosphate, calcium sulfate, talc, mannitol, ethyl alcohol (liquid forms) and the like. Moreover, when desired or needed, suitable binders, lubricants, disintegrating agents and coloring agents may also be incorporated in the mixture. Sweetening and flavoring agents and preservatives may also be included where appropriate. Powers and tablets may comprise from about 5 to about 95 percent active ingredient.

Suitable binders include starch, gelatin, natural sugars, corn sweeteners, natural and synthetic gums such as acacia, sodium alginate, carboxymethyl-cellulose, polyethylene glycol and waxes. Suitable lubricants include stearic acid, boric acid, sodium benzoate, sodium acetate, sodium chloride, and the like. Disintegrants include starch, methylcellulose, guar gum and the like.

Additionally, the compositions of the present invention may be formulated in sustained release form to provide the rate controlled release of any one or more of the components or active ingredients to optimize the therapeutic effects, i.e. HCV inhibitory activity and the like. Suitable dosage forms for sustained release include layered tablets containing layers of varying disintegration rates or controlled release polymeric matrices impregnated with the active components and shaped in tablet form or capsules containing such impregnated or encapsulated porous polymeric matrices.

Liquid form preparations include solutions, suspensions and emulsions. Water or water-propylene glycol solutions are useful for parenteral injections. Sweeteners and pacifiers may be added for oral solutions, suspensions and emulsions. Liquid form preparations may also include solutions for intranasal administration.

Aerosol preparations suitable for inhalation may include solutions and solids in powder form, which may be in combination with a pharmaceutically acceptable carrier such as inert compressed gas, e.g. nitrogen.

For preparing suppositories, a low melting wax such as a mixture of fatty acid glycerides such as cocoa butter is first melted, and the active ingredient is dispersed homogeneously therein by stirring or similar mixing. The molten homogeneous mixture is then poured into convenient sized molds, allowed to cool and thereby solidify.

Also included are solid form preparations that are intended to be converted, shortly before use, to liquid form preparations for either oral or parenteral administration. Such liquid forms include solutions, suspensions and emulsions.

The compounds of the invention may also be deliverable transdermally. The transdermal compositions may take the form of creams, lotions, aerosols and/or emulsions and can be included in a transdermal patch of the matrix or reservoir type as are conventional in the art for this purpose. Other examples of pharmaceutically acceptable formulations may be found in *Remington: The Science and Practice of Pharmacy*, 20*th* Ed., ed. A. Gennaro, Lippincott Williams & Wilkins, 2000.

Compounds of the invention may be formulated and administered by any route known in art, including but not limited to, subcutaneous, parenteral, oral, sublingual, transdermal, topical, or intrarectal. In some embodiments, oral administration is preferred. In other embodiments, subcutaneous administration is preferred.

Preferably, the pharmaceutical preparation is in a unit dosage form. In such form, the preparation is subdivided into suitably sized unit doses containing appropriate quantities of the active component, e.g., an effective amount to achieve the desired purpose.

Another aspect of this invention is a kit comprising a therapeutically effective amount of at least one compound of formula I or a pharmaceutically acceptable salt or ester thereof and at least one pharmaceutically acceptable carrier, adjuvant or vehicle.

Yet another aspect of this invention is a kit comprising an amount of at least one compound of formula I or a pharmaceutically acceptable salt or ester thereof and an amount of at least one additional therapeutic agent listed above, wherein the amounts of the two or more ingredients result in desired therapeutic effect.

The invention disclosed herein is exemplified by the following preparations and examples which should not be construed to limit the scope of the disclosure. Alternative mechanistic pathways and analogous structures will be apparent to those skilled in the art.

EXAMPLES

In general, the compounds of this invention may be prepared from known or readily prepared starting materials, following methods known to one skilled in the art and those illustrated below. All stereoisomers and tautomeric forms of the compounds are contemplated.

Preparative Example 1

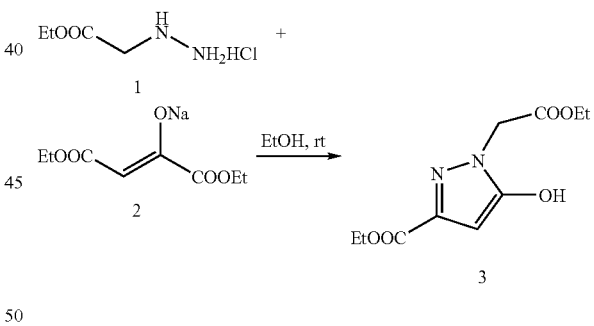

1-Ethoxycarbonylmethyl-5-hydroxy-1H-pyrazole-3-carboxylic acid ethyl ester (3)

A suspension of 1.60 g (10.3 mmol) of ethyl hydrazinoacetate hydrochloride 1 and 2.21 g (10.5 mmol) of diethyl oxalacetate sodium salt 2 in 20 mL of absolute ethanol was stirred at room temperature (rt) for approximately 2 days. The reaction mixture was concentrated to an oily residue, taken up in 50 mL of ethyl acetate, washed with water, brine, dried over sodium sulfate, filtered and evaporated to give 1.99 g (80%) of an orange-brown solid. Recrystallization from 3:2 ethyl acetate:hexane afforded 1.1 g (43%) of desired 3 as an off-white crystalline solid ($R_f$=0.18 (5% methanol in dichloromethane) as indicated by $^1$H NMR). $^1$H NMR δ (300 MHz, DMSO-$d_6$) 5.78 (s, 1H), 4.84 (s, 2H), 4.22 (q, 2H, J=7.0 Hz), 4.15 (q, 2H, J=7.0 Hz), 1.26 (t, 3H, J=7.0 Hz), 1.20 (t, 3H, J=7.0 Hz).

Preparative Example 2

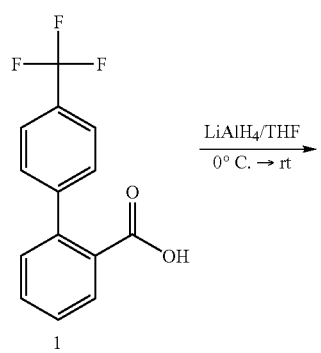

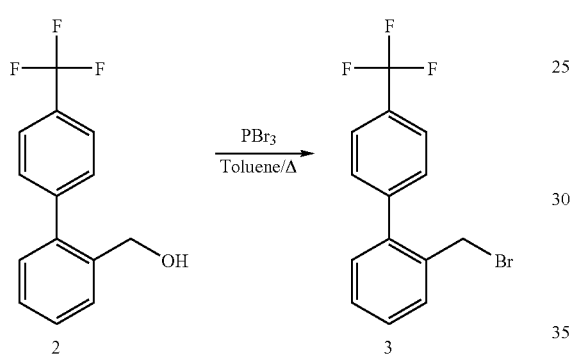

To an ice cold solution of 2.66 g (10 mmol) of 4'-trifluoromethyl-biphenyl-2-carboxylic acid (1) in 30 mL of tetrahydrofuran was added dropwise 10 mL (10 mmol) of 1 M LiAlH₄ solution in tetrahydrofuran, and the resulting mixture was stirred at rt for 2 h. The reaction mixture was cooled to 0° C. and quenched by the sequential addition of 10 ml of water, 10 mL of 3 M sodium hydroxide solution, and 30 mL of water. The mixture was then filtered through Celite, extracted with ethyl acetate, and the combined organic extracts were dried over sodium sulfate and concentrated to give a solid residue. Recrystallization from ethyl acetate gave 0.67 of starting material 1 as a white solid. The filtrate was concentrated and the resulting residue was chromatographed on silica gel (30% ethyl acetate in hexane) to afford 1.21 g (48%) of desired product 2 as a white solid ($R_f$=0.5 (30% ethyl acetate in hexane)) as indicated by ¹H NMR.

A mixture of 1.21 g (4.8 mmol) of (4'-trifluoromethyl-biphenyl-2-yl)-methanol (2) and 0.5 mL (5.3 mmol) of phosphorus tribromide in 10 mL of toluene was heated at reflux in a preheated oil bath for 10 min. The reaction mixture was then cooled to 0° C. and quenched with water, diluted with ethyl acetate and brine, and extracted with ethyl acetate. The combined organic extracts were washed with saturated sodium bicarbonate solution, brine, dried over sodium sulfate and evaporated to afford 2-bromomethyl-4'-trifluoromethyl-biphenyl (3) as a white solid as indicated by ¹H NMR.

Example 1

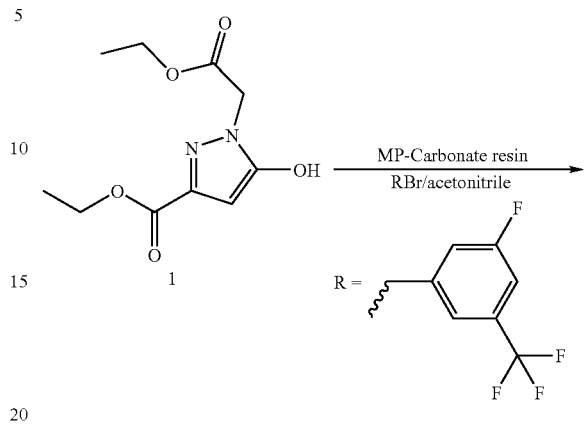

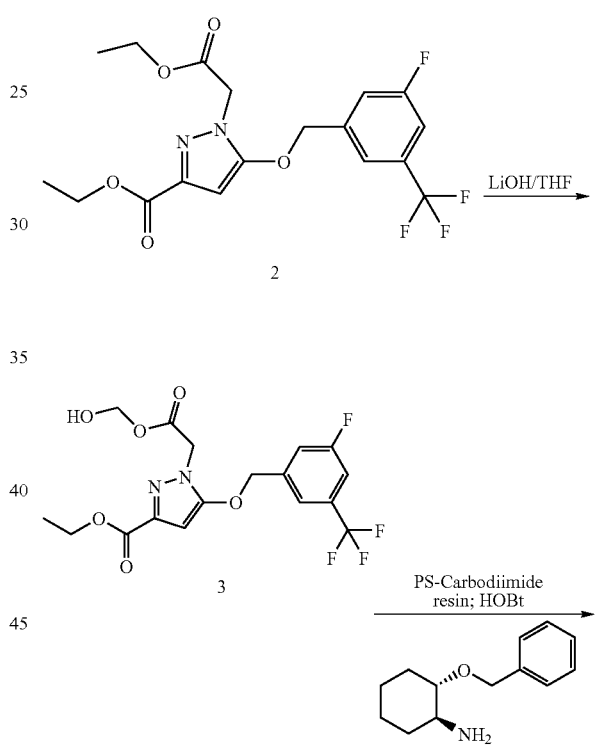

-continued

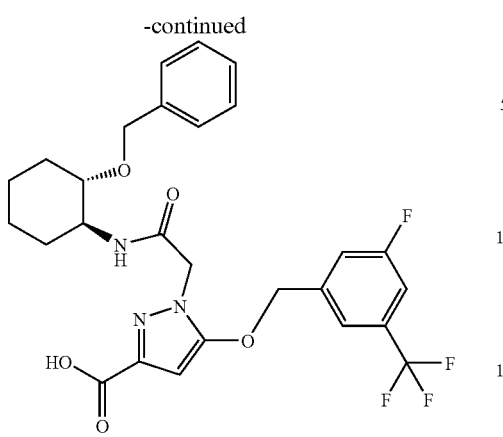

To a solution of 50 mg (0.206 mmol) of 1-ethoxycarbonylmethyl-5-hydroxy-1H-pyrazole-3-carboxylic acid ethyl ester (1) in 2 mL of acetonitrile was added 150 mg (1.0 mmol) of MP-carbonate resin, followed by 47 mg (0.185 mmol) of 1-bromomethyl-3-fluoro-5-trifluoromethyl-benzene and the reaction was shaken at rt overnight. The reaction mixture was then treated with 30 mg of thiophenol resin for 2 h, filtered and concentrated to give crude 1-ethoxycarbonylmethyl-5-(3-fluoro-5-trifluoromethyl-benzyloxy)-1H-pyrazole-3-carboxylic acid ethyl ester (2).

To an ice cold solution of 1-ethoxycarbonylmethyl-5-(3-fluoro-5-trifluoromethyl-benzyloxy)-1H-pyrazole-3-carboxylic acid ethyl ester (2) in 1 mL of tetrahydrofuran and 0.2 mL of water was added 0.21 mL (0.21 mmol) of 1 M LiOH solution, and the mixture was allowed to warm up to rt for 2 h. The reaction mixture was then acidified with 0.25 mL (0.25 mmol) of 1 M HCl solution, and extracted with ethyl acetate. The combined organic extracts were dried over sodium sulfate, and concentrated to give 58.5 mg (0.150 mmol) of 1-carboxymethyl-5-(3-fluoro-5-trifluoromethyl-benzyloxy)-1H-pyrazole-3-carboxylic acid ethyl ester (3) as crude product.

To a solution of 58.5 mg (0.15 mmol) of 1-carboxymethyl-5-(3-fluoro-5-trifluoromethyl-benzyloxy)-1H-pyrazole-3-carboxylic acid ethyl ester (3) in 5 mL of tetrahydrofuran was added 123 mg (0.60 mmol) of (1S, 2S)-2-benzyloxy-cyclohexylamine, 40 mg (0.30 mmol) of 1-hydroxybenzotriazole (HOBt) and 500 mg (0.60 mmol) of PS-carbodiimide resin, and the mixture was shaken at rt overnight. The reaction mixture was then treated with 200 mg (0.60 mmol) of MP-carbonate resin and 225 mg (0.9 mmol) of PS-TsOH resin, and shaken at rt for 4 h. The resulting mixture was filtered and washed with tetrahydrofuran (2×2 mL), and the combined tetrahydrofuran extracts were concentrated to afford crude 1-[((1S, 2S)-2-benzyloxy-cyclohexylcarbamoyl)-methyl]-5-(3-fluoro-5-trifluoromethyl-benzyloxy)-1H-pyrazole-3-carboxylic acid ethyl ester (4) which was used in the next reaction without any further purification.

To a solution of 1-[((1S, 2S)-2-Benzyloxy-cyclohexylcarbamoyl)-methyl]-5-(3-fluoro-5-trifluoromethyl-benzyloxy)-1H-pyrazole-3-carboxylic acid ethyl ester (4) in 1 mL of tetrahydrofuran was added 0.5 mL (0.5 mmol) of 1 M LiOH solution, and the resulting mixture was stirred at rt overnight. The reaction mixture was then acidified with 0.55 mL of 1 M HCl, and extracted with ethyl acetate. The combined organic extracts were dried over sodium sulfate, and concentrated to give a residue which was purified via reverse-phase chromatography using Gilson to afford (after lyophilization) 25 mg (0.045 mmol, 24% yield over 4 steps) of 1-[((1S, 2S)-2-Benzyloxy-cyclohexylcarbamoyl)-methyl]-5-(3-fluoro-5-trifluoromethyl-benzyloxy)-1H-pyrazole-3-carboxylic acid (compound 11) as a solid as indicated by $^1$H NMR. (δ CDCl$_3$ 7.36–7.22 (m, 8H), 6.10 (s, 1H), 5.90 (b, 1H), 4.99 (d, J=12.1 Hz, 1H), 4.93 (d, J=12.1 Hz, 1H), 4.77 (d, J=16.5 Hz, 1H), 4.70 (d, J=16.5 Hz, 1H), 4.58 (d, J=11.6 Hz, 1H), 4.30 (d, J=11.7 Hz, 1H), 3.76–3.73 (m, 1H), 3.20 (dt, J=3.8, 5.2 Hz, 1H), 2.24–2.21(m, 1H), 2.13–2.09 (m, 1H), 1.80–1.77 (m, 1H), 1.64–1.61 (m, 1H), 1.40–1.18 (m, 4H)); LC-MS calcd. for $C_{27}H_{27}F_4N_3O_5$ [M$^+$+H]: 550.2; found: 550.2.

Example 2

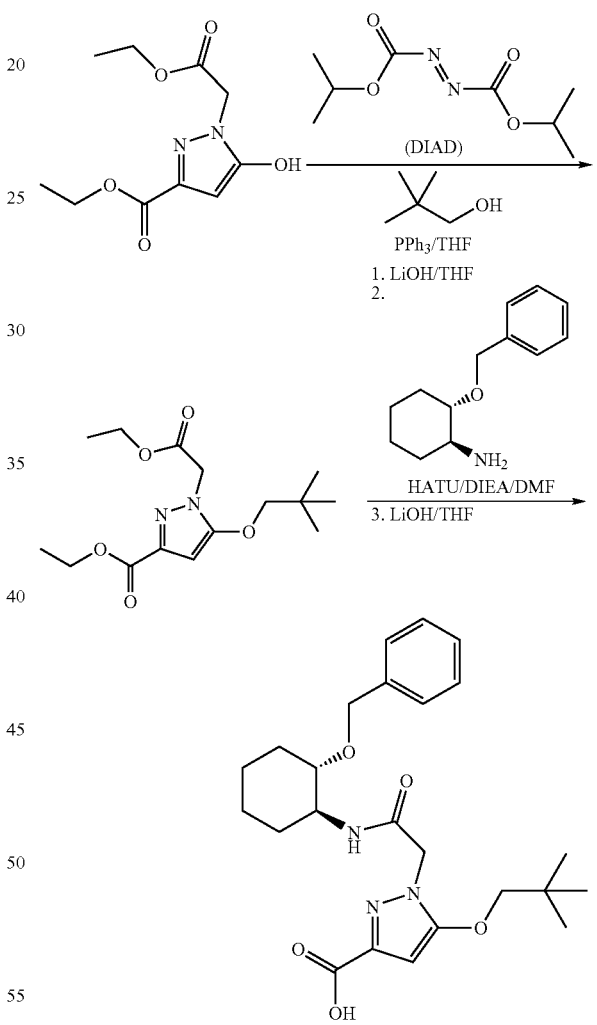

To an ice cold mixture of 50 mg (0.21 mmol) of 1-Ethoxycarbonylmethyl-5-hydroxy-1H-pyrazole-3-carboxylic acid ethyl ester in 2 mL of tetrahydrofuran was added 49 mg (0.25 mmol) of neopentyl alcohol, 108 mg (0.41 mmol) of triphenylphosphine, followed by 0.081 mL (0.41 mmol) of diisopropyl azodicarboxylate (DIAD) and the mixture was allowed to warm up to rt and stirred at rt overnight. The reaction mixture was then concentrated and the residue was chromatographed on silica gel (3:1 hexane:ethyl acetate) to give 46 mg (70%) of 5-(2,2-dimethyl-propoxy)-1-ethoxycarbonylmethyl-1H-pyrazole-3-carboxylic acid ethyl ester LC-MS calcd. for $C_{15}H_{24}N_2O_5$ [M$^+$+H]: 313.2; found: 313.2.

The conversion of 5-(2,2-dimethyl-propoxy)-1-ethoxycarbonylmethyl-1H-pyrazole-3-carboxylic acid ethyl ester to 1-[((1S, 2S)-2-benzyloxy-cyclohexylcarbamoyl)-methyl]-5-(2,2-dimethyl-propoxy)-1H-pyrazole-3-carboxylic acid was completed via known procedures described in the preparation of tetrazole of compound 9 (HATU coupling reaction) and in preparation of analogs of compound 9 via alkylation reactions (LiOH saponification reactions).

Example 3 oxy-benzyloxy)-1H-pyrazole-3-carboxylic acid ethyl ester (2) was treated with 5 mL of 95:5 trifluoroacetic acid (TFA):H$_2$O solution, and the resulting mixture was stirred for 1.5 h at rt, and then quenched by the addition of 5 mL of 1:1 acetonitrile:water solution. The mixture was concentrated to give 66 mg (86%) of crude 1-[((1S, 2S)2-benzyloxy-cyclohexylcarbamoyl)-methyl]-5-hydroxy-1H-pyrazole-3-carboxylic acid ethyl ester (3) which was used without any further purification in the next reaction.

To an ice cold mixture of 13 mg (0.032 mmol) of 1-[(2-benzyloxy-cyclohexylcarbamoyl)-methyl]-5-hydroxy-1H-pyrazole-3-carboxylic acid ethyl ester (3) in 1 mL of tetrahydrofuran was added 4 mg (0.036 mmol) of pyridin-

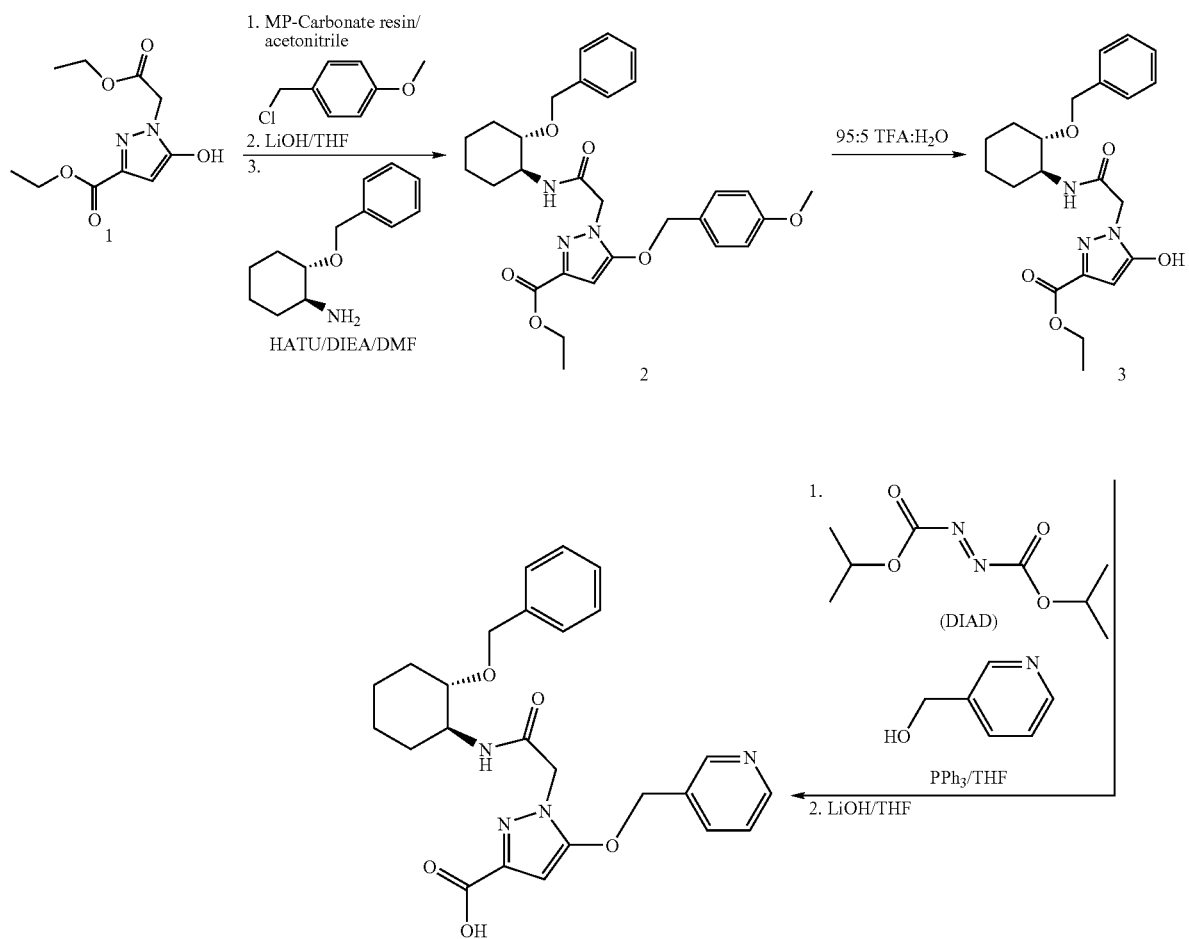

Preparation of 1-[((1S, 2S)2-Benzyloxy-cyclohexylcarbamoyl)-methyl]-5-(4-methoxy-benzyloxy)-1H-pyrazole-3-carboxylic acid ethyl ester (2) was accomplished via the same sequence that was used in the synthesis of compound 9 analogs via alkylation reactions (alkylation of 1 with 1-chloromethyl-4-methoxy-benzene, saponification with LiOH, coupling with 2-benzyloxy-cyclohexylamine using HATU). For experimental details see the preparation of the corresponding 3-fluoro-5-trifluoromethyl-benzyloxy pyrazole.

An ice cold sample of 100 mg (0.192 mmol) of 1-[((1S, 2S)2-Benzyloxy-cyclohexylcarbamoyl)-methyl]-5-(4-meth- 3-yl-methanol, 17 mg (0.064 mmol) of triphenylphosphine, followed by 0.013 mL (0.064 mmol) of diisopropyl azodicarboxylate (DIAD) and the mixture was allowed to warm up to rt and stirred at rt overnight. Then 0.3 mL (0.3 mmol) of 1 M LiOH solution was added, and the resulting mixture was stirred at rt overnight. The reaction mixture was then concentrated to give a residue which was purified via reverse-phase chromatography using Gilson to afford (after lyophilization) 7 mg (0.015 mmol, 42% yield over 2 steps) of 1-[(2-benzyloxy-cyclohexylcarbamoyl)-methyl]-5-(pyridin-3-ylmethoxy)-1H-pyrazole-3-carboxylic acid (compound 65). LC-MS calcd. for $C_{25}H_{28}N_4O_5$ [M$^+$+H]: 465.2; found: 465.2.

Example 4

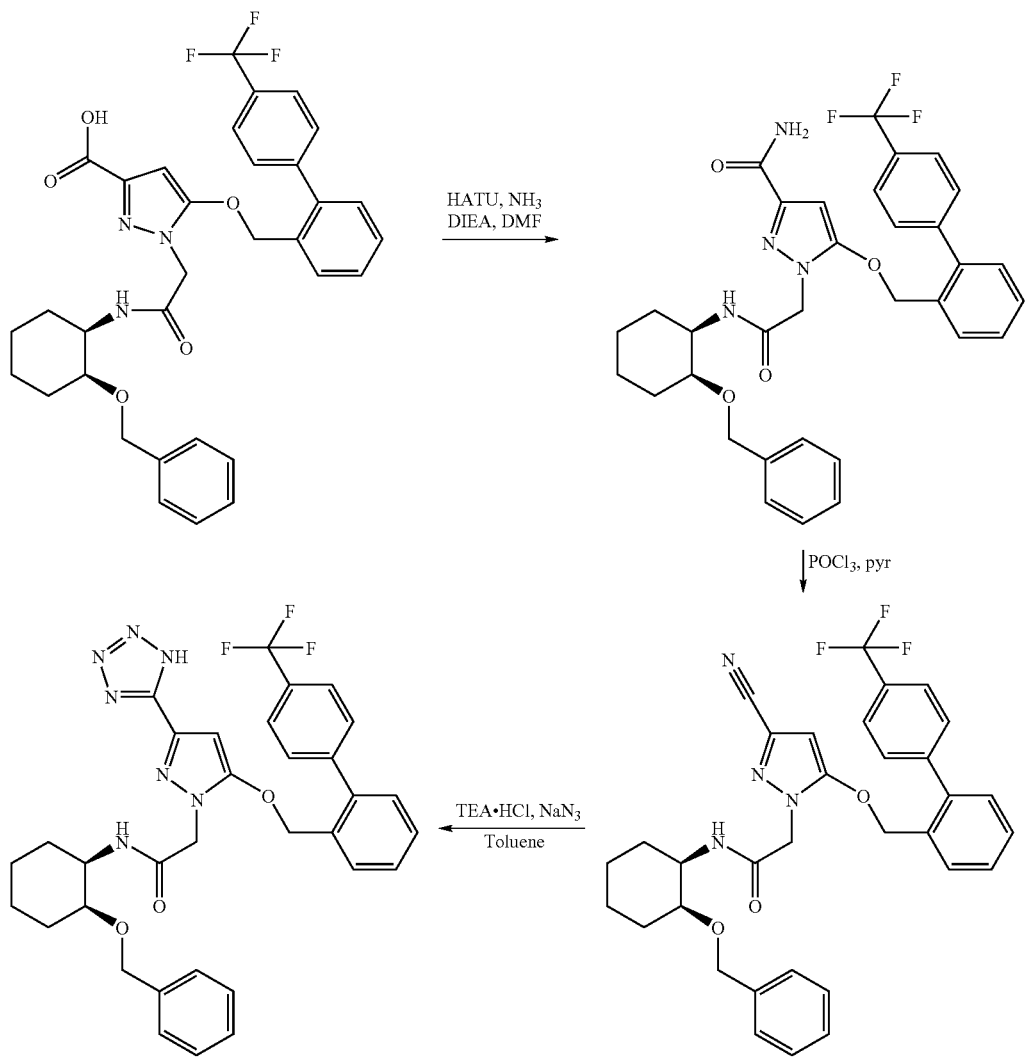

A solution of 200 mg (0.33 mmol) of 1-[(2-benzyloxy-cyclohexylcarbamoyl)-methyl]-5-(4'-trifluoromethyl-biphenyl-2-ylmethoxy)-1H-pyrazole-3-carboxylic acid (compound 9) in 2 mL of dimethylformamide was cooled at 0° C. To the above cold solution was added 0.493 mL (2.83 mmol) of N,N-diisopropylethylamine (DIEA), followed by 359 mg (0.94 mmol) of HATU, and 1.89 mL (0.94 mmol) of 0.5 M solution of ammonia in 1,4-dioxane. The resulting mixture was allowed to warm up to rt, and stirred at rt overnight. Since analysis by LC-MS indicated that the desired product was the major component, the reaction mixture was diluted with ethyl acetate, washed with 1N citric acid solution, then with saturated sodium bicarbonate solution, brine, dried over sodium sulfate and evaporated to give a yellow oil. (Rf=0.26 (5% methanol in dichloromethane)). The crude product 1-[(2-benzyloxy-cyclohexylcarbamoyl)-methyl]-5-(4'-trifluoromethyl-biphenyl-2-ylmethoxy)-1H-pyrazole-3-carboxylic acid amide was used without any further purification in the next reaction. LC-MS—calcd for $C_{33}H_{33}F_3N_4O_4$ [M+H]$^+$ 607.25, found 607.2.

To an ice cold solution of 310 mg (0.33 mmol max) of 1-[(2-benzyloxy-cyclohexylcarbamoyl)-methyl]-5-(4'-trifluoromethyl-biphenyl-2-ylmethoxy)-1H-pyrazole-3-carboxylic acid amide in 3 mL of pyridine was added 0.071 mL (0.76 mmol) of phosphorus oxychloride, and the resulting mixture was stirred at 0° C. for 2.5 h. The mixture was then diluted with ethyl acetate, washed with 1 N HCl solution, dried over sodium sulfate and concentrated. Since analysis by LC-MS indicated that some starting material was still present, the reaction was repeated under the same experimental conditions, and after complete consumption of starting material, it was worked up and purified via chromatography on silica gel (Biotage) with 3:1 hexane:ethyl acetate to give 71 mg (37% yield) of N-(2-benzyloxy-cyclohexyl)-2-[3-cyano-5-(4'-trifluoromethyl-biphenyl-2-ylmethoxy)- pyrazol-1-yl]-acetamide. LC-MS—calcd for $C_{33}H_{31}F_3N_4O_3$ [M+H]$^+$ 589.23, found 589.2.

According to a modification of a literature procedure (Bioorg. Med. Chem. 2002, 10, 3379–3393) to a solution of 31 mg (0.052 mmol) of N-(2-benzyloxy-cyclohexyl)-2-[3-cyano-5-(4'-trifluoromethyl-biphenyl-2-ylmethoxy)-pyrazol-1-yl]-acetamide in 2 mL of toluene was added 43 mg (0.31 mmol) of triethylamine hydrochloride, and 21 mg (0.32 mmol) of sodium azide and the resulting heterogeneous mixture was heated at 125° C. for 60 h. The mixture was then cooled to rt, filtered and concentrated to a residue which was purified via reverse-phase chromatography using Gilson to afford (after lyophilization) 7 mg (21% yield) of N-(2-benzyloxy-cyclohexyl)-2-[3-(1H-tetrazol-5-yl)-5-(4'-trifluoromethyl-biphenyl-2-ylmethoxy)-pyrazol-1-yl]-acetamide (compound 66) as a solid as indicated by $^1$H-NMR. (LC-MS calcd for C33H32F3N7O3 [M−H]$^-$ 630.25; found 630.0).

Example 5

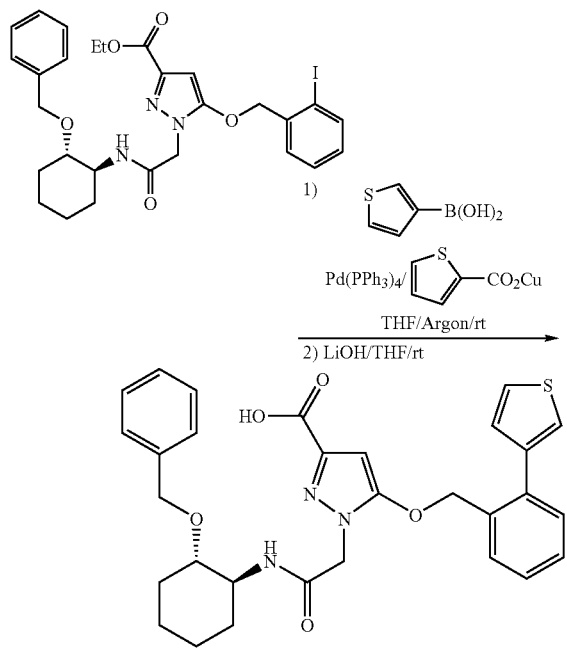

According to a procedure by Savarin and Liebeskind (Org. Lett. 2001, 3, 2149–2152) a mixture of 40 mg (0.065 mmol) of 1-[(2-benzyloxy-cyclohexylcarbamoyl)-methyl]-5-(2-iodo-benzyloxy)-1H-pyrazole-3-carboxylic acid ethyl ester, 10 mg (0.077 mmol, 1.2 equiv) of thiophene-3-boronic acid, 4 mg (0.0032 mmol, 5 mol %) of Pd(PPh$_3$)$_4$, and 15 mg (0.077 mmol, 1.2 equiv) of copper(I) thiophene-2-carboxylate (CuTC) was placed into a Schlenk flask. After a vacuum and argon cycle, tetrahydrofuran (2 mL) was added, and the resulting mixture was stirred at rt under argon for 14 h. The reaction mixture was diluted with water and extracted with ethyl acetate. The combined ethyl acetate extracts were washed with brine, filtered through a small pad of Celite, dried over sodium sulfate and evaporated to give 43 mg of a brown residue (crude coupling product).

The above residue was taken in tetrahydrofuran (2 mL) and 0.325 mL (0.325 mmol, 5 equiv) of 1 M LiOH solution was added, and the resulting mixture was stirred at rt for 17 h. The reaction mixture was then diluted with ethyl acetate, and acidified with 1N HCl solution to pH 2. The organic extract was washed with brine, dried over sodium sulfate and evaporated to give 38 mg of a brown residue which was purified via reverse-phase chromatography using Gilson to afford (after lyophilization) 9 mg (24% overall yield) of 1-[(2-benzyloxy-cyclohexylcarbamoyl)-methyl]-5-(2-thiophen-3-yl-benzyloxy)-1H-pyrazole-3-carboxylic acid (compound 58) as a white solid (85% purity), as indicated by $^1$H-NMR. (LC-MS shows M+1 ion—calcd 546.2; found 546.1).

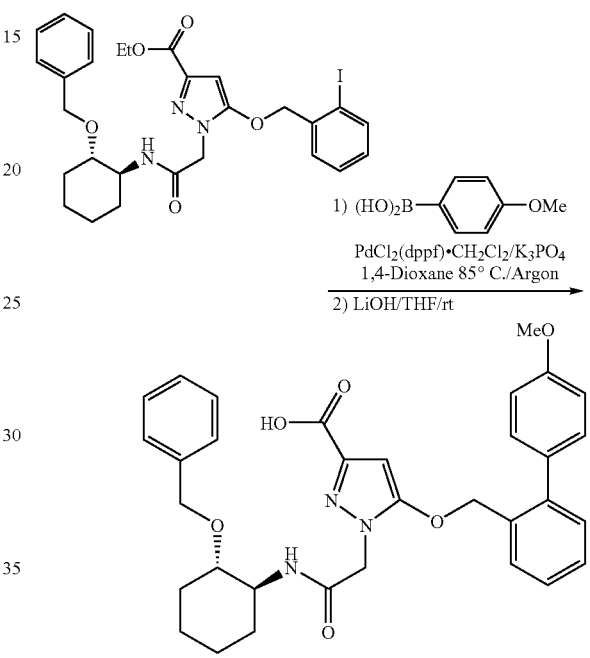

Example 6

A mixture of 37 mg (0.06 mmol) of 1-[(2-benzyloxy-cyclohexylcarbamoyl)-methyl]-5-(2-iodo-benzyloxy)-1H-pyrazole-3-carboxylic acid ethyl ester, 15 mg (0.097 mmol, 1.5 equiv) of 4-methoxyphenylboronic acid, 3 mg (0.0032 mmol, 5 mol %) of Pd catalyst, and 42 mg (0.194 mmol, 3 equiv) of potassium phosphate was placed into a carousel tube. After a vacuum and argon cycle, 1,4-dioxane (2 mL) was added, and the resulting mixture was heated at 85° C. under argon for 14 h. The reaction mixture was diluted with ethyl acetate, filtered through a small pad of Celite, dried over sodium sulfate and evaporated to give a brown residue (crude coupling product).

The above residue was taken in tetrahydrofuran (1.6 mL) and 0.4 mL (0.4 mmol, 6.6 equiv) of 1 M LiOH solution was added, and the resulting mixture was stirred at rt for 15 h. The reaction mixture was then diluted with ethyl acetate, and acidified with 1N HCl solution to pH 2. The organic extract was washed with brine, dried over sodium sulfate and evaporated to give a brown residue which was purified via reverse-phase chromatography using a Gilson apparatus to afford (after lyophilization) 8 mg (23% overall yield) of 1-[(2-benzyloxy-cyclohexylcarbamoyl)-methyl]-5-(4'-methoxy-biphenyl-2-ylmethoxy)-1H-pyrazole-3-carboxylic acid (compound 50) as a white solid (95% purity), as indicated by ¹H-NMR. (LC-MS shows M+1 ion—calcd 570.25; found 570.2).

Assay for HCV RNA-dependent RNA Polymerase Activity

Inhibitory activity of the present compounds against HCV RNA-dependent RNA polymerase was assayed according to the methods disclosed in U.S. Patent Application U.S.2004/038993, content of which is incorporated herein by reference; and those described in Ferrari, E.; Wright-Minogue, J.; Fang, J. W. S.; Baroudy, B. M.; Lau, J. Y. N.; Hong, Z. *J. Virol.* 1999, 73, 1649.

Briefly, 50 µl reactions containing 20 mM HEPES (pH 7.3), 7.5 mM DTT, 20 units/ml RNasIN, 0.5 ug/ml biotinylated oligoG$_{12}$, 5 µg/ml polyC, 5 µM GTP, 20 µCi/ml [³H]-GTP, 10 mM MgCl$_2$, 60 mM NaCl, 100 µg/ml BSA, and 50 nM NS5B (Δ21) were incubated at room temperature for three hours in 96-well plates with or without test compounds. Assay was terminated by the addition of 50 µl 10 mg/ml streptavidin-coated SPA beads supplemented with 100 mM EDTA, and the incorporation of labeled GTP determined by a TopCount Scintillation Counter. IC$_{50}$ values were calculated from single experiments using 11 serial 2-fold dilutions (0.05–50 µM), and data were considered reliable only when the IC$_{50}$ value of a positive internal control was within standard deviation range.

HCV RNA-dependent RNA polymerase inhibitory activities for representative compounds are shown in Table 2 below.

TABLE 2

| Compound No. | Structure | Δ21 Activity (IC$_{50}$ µM) |
|---|---|---|
| 1 | 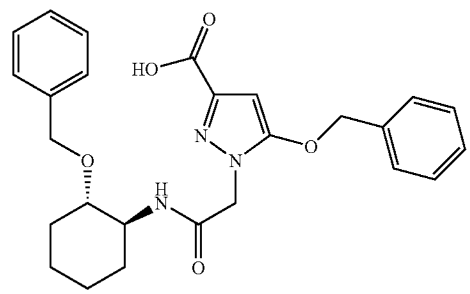 | 43 |
| 2 | 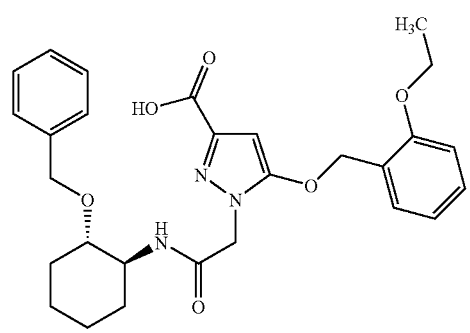 | 1 |
| 3 | 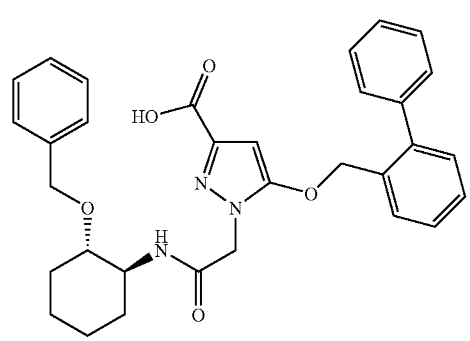 | 1 |

TABLE 2-continued

| Compound No. | Structure | Δ21 Activity (IC$_{50}$ μM) |
|---|---|---|
| 4 | 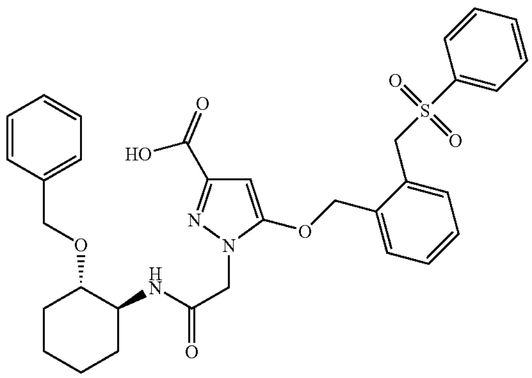 | 32 |
| 5 | 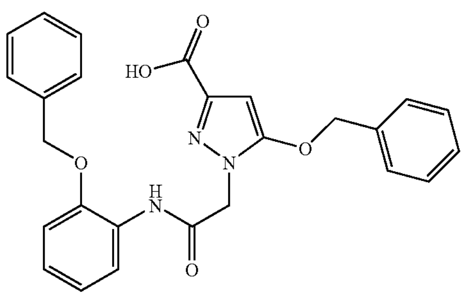 | 11 |
| 6 | 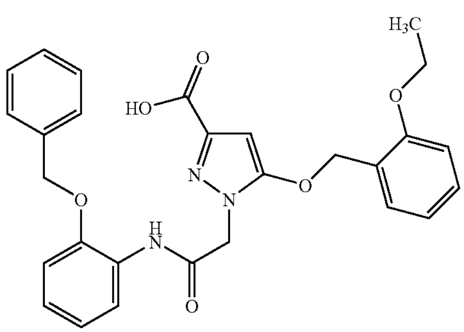 | 40 |
| 7 | 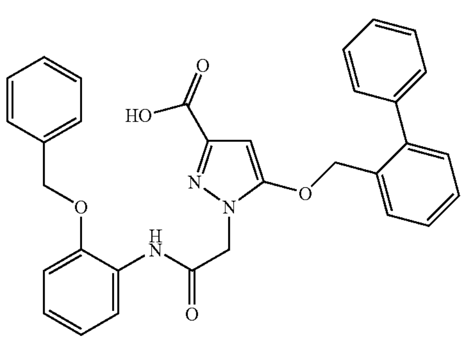 | 11 |

TABLE 2-continued

| Compound No. | Structure | Δ21 Activity (IC$_{50}$ μM) |
|---|---|---|
| 8 | 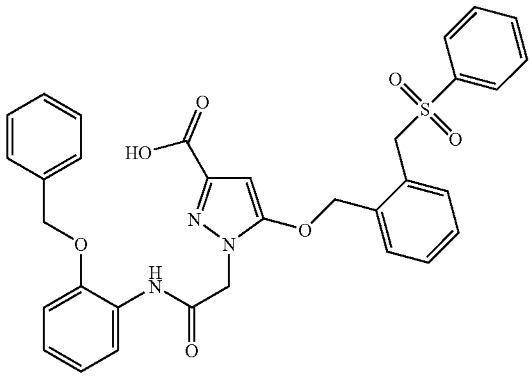 | 0.8 |
| 9 | 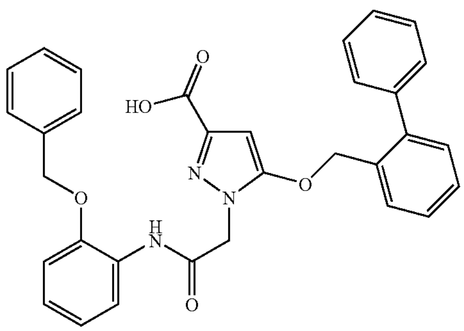 | 0.057 |
| 10 | 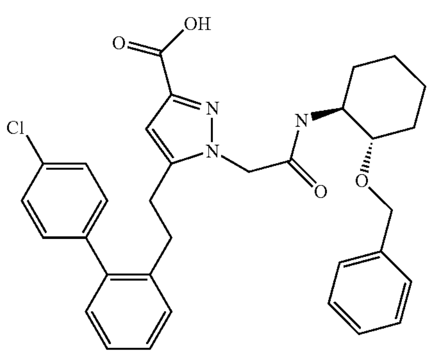 | 0.064 |
| 11 | 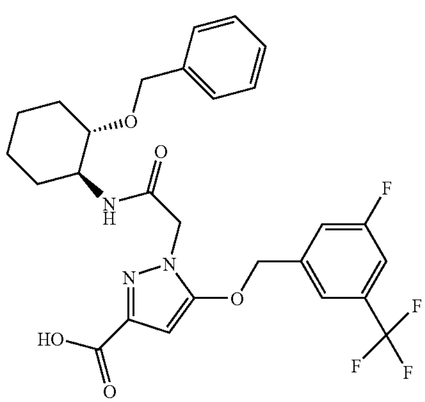 | 1.800 |

TABLE 2-continued
| Compound No. | Structure | Δ21 Activity (IC$_{50}$ μM) |
|---|---|---|
| 12 | 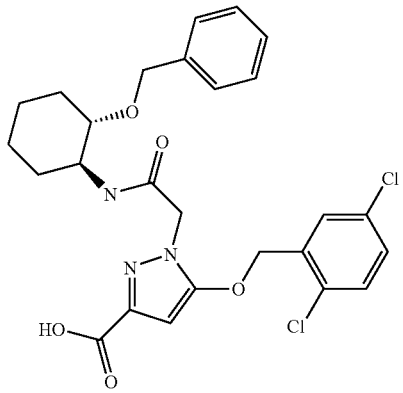 | 3.900 |
| 13 | 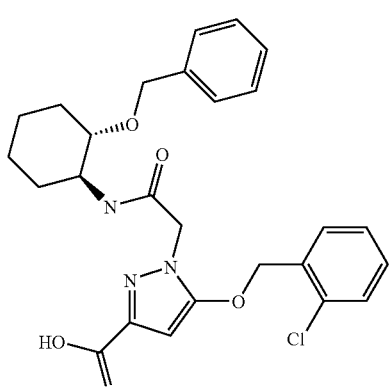 | >12.5 |
| 14 | 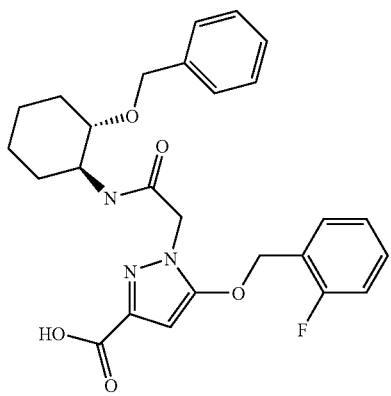 | >12.5 |

TABLE 2-continued
| Compound No. | Structure | Δ21 Activity (IC$_{50}$ μM) |
|---|---|---|
| 15 | 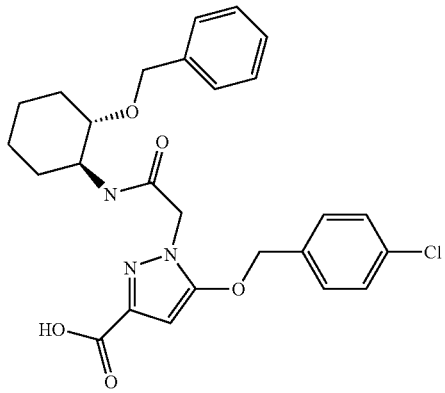 | 2.400 |
| 16 | 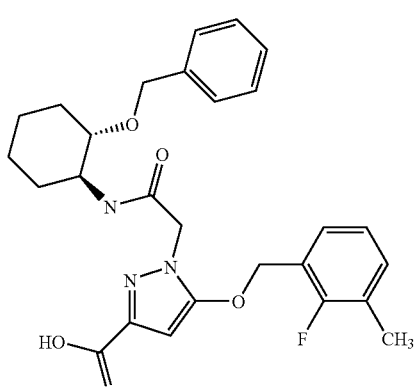 | 8.400 |
| 17 | 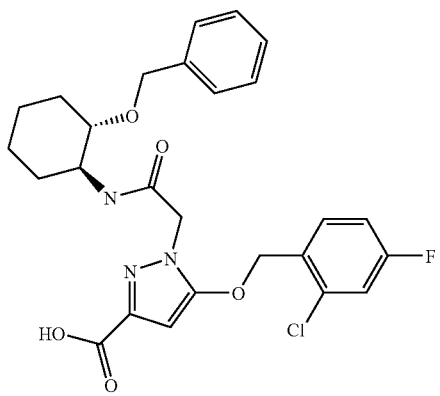 | 9.500 |

TABLE 2-continued

| Compound No. | Structure | Δ21 Activity (IC$_{50}$ μM) |
|---|---|---|
| 18 | 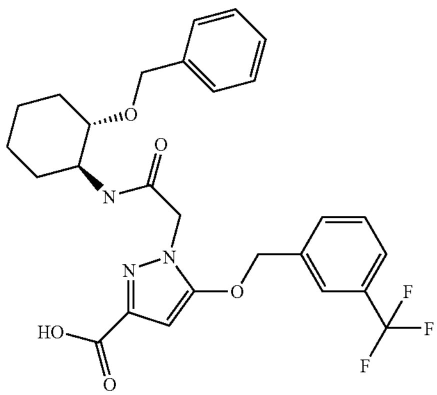 | 2.100 |
| 19 | 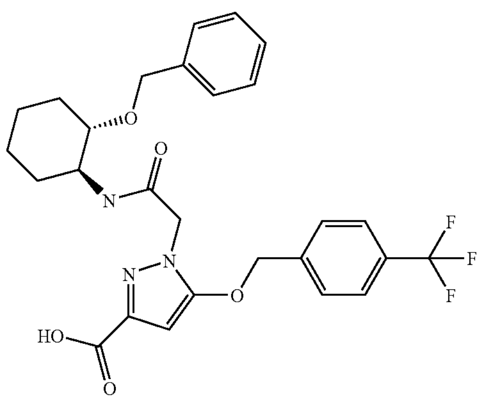 | 0.620 |
| 20 | 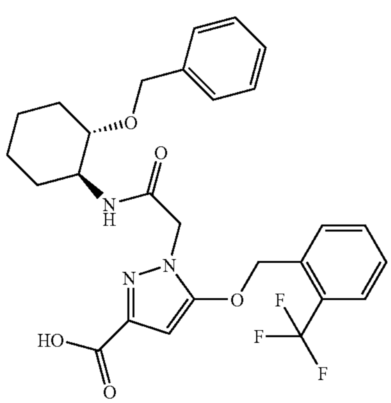 | 2.900 |

TABLE 2-continued

| Compound No. | Structure | Δ21 Activity (IC$_{50}$ μM) |
|---|---|---|
| 21 | 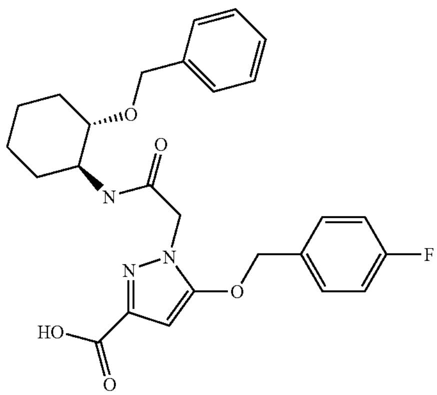 | 13.000 |
| 22 | 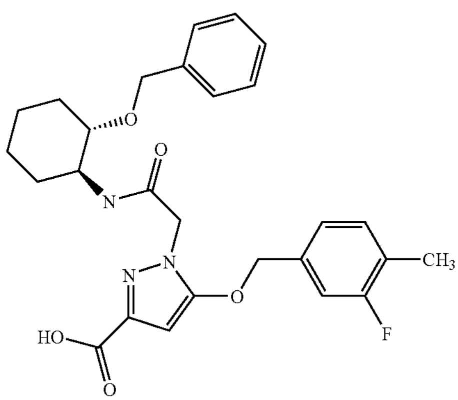 | 3.000 |
| 23 | 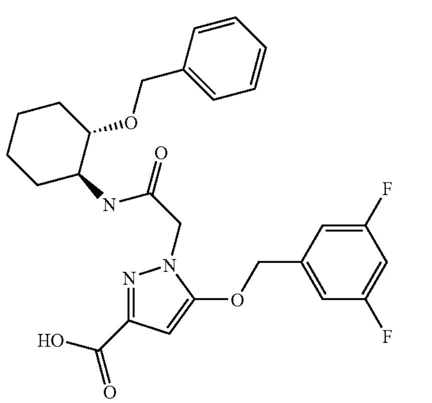 | 12.000 |

TABLE 2-continued

| Compound No. | Structure | Δ21 Activity (IC$_{50}$ μM) |
|---|---|---|
| 24 | 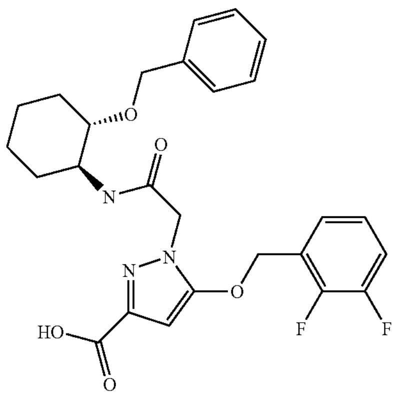 | >12.5 |
| 25 | 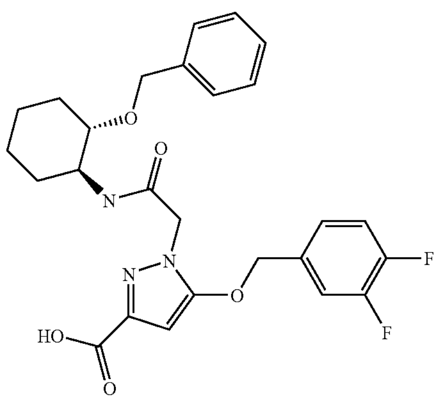 | 4.300 |
| 26 | 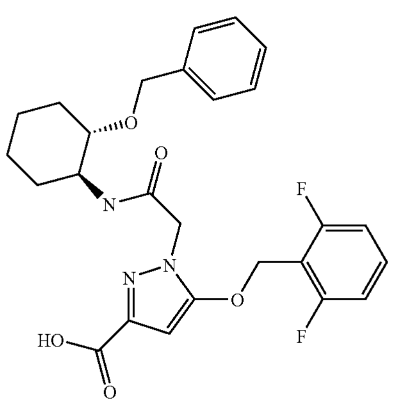 | >50 |

TABLE 2-continued

| Compound No. | Structure | Δ21 Activity (IC$_{50}$ μM) |
|---|---|---|
| 27 | 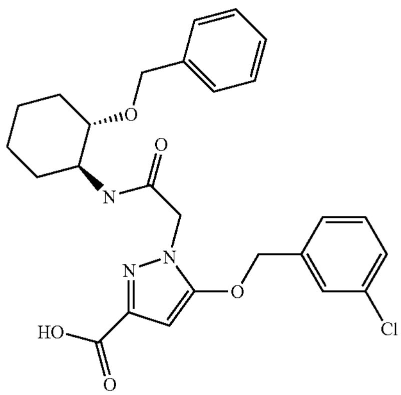 | 8.600 |
| 28 | 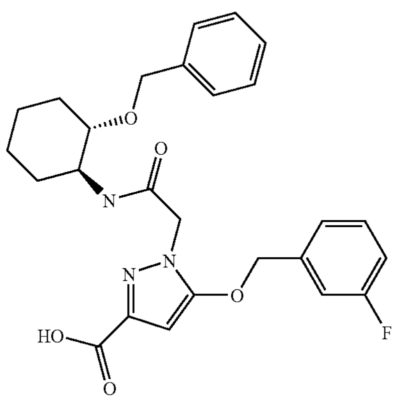 | >12.5 |
| 29 | 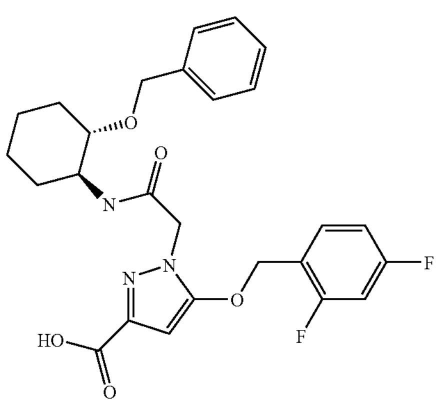 | >12.5 |

TABLE 2-continued

| Compound No. | Structure | Δ21 Activity (IC$_{50}$ μM) |
|---|---|---|
| 30 | 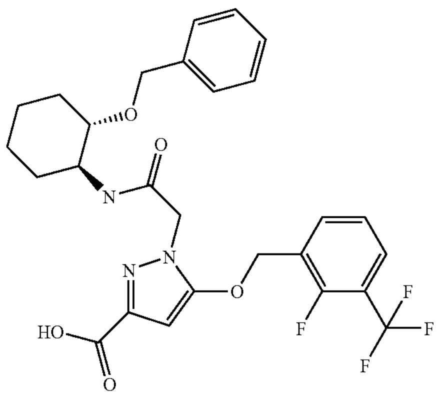 | 2.000 |
| 31 | 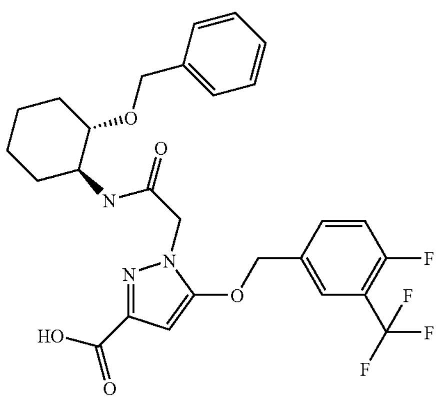 | 1.400 |
| 32 | 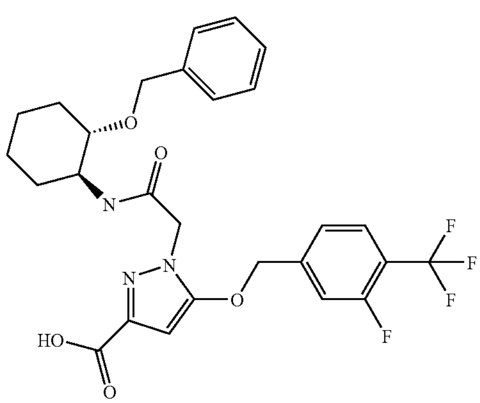 | 0.280 |

TABLE 2-continued

| Compound No. | Structure | Δ21 Activity (IC$_{50}$ μM) |
|---|---|---|
| 33 | 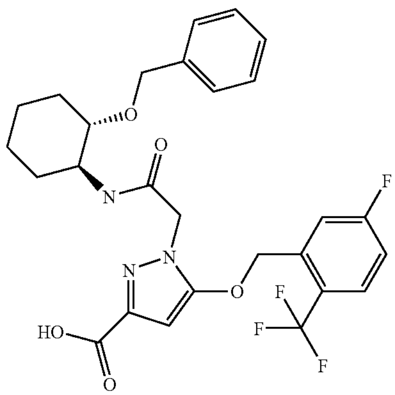 | 2.900 |
| 34 | 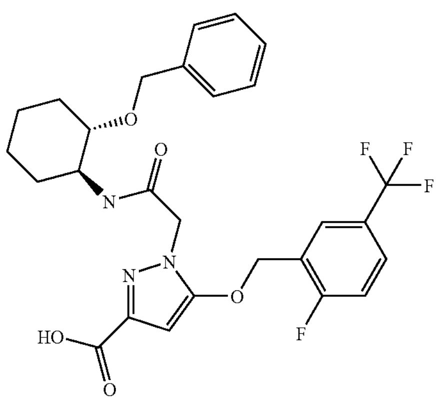 | 6.100 |
| 35 | 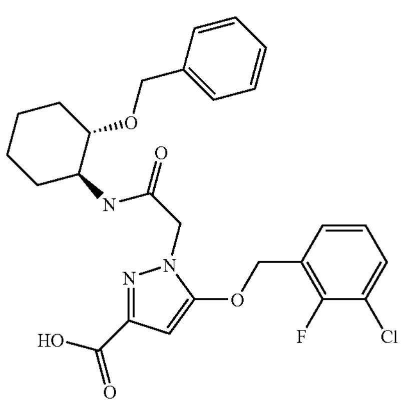 | 9.200 |

TABLE 2-continued

| Compound No. | Structure | Δ21 Activity (IC$_{50}$ μM) |
|---|---|---|
| 36 | 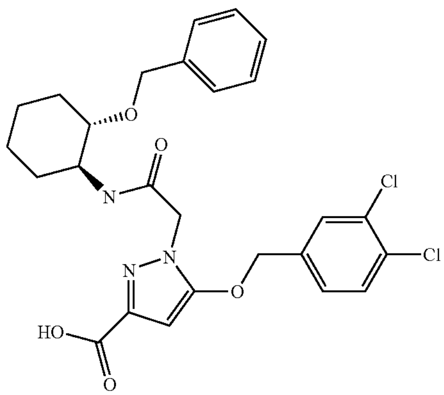 | 0.860 |
| 37 | 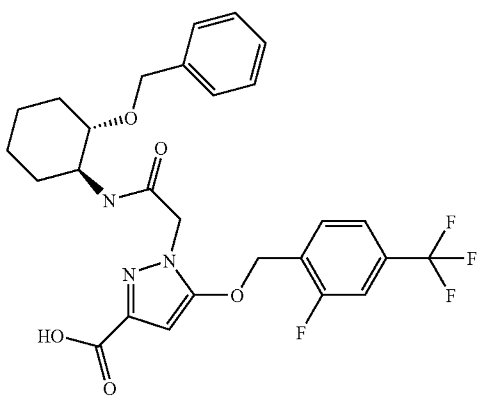 | 6.200 |
| 38 | 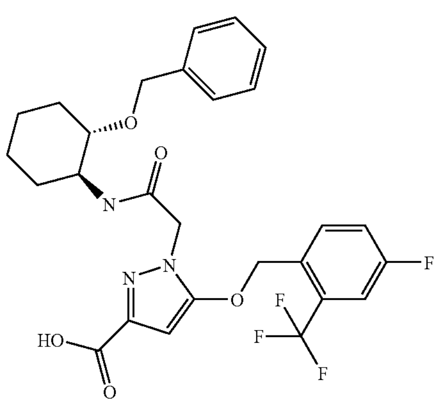 | 2.600 |

TABLE 2-continued

| Compound No. | Structure | Δ21 Activity (IC$_{50}$ μM) |
|---|---|---|
| 39 | 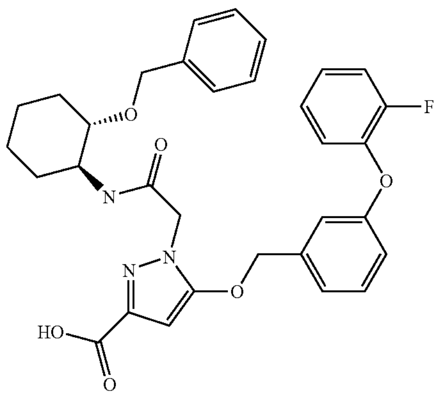 | 2.200 |
| 40 | 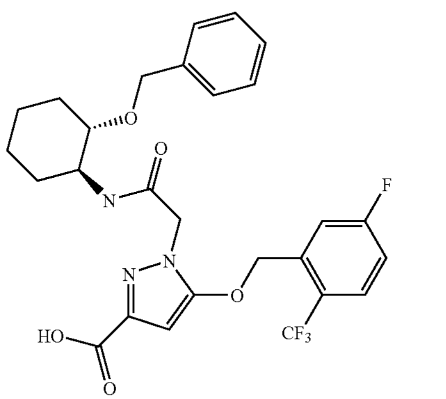 | 3.100 |
| 41 | 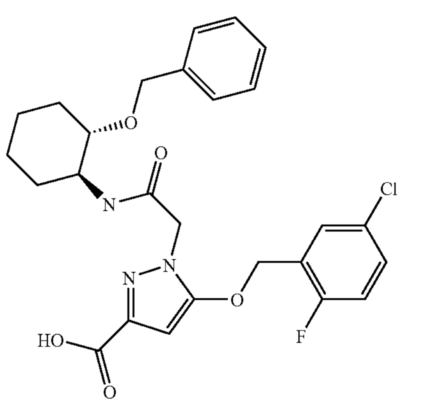 | 7.800 |

TABLE 2-continued

| Compound No. | Structure | Δ21 Activity (IC$_{50}$ μM) |
|---|---|---|
| 42 | 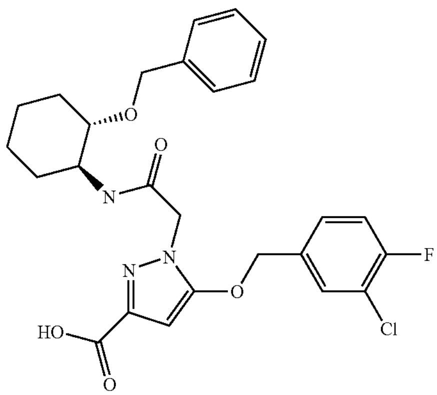 | 13.000 |
| 43 | 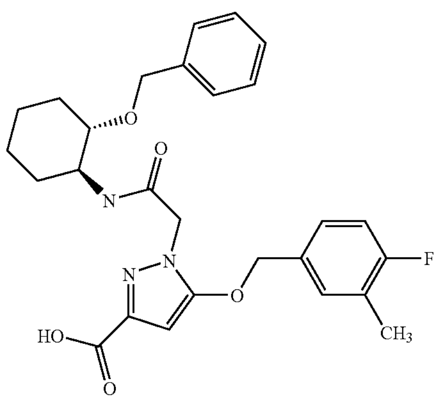 | 3.100 |
| 44 | 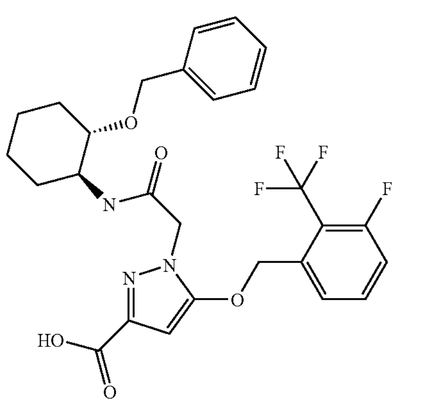 | 4.500 |

TABLE 2-continued

| Compound No. | Structure | Δ21 Activity (IC$_{50}$ μM) |
|---|---|---|
| 45 | 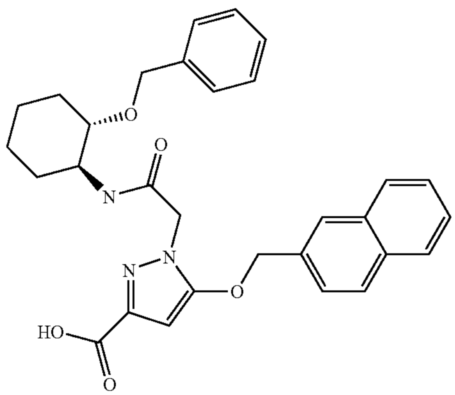 | 6.800 |
| 46 | 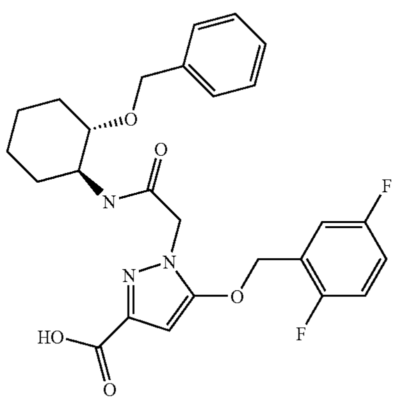 | >12.5 |
| 47 | 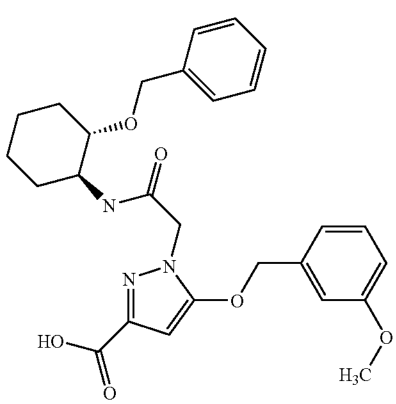 | >50 |

TABLE 2-continued

| Compound No. | Structure | Δ21 Activity (IC$_{50}$ μM) |
| --- | --- | --- |
| 48 | 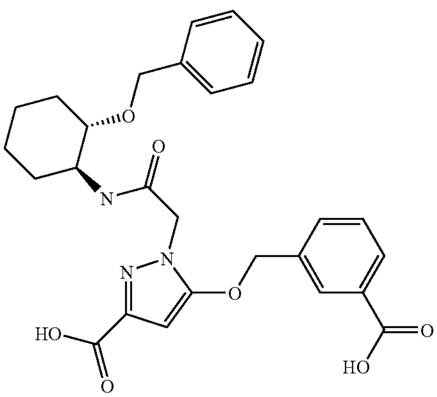 | >50 |
| 49 | 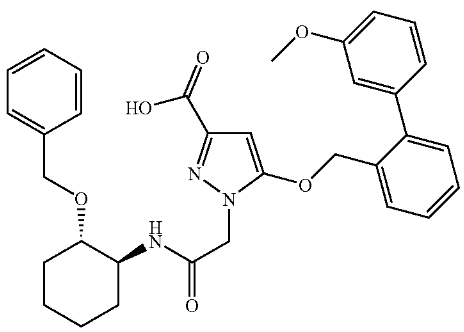 | 3.600 |
| 50 | 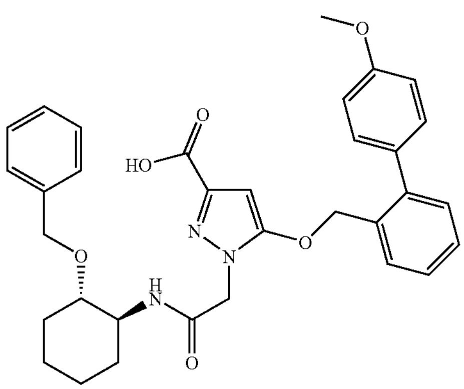 | 0.380 |
| 51 | 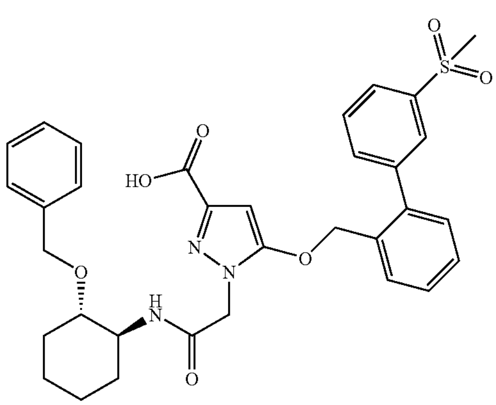 | 22.000 |

TABLE 2-continued

| Compound No. | Structure | Δ21 Activity (IC$_{50}$ μM) |
|---|---|---|
| 52 | 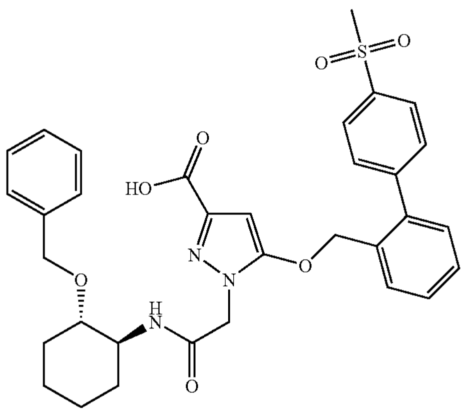 | 9.200 |
| 53 | 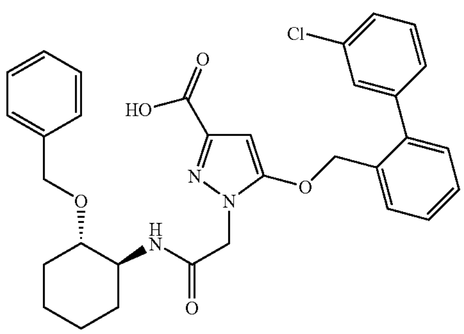 | 0.780 |
| 54 | 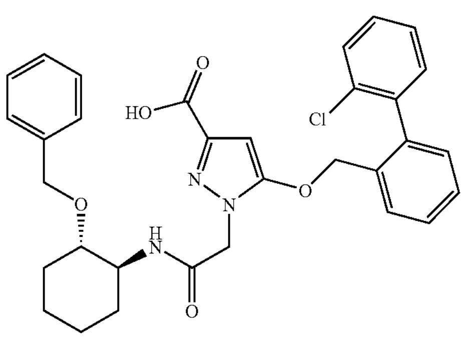 | 2.600 |
| 55 | 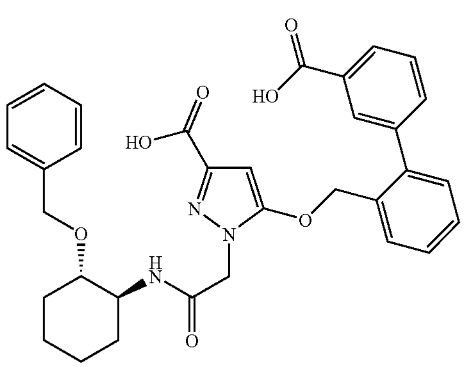 | >12.5 |

TABLE 2-continued

| Compound No. | Structure | Δ21 Activity (IC$_{50}$ μM) |
|---|---|---|
| 56 | 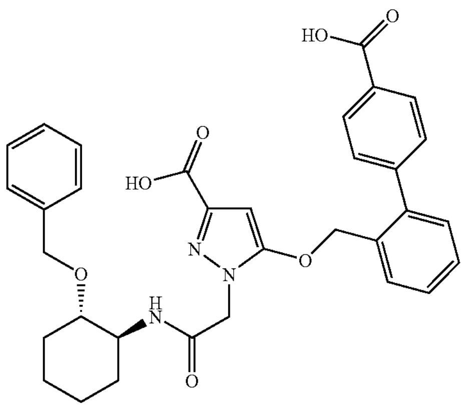 | >12.5 |
| 57 | 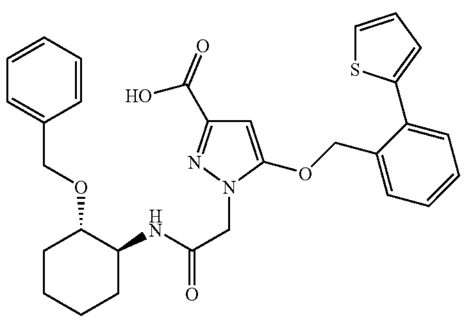 | 2.100 |
| 58 | 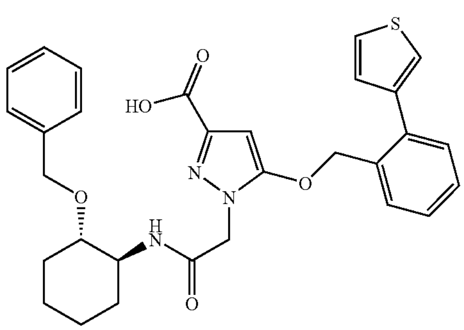 | 0.750 |
| 59 | 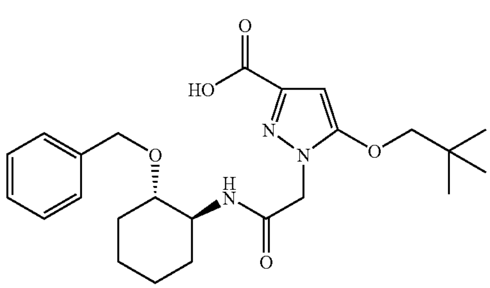 | >12.5 |

TABLE 2-continued

| Compound No. | Structure | Δ21 Activity (IC$_{50}$ μM) |
|---|---|---|
| 60 | 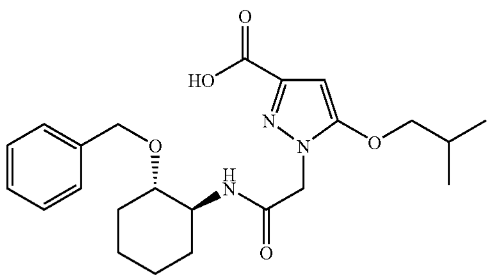 | >50 |
| 61 | 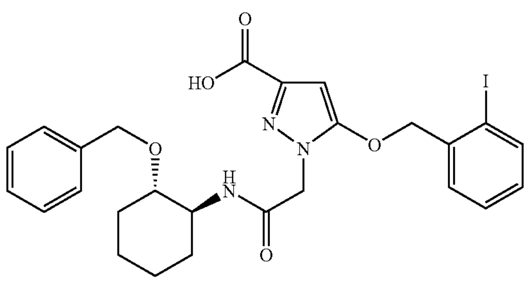 | 6.500 |
| 62 | 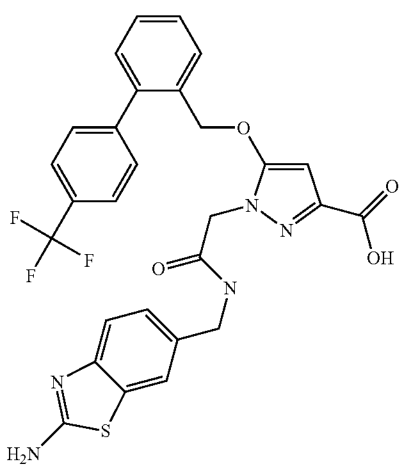 | >12.5 |

TABLE 2-continued

| Compound No. | Structure | Δ21 Activity (IC$_{50}$ μM) |
|---|---|---|
| 63 | 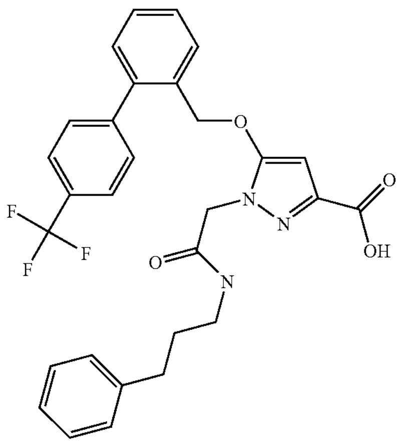 | 12.000 |
| 64 | 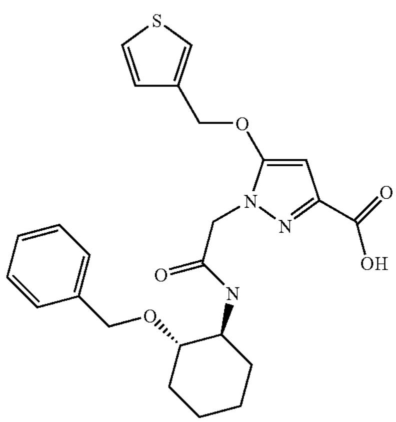 | >12.5 |
| 65 | 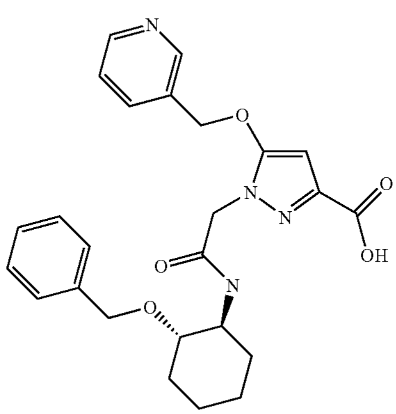 | >12.5 |

TABLE 2-continued

| Compound No. | Structure | Δ21 Activity (IC$_{50}$ μM) |
|---|---|---|
| 66 | 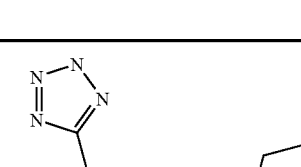 | 0.057 |

While the present invention has been described with in conjunction with the specific embodiments set forth above, many alternatives, modifications and other variations thereof will be apparent to those of ordinary skill in the art. All such alternatives, modifications and variations are intended to fall within the spirit and scope of the present invention.

What is claimed is:

1. A compound of formula I:

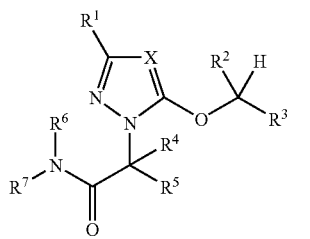

or a pharmaceutically acceptable salt or ester thereof, wherein:

X is C($R^8$) or N;

$R^8$ is H, halo, $CF_3$, $C_1$–$C_6$ alkyl, halo($C_1$–$C_6$)alkyl, —OH, —SH, $C_1$–$C_6$ alkoxy, $C_1$–$C_6$ alkylthio, —$NH_2$, —NH ($C_1$–$C_6$ alkyl), or —N($C_1$–$C_6$ alkyl)$_2$;

$R^1$ is —$CO_2R^9$, —C(O)$NR^9R^{10}$, —$NR^9SO_2R^{10}$, —CN, —C(O)$NR^9CN$, or tetrazolyl;

$R^2$ is cycloalkyl, aryl, aralkyl, heteroaryl, heteroaralkyl, alkyl, or cycloalkylalkyl, wherein each member of $R^2$ is optionally substituted with 1–4 $R^{12}$ moieties;

$R^3$ is H or $C_1$–$C_6$ alkyl;

$R^4$ is H, $C_1$–$C_6$ alkyl or $C_1$–$C_6$ alkoxy;

$R^5$ is H, $C_1$–$C_6$ alkyl or $C_1$–$C_6$ alkoxy;

$R^6$ is cycloalkyl, aryl, aralkyl, heteroaryl, heteroaralkyl, alkyl, or cycloalkylalkyl, wherein each member of $R^6$ is optionally substituted with 1–4 $R^{12}$ moieties;

$R^7$ is H or $C_1$–$C_6$ alkyl; or $R^6$ and $R^7$, when attached to the same nitrogen, are optionally taken together with the attached nitrogen to form a five to seven membered ring having 0–1 additional heteroatom selected from N, O or S, wherein said five to seven membered ring is optionally substituted with 1–3 $R^{18}$ moieties;

each $R^9$ is independently H, alkyl, cycloalkyl, cycloalkylalkyl, heterocyclyl, heterocyclylalkyl, aryl, aralkyl, heteroaryl, or heteroaralkyl, wherein each member except H is optionally substituted with 1–4 $R^{12}$ moieties;

each $R^{10}$ is independently H, alkyl, cycloalkyl, cycloalkylalkyl, heterocyclyl, heterocyclylalkyl, aryl, aralkyl, heteroaryl, or heteroaralkyl, wherein each member except H is optionally substituted with 1–4 $R^{12}$ moieties; or $R^9$ and $R^{10}$ when attached to the same nitrogen are optionally taken together with the attached nitrogen to form a five to sixteen membered monocyclic, bicyclic or tricyclic ring having 0–2 additional heteroatoms selected from N, O or S, wherein said monocyclic, bicyclic or tricyclic ring is optionally substituted with 1–3 $R^{18}$ moieties;

each $R^{12}$ is independently halo, alkyl, cycloalkyl, cycloalkylalkyl, heterocyclyl, heterocyclylalkyl, aryl, aralkyl, heteroaryl, heteroaralkyl, —CN, —$CF_3$, —$OR^{13}$, —$SR^{13}$, —C(O)$R^{13}$, —C(S)$R^{13}$, —C(O)$OR^{13}$, —C(S)$OR^{13}$, —OC(O)$R^{13}$, —OC(S)$R^{13}$, —C(O)$NR^{13}R^{14}$, —C(S)$NR^{13}R^{14}$, —C(O)$NR^{13}OR^{14}$, —C(S)$NR^{13}OR^{14}$, —C(O)$NR^{13}NR^{13}R^{14}$, —C(S) $NR^{13}NR^{13}R^{14}$, —C(S)$NR^{13}OR^{14}$, —C(O)$SR^{13}$, —$NR^{13}R^{14}$, —$NR^{13}C(O)R^{14}$, —$NR^{13}C(S)R^{14}$, —$NR^{13}C(O)OR^{14}$, —$NR^{13}C(S)OR^{14}$, —OC(O) $NR^{13}R^{14}$, —OC(S)$NR^{13}R^{14}$, —$NR^{13}C(O)NR^{13}R^{14}$, —$NR^{13}C(S)NR^{13}R^{14}$, —$NR^{13}C(O)NR^{13}R^{14}$, —$NR^{13}C(S)NR^{13}OR^{14}$, —$SO_2R^{13}$, —$S(O)_{1-2}NR^{13}R^{14}$, —N($R^{13}$)$SO_2R^{14}$, —N($R^{13}$)$SO_2NR^{13}R^{14}$, —$S(O)_{1-2}NR^{13}OR^{14}$, —$OCF_3$, —$SCF_3$, haloalkyl, =O, =S, $NO_2$, —C(O)C(O)$R^{13}$, —C(O)$CH_2$C(O) $R^{13}$, methylenedioxy, or ethylenedioxy, wherein each of said alkyl, cycloalkyl, cycloalkylalkyl, heterocyclyl, heterocyclylalkyl, aryl, aralkyl, heteroaryl or heteroaralkyl is optionally substituted with 1–4 $R^5$ moieties;

each $R^{13}$ is independently H, alkyl, cycloalkyl, cycloalkylalkyl, heterocyclyl, heterocyclylalkyl, aryl, aralkyl, heteroaryl, or heteroaralkyl, wherein each member of $R^{13}$ except H is optionally substituted with 1–4 $R^{15}$ moieties;

each $R^{14}$ is independently H, alkyl, cycloalkyl, cycloalkylalkyl, heterocyclyl, heterocyclylalkyl, aryl, aralkyl, heteroaryl, or heteroarylkyl, wherein each member of $R^{14}$ except H is optionally substituted with 1–4 $R^{15}$ moieties; or $R^{13}$ and $R^{14}$, when attached to the same nitrogen, are optionally taken together with the attached nitrogen to form a five to seven membered ring having 0–1 additional heteroatom selected from N, O or S, wherein said five to seven membered ring is optionally substituted with 1–3 $R^{18}$ moieties;

each $R^{15}$ is independently halo, alkyl, cycloalkyl, cycloalkylalkyl, heterocyclyl, heterocyclylalkyl, aryl, aralkyl, heteroaryl, heteroaralkyl, —CN, —CF$_3$, —OR$^{16}$, —SR$^{16}$, —C(O)R$^{16}$, —C(S)R$^{16}$, —C(O)OR$^{16}$, —C(S)OR$^{16}$, —OC(O)R$^{16}$, —OC(S)R$^{16}$, —C(O)NR$^{16}$R$^{17}$, —C(S)NR$^{16}$R$^{17}$, —C(O)NR$^{16}$OR$^{17}$, —C(S)NR$^{16}$OR$^{17}$, —C(O)NR$^{16}$NR$^{16}$R$^{17}$, —C(S)NR$^{16}$NR$^{16}$R$^{17}$, —C(S)NR$^{16}$OR$^{17}$, —C(O)SR$^{16}$, —NR$^{16}$R$^{17}$, —NR$^{16}$C(O)R$^{17}$, —NR$^{16}$C(S)R$^{17}$, —NR$^{16}$C(O)OR$^{17}$, —NR$^{16}$C(S)OR$^{17}$, —OC(O)NR$^{16}$R$^{17}$, —OC(S)NR$^{16}$R$^{17}$, —NR$^{16}$C(O)NR$^{16}$R$^{17}$, —NR$^{16}$C(S)NR$^{16}$R$^{17}$, —NR$^{16}$C(O)NR$^{16}$OR$^{17}$, —NR$^{16}$C(S)NR$^{16}$OR$^{17}$, —SO$_2$R$^{16}$, —S(O)$_{1-2}$NR$^{16}$R$^{17}$, —N(R$^{18}$)SO$_2$R$^{17}$, —S(O)$_{1-2}$NR$^{16}$OR$^{17}$, —OCF$_3$, —SCF$_3$, haloalkyl, =O, =S, NO$_2$, —C(O)C(O)R$^{16}$, —C(O)CH$_2$C(O)R$^{16}$, methylenedioxy, or ethylenedioxy, wherein each of said alkyl, cycloalkyl, cycloalkylalkyl, heterocyclyl, heterocyclylalkyl, aryl, aralkyl, heteroaryl or heteroaralkyl is optionally substituted with 1–3 $R^{18}$ moieties;

each $R^{16}$ is independently H, alkyl, cycloalkyl, cycloalkylalkyl, heterocyclyl, heterocyclylalkyl, aryl, aralkyl, heteroaryl or heteroaralkyl, wherein each member of $R^{16}$ is optionally substituted with 1–3 $R^{18}$;

each $R^{17}$ is independently H, alkyl, cycloalkyl, cyoloalkylalkyl, heterocyclyl, heterocyclylalkyl, aryl, aralkyl, heteroaryl or heteroaralkyl, wherein each member of $R^{16}$ is optionally substituted with 1–3 $R^{18}$; or $R^{16}$ and $R^{17}$, when attached to the same nitrogen, are optionally taken together with the attached nitrogen to form a five to seven membered ring having 0–1 additional heteroatom selected from N, O or S, wherein said five to seven membered ring is optionally substituted with 1–3 $R^{16}$ moieties;

each $R^{18}$ is halo, =O, =S, NO$_2$, alkyl, —OR$^{20}$, —CN, —NR$^{19}$R$^{20}$, —C(O)R$^{20}$, —C(O)OR$^{20}$, —C(O)NR$^{19}$R$^{20}$, —CF$_3$, or —N(R$^{19}$)C(O)R$^{20}$;

each $R^{19}$ is independently H or alkyl; and each $R^{20}$ is independently H or alkyl.

2. The compound of claim 1, wherein X is C(R$^8$).

3. The compound of claim 1, wherein R$^8$ is H.

4. The compound of claim 1, wherein X is N.

5. The compound of claim 1, wherein R$^3$ is H or CH$_3$ and R$^7$ is H or CH$_3$.

6. The compound of claim 1, wherein R$^2$ is alkyl, cycloalkyl, aryl, or heteroaryl, wherein said alkyl, cycloalkyl, aryl, or heteroaryl is optionally substituted with 1–2 R$^{12}$ moieties.

7. The compound of claim 6, wherein R$^2$ is i-propyl, t-butyl, phenyl, naphthyl, cyclohexyl, pyridyl, or thienyl, wherein said wherein said phenyl, naphthyl, cyclohexyl, pyridyl, or thienyl is optionally substituted with 1–2 R$^{12}$ moieties.

8. The compound of claim 7, wherein each R$^{12}$ is independently —OR$^{13}$, CF$_3$, halo, alkyl, 5-membered heteroaryl, —C(O)OR$^{13}$, or aryl, wherein said alkyl is optionally substituted with —SO$_2$R$^{16}$ and said aryl is optionally substituted with 1–2 R$^{15}$ moieties; R$^{13}$ is alkyl, aralkyl, or aryl optionally substituted with halo; R$^{15}$ is CF$_3$, SO$_2$R$^{16}$, —OR$^{16}$, —C(O)OR$^{20}$, or halo; and R$^{16}$ is alkyl.

9. The compound of claim 8, wherein each R$^{12}$ is —O—(phenyl optionally substituted with halo); CF$_3$, halo; C$_1$–C$_4$ alkyl; C$_1$–C$_4$ alkoxy; thienyl; —(CH$_2$)SO$_2$-phenyl; or phenyl optionally substituted with one or two moieties selected from the group consisting of CF$_3$, halo, C$_1$–C$_4$ alkoxy, —SO$_2$CH$_3$, and —CO$_2$H.

10. The compound of claim 1, wherein R$^6$ is cycloalkyl, aryl, aralkyl or heteroaryl, wherein said cycloalkyl, aryl, aralkyl or heteroaryl is optionally substituted with 1–2 R$^{12}$ moieties.

11. The compound of claim 10, wherein R$^6$ is cyclohexyl, phenyl, —(CH$_2$)$_{1-3}$-phenyl, or benzothiazolyl, wherein each member of R$^6$ is optionally substituted with 1–2 R$^{12}$ moieties.

12. The compound of claim 11, wherein R$^{12}$ is —OR$^{13}$ or —NR$^{13}$R$^{14}$ and R$^{13}$ is aralkyl.

13. The compound of claim 12, wherein R$^{13}$ is benzyl.

14. The compound of claim 1, wherein R$^1$ is —CO$_2$R$^9$ tetrazolyl.

15. The compound of claim 1, wherein R$^1$ is —CO$_2$H tetrazolyl.

16. The compound of claim 1, represented by formula II:

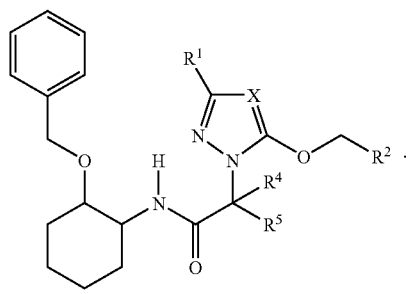

II

17. The compound of claim 16, wherein R$^2$ is aryl or heteroaryl, wherein said aryl or heteroaryl is optionally substituted with 1–2 R$^{12}$ moieties.

18. The compound of claim 17, wherein said aryl or heteroaryl is substituted with 1–2 R$^{12}$ moieties and one of the R$^{12}$ moieties is at the ortho-position.

19. The compound of claim 1, represented by formula II-a:

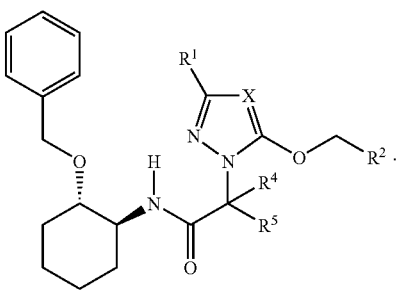

II-a

20. The compound of claim 1, represented by formula III:

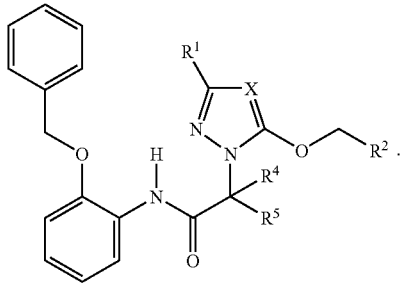

21. The compound of claim 20, wherein $R^2$ is aryl or heteroaryl, wherein said aryl or heteroaryl is optionally substituted with 1–2 $R^{12}$ moieties.

22. The compound of claim 21, wherein said aryl or heteroaryl is substituted with 1–2 $R^{12}$ moieties and one of the $R^{12}$ moieties is at the ortho-position.

23. The compound of claim 1 selected from Table 1:

TABLE 1

| Cpd | Structure | Cpd | Structure |
|---|---|---|---|
| 1 | 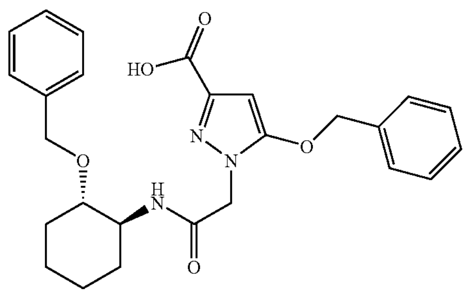 | 2 | 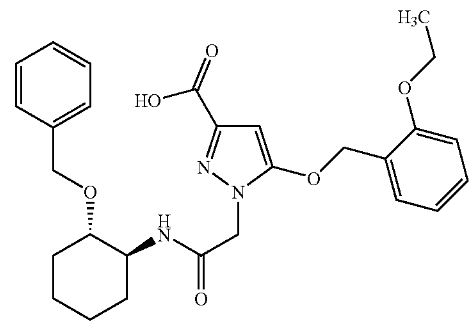 |
| 3 | 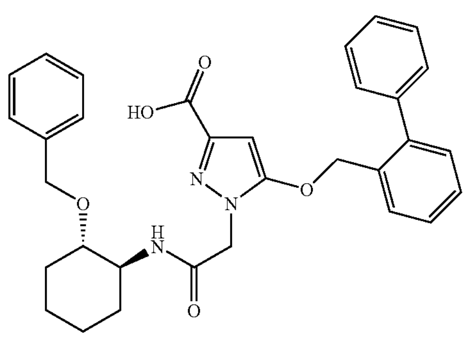 | 4 | 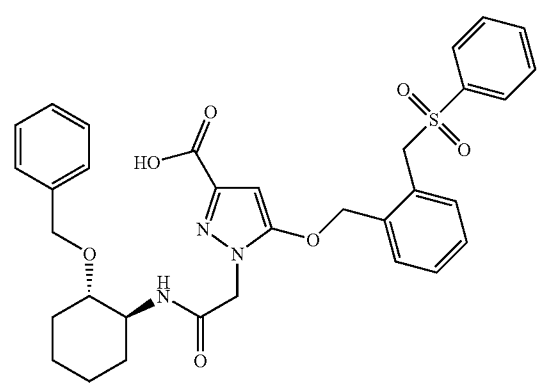 |
| 5 | 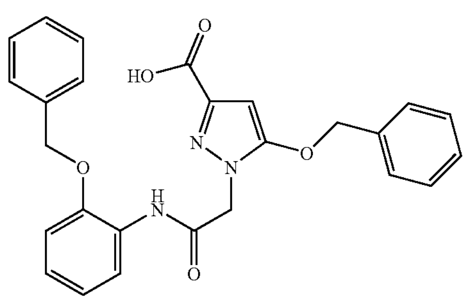 | 6 | 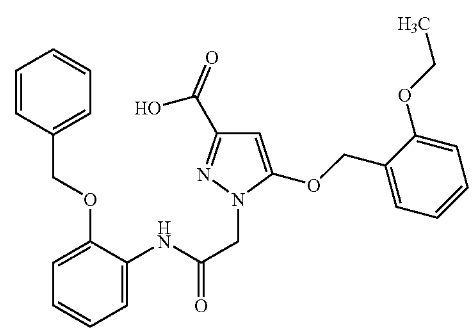 |

TABLE 1-continued

| Cpd | Structure | Cpd | Structure |
| --- | --- | --- | --- |
| 7 | 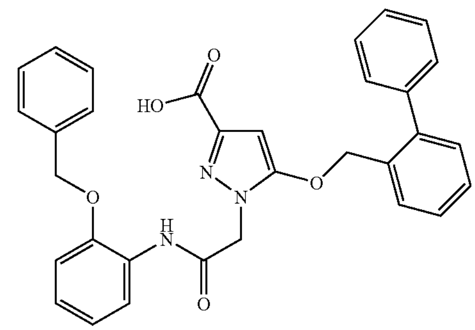 | 8 | 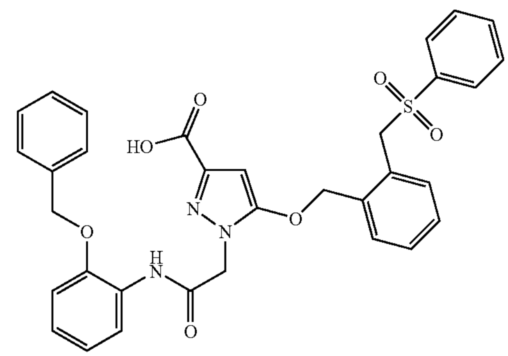 |
| 9 | 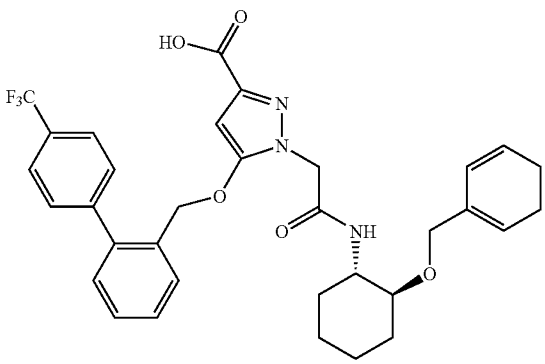 | 10 | 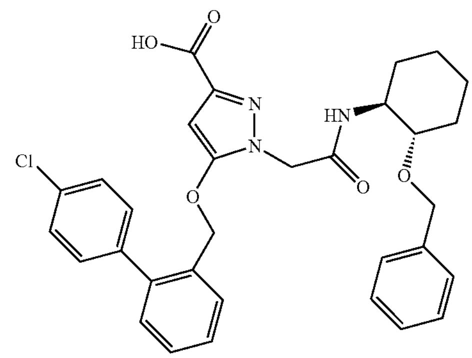 |
| 11 | 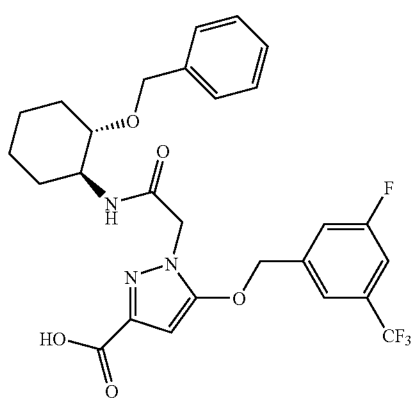 | 12 | 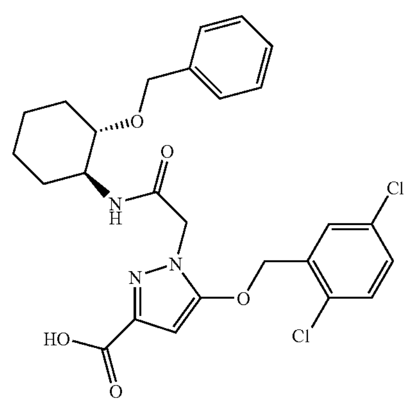 |
| 13 | 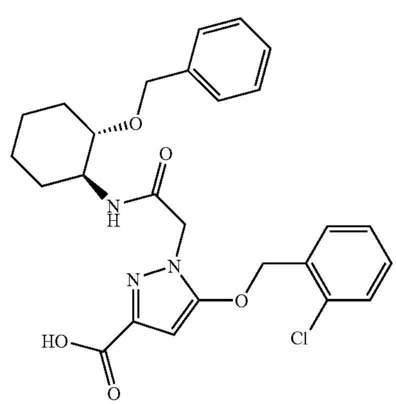 | 14 | 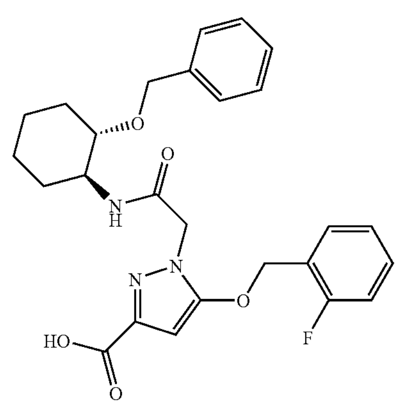 |

TABLE 1-continued

| Cpd | Structure | Cpd | Structure |
|-----|-----------|-----|-----------|
| 15 | 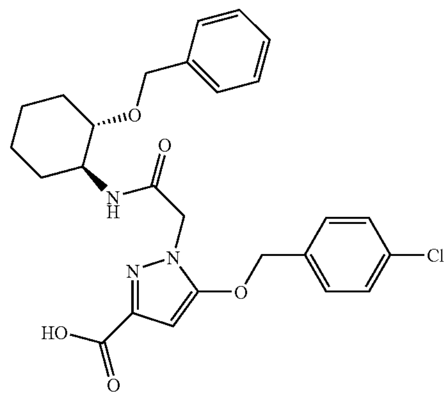 | 16 | 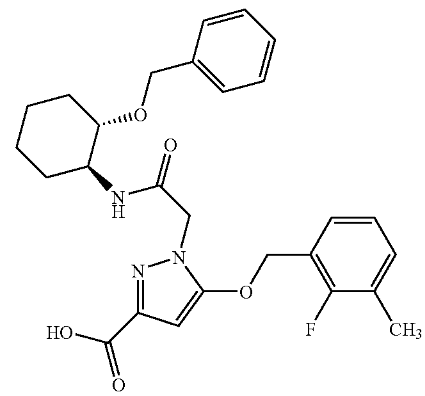 |
| 17 | 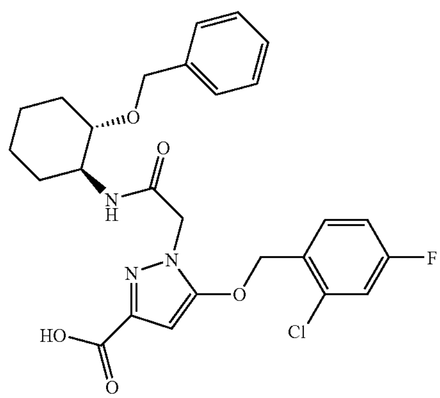 | 18 | 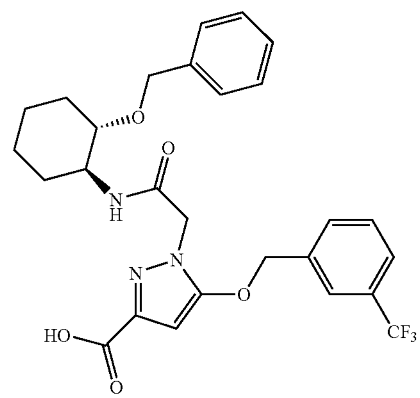 |
| 19 | 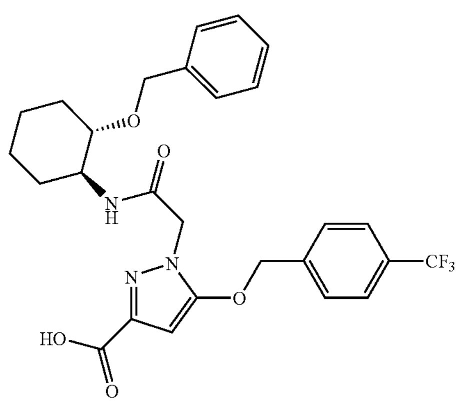 | 20 | 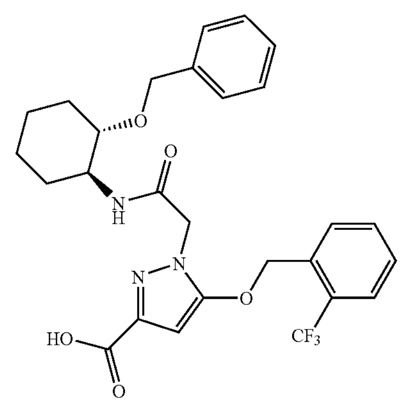 |
| 21 | 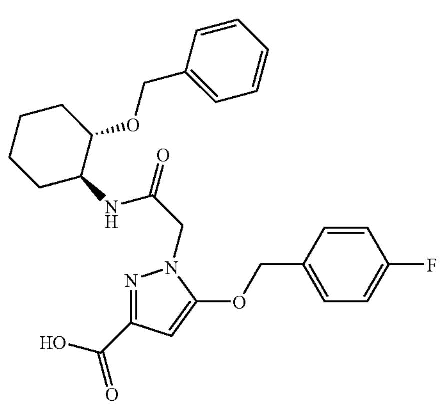 | 22 | 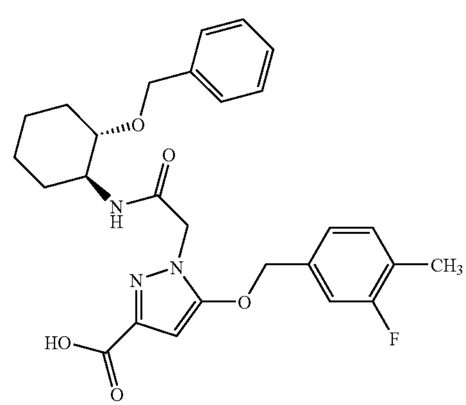 |

TABLE 1-continued

| Cpd | Structure | Cpd | Structure |
| --- | --- | --- | --- |
| 23 | 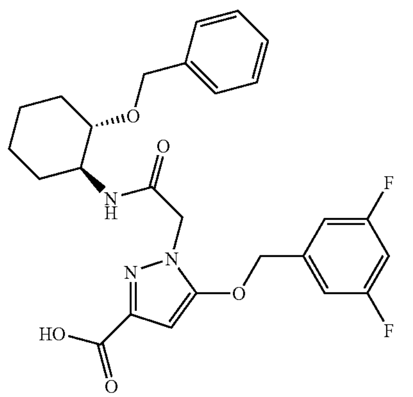 | 24 | 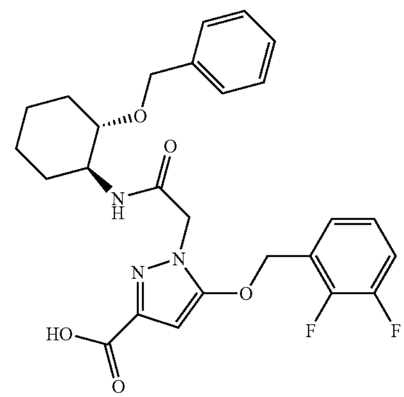 |
| 25 | 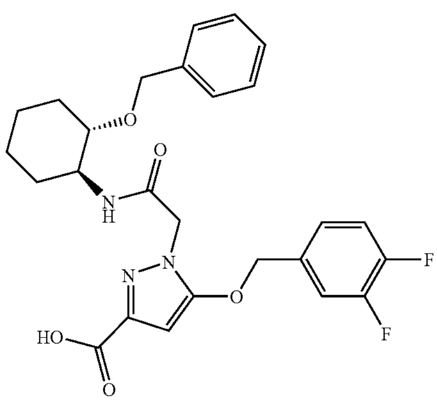 | 26 | 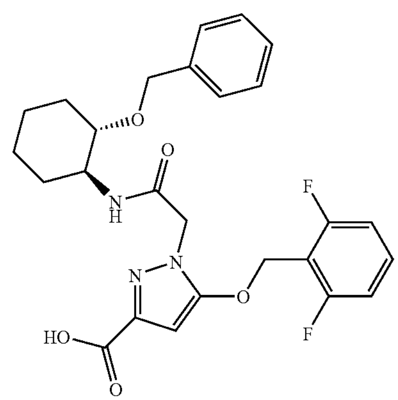 |
| 27 | 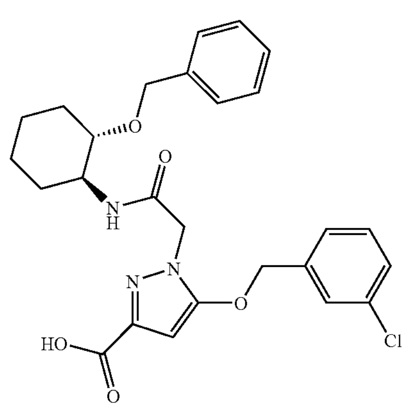 | 28 | 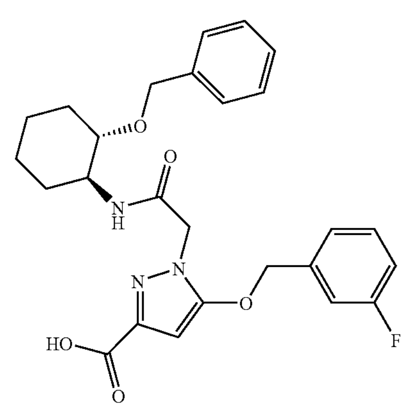 |

TABLE 1-continued

| Cpd | Structure | Cpd | Structure |
|-----|-----------|-----|-----------|
| 29  | 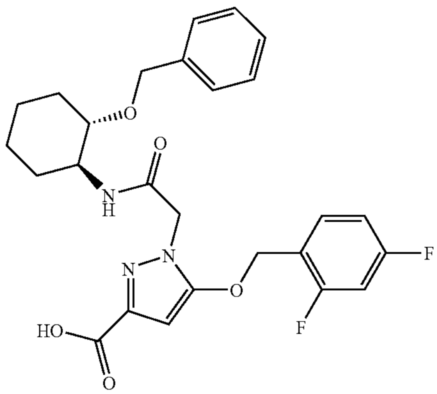          | 30  | 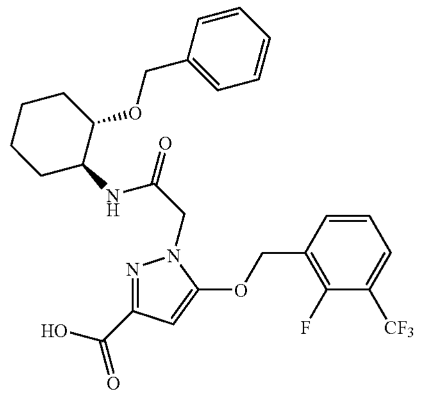          |
| 31  | 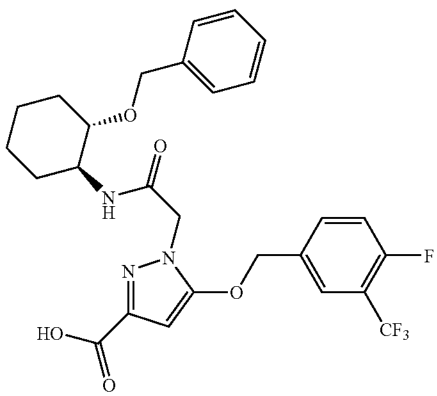          | 32  | 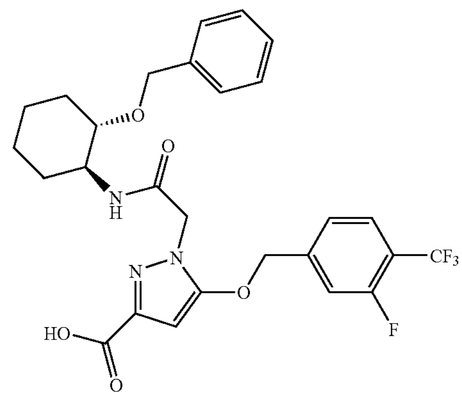          |
| 33  | 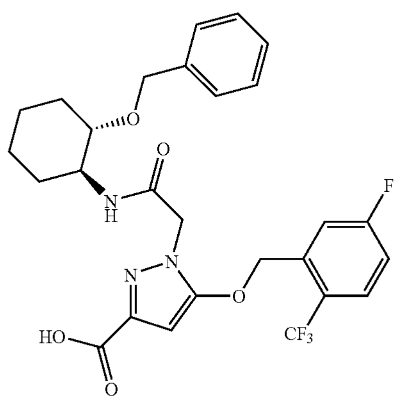          | 34  | 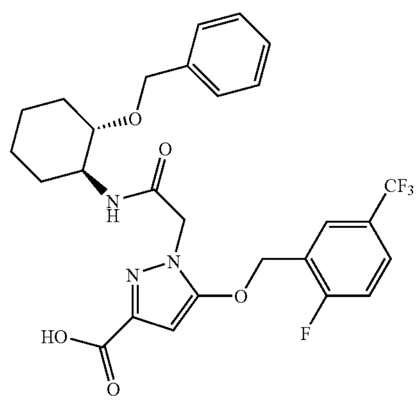          |
| 35  | 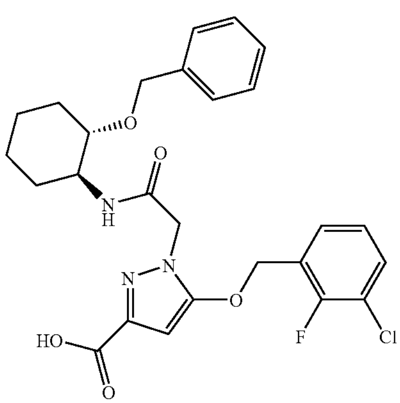          | 36  | 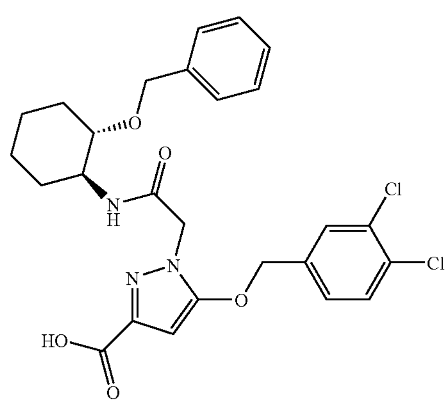          |

TABLE 1-continued

| Cpd | Structure | Cpd | Structure |
|-----|-----------|-----|-----------|
| 37 | 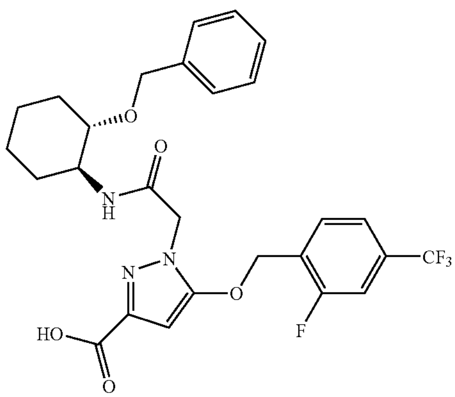 | 38 | 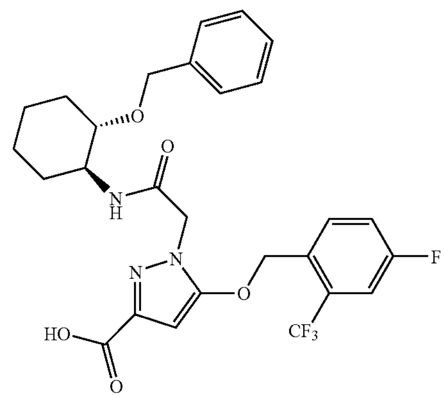 |
| 39 | 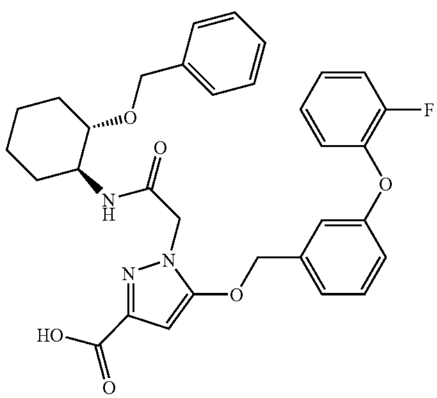 | 40 | 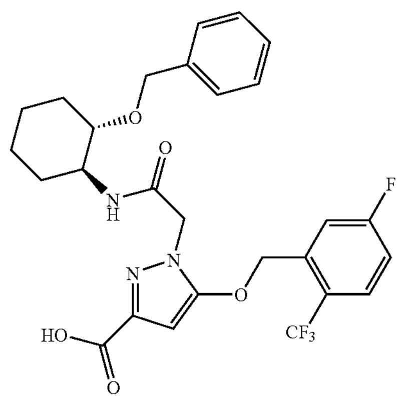 |
| 41 | 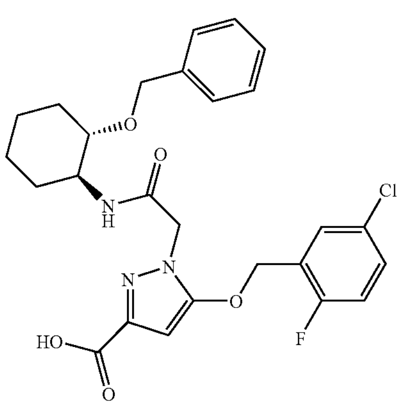 | 42 | 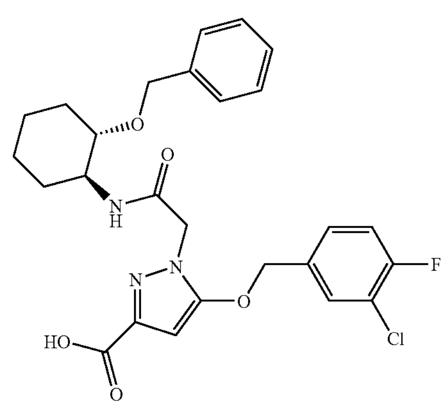 |

TABLE 1-continued

| Cpd | Structure | Cpd | Structure |
|---|---|---|---|
| 43 | 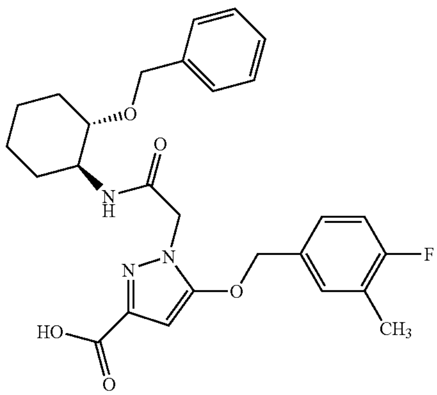 | 44 | 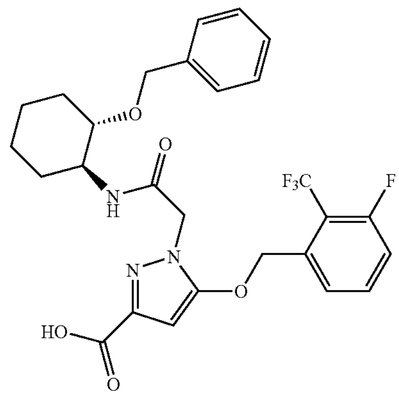 |
| 45 | 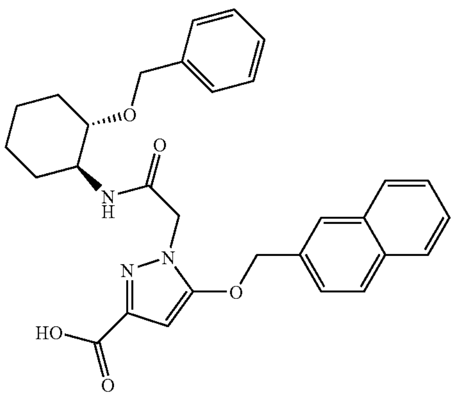 | 46 | 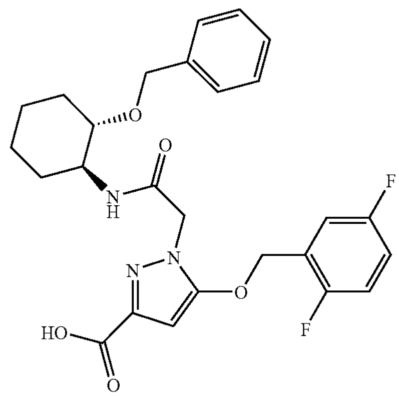 |
| 47 | 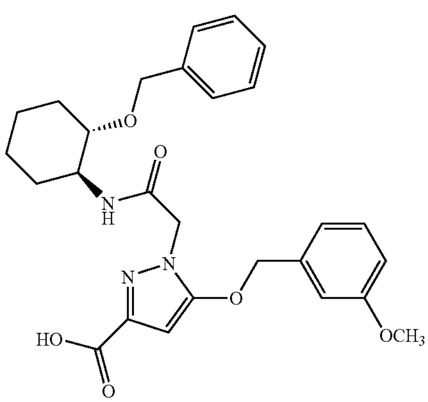 | 48 | 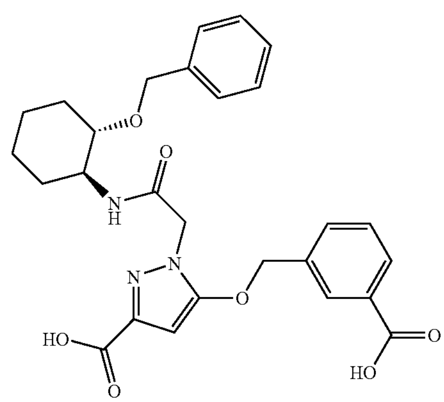 |
| 49 | 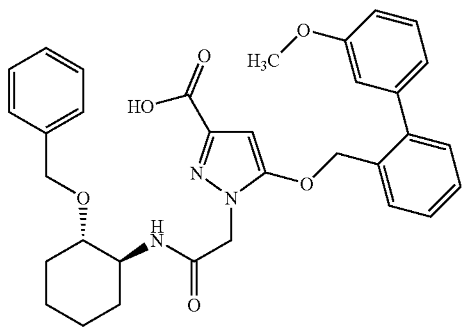 | 50 | 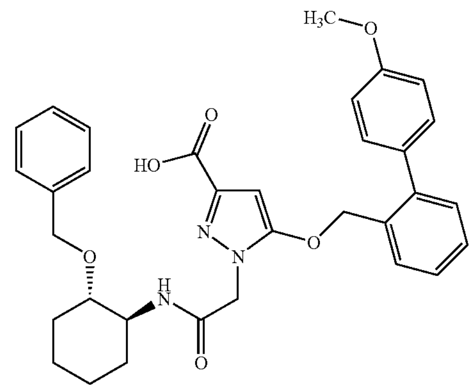 |

TABLE 1-continued

| Cpd | Structure | Cpd | Structure |
|---|---|---|---|
| 51 | 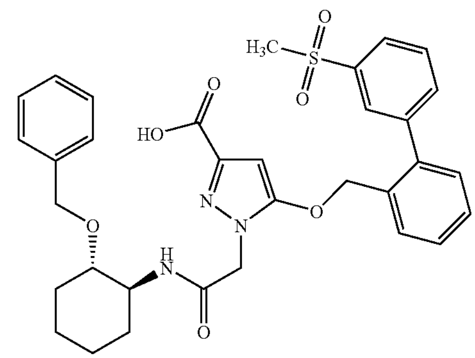 | 52 | 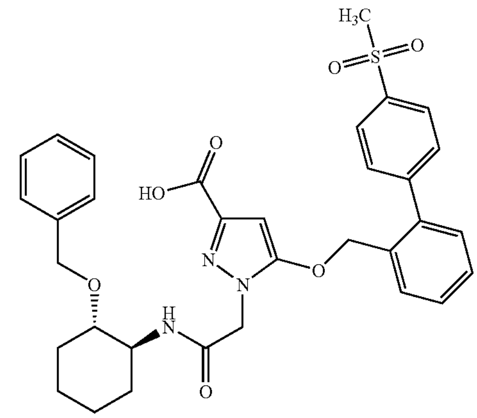 |
| 53 | 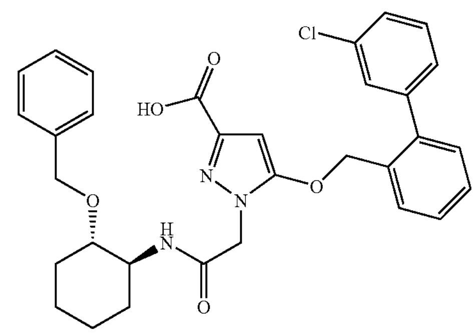 | 54 | 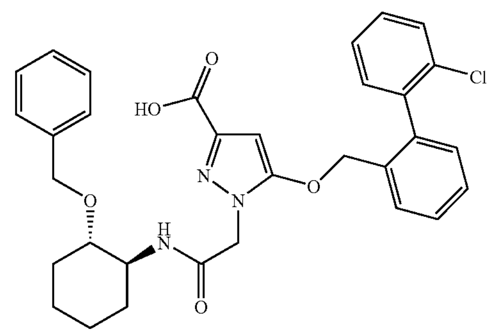 |
| 55 | 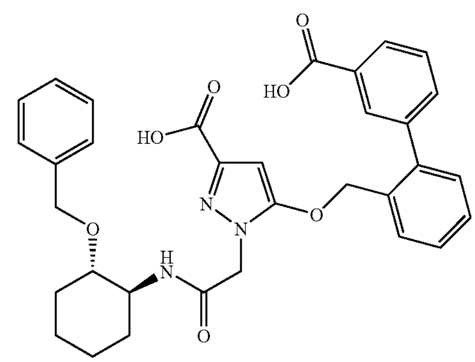 | 56 | 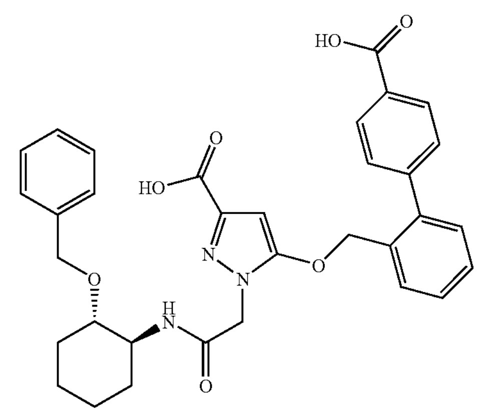 |
| 57 | 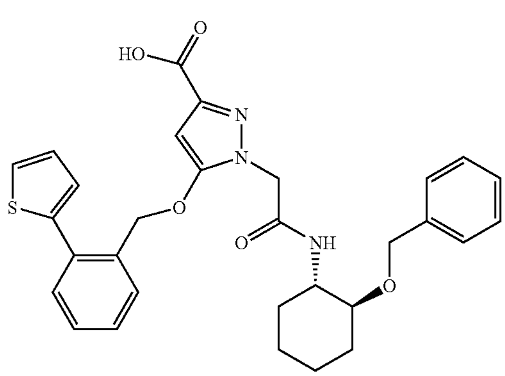 | 58 | 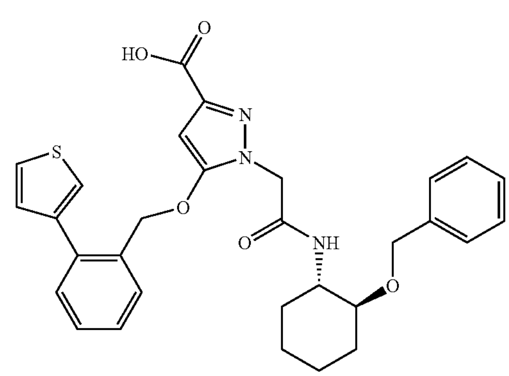 |

TABLE 1-continued

| Cpd | Structure | Cpd | Structure |
| --- | --- | --- | --- |
| 59 | 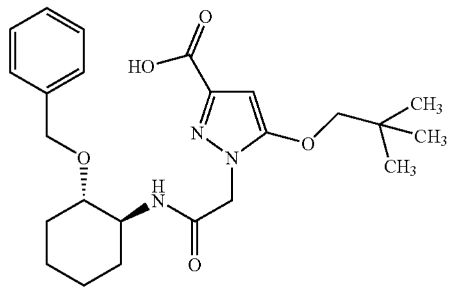 | 60 | 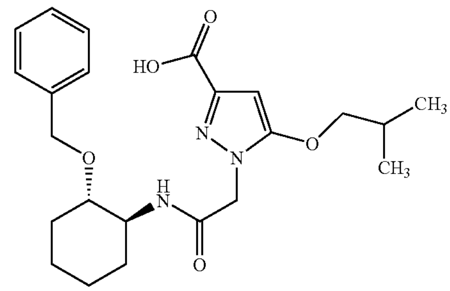 |
| 61 | 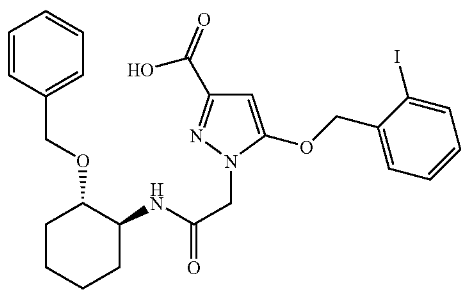 | 62 | 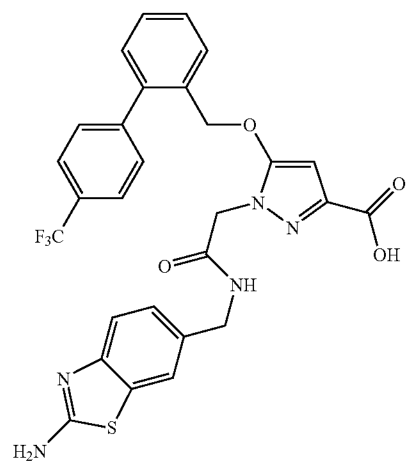 |
| 63 | 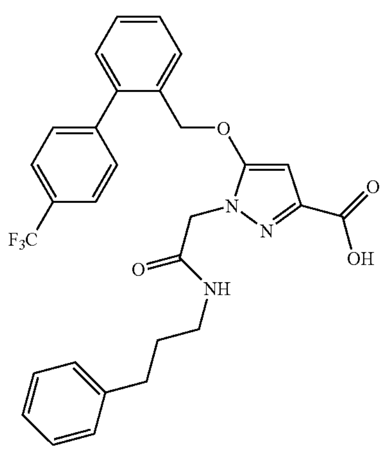 | 64 | 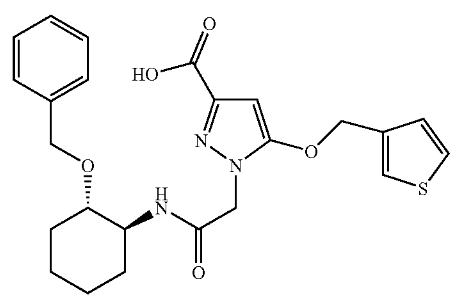 |
| 65 | 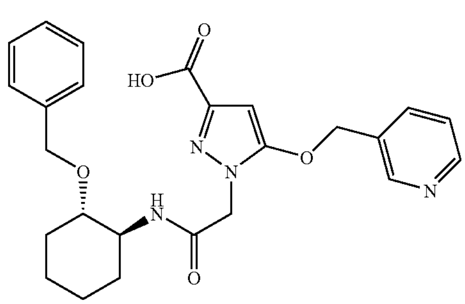 | 66 | 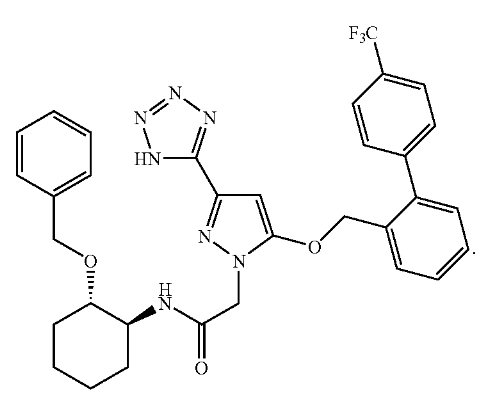 |

24. The compound of claim 23, wherein the compound is selected from Table 1 compounds 9, 10, 19, 32, 36, 50, 53, 58 and 66.

25. A pharmaceutical composition comprising at least one compound of claim 1, and at least one pharmaceutically acceptable carrier, adjuvant or vehicle.

26. The pharmaceutical composition of claim 25, further comprising one or more additional antiviral agent(s).

27. The pharmaceutical composition of claim 26, wherein said one additional antiviral agent is ribavirin.

28. The pharmaceutical composition of claim 26, further comprising an interferon or pegylated interferon.

29. The pharmaceutical composition of claim 28, wherein said additional antiviral agent is ribavirin and said interferon is α-interferon or pegylated interferon.

30. A pharmaceutical composition comprising at least one compound of claim 25 and a pharmaceutically acceptable carrier, adjuvant or vehicle.

* * * * *